US010140424B2

(12) United States Patent
Baym et al.

(10) Patent No.: US 10,140,424 B2
(45) Date of Patent: *Nov. 27, 2018

(54) MODIFYING A COSMETIC PRODUCT BASED ON A MICROBE PROFILE

(71) Applicant: Elwha LLC, Bellevue, WA (US)

(72) Inventors: Michael H. Baym, Cambridge, MA (US); Roderick A. Hyde, Redmond, WA (US); Jordin T. Kare, San Jose, CA (US); Eric C. Leuthardt, St. Louis, MO (US); Gary L. McKnight, Bothell, WA (US); Tony S. Pan, Bellevue, WA (US); Elizabeth A. Sweeney, Seattle, WA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/690,604

(22) Filed: Aug. 30, 2017

(65) Prior Publication Data

US 2017/0364665 A1     Dec. 21, 2017

Related U.S. Application Data

(63) Continuation of application No. 14/294,491, filed on Jun. 3, 2014, now Pat. No. 9,805,171, which is a
(Continued)

(51) Int. Cl.
*G06F 19/00* (2018.01)

(52) U.S. Cl.
CPC .................. *G06F 19/704* (2013.01)

(58) Field of Classification Search
None
See application file for complete search history.

(56) References Cited

U.S. PATENT DOCUMENTS

| 4,384,288 A | 5/1983 | Walton |
| 4,446,233 A | 5/1984 | Auditore-Hargreaves et al. |

(Continued)

FOREIGN PATENT DOCUMENTS

| JP | 2002-284618 A | 10/2002 |
| WO | WO 2008/059274 A1 | 5/2008 |

(Continued)

OTHER PUBLICATIONS

Adak et al.; "Bishydrazide Glycoconjugates for Lectin Recognition and Capture of Bacterial Pathogens"; Bioconjug Chem; Nov. 17, 2010; pp. 1-27; vol. 21; No. 11.
(Continued)

*Primary Examiner* — William C Vaughn, Jr.
*Assistant Examiner* — Stuart D Bennett

(57) ABSTRACT

Systems and methods are described for modifying a cosmetic product based on a microbe profile including an ingredient-microbe interaction dataset including information associated with interactions between reference cosmetic ingredients and types of reference microbes; and a computing device including circuitry configured to receive information associated with the microbe profile of an individual, receive information associated with an ingredient list of the cosmetic product, compare the microbe profile of the individual and the ingredient list of the cosmetic product to the ingredient-microbe interaction dataset, identify an interaction between at least one cosmetic ingredient in the ingredient list of the cosmetic product and at least one of the one or more types of microbes in the microbe profile of the individual, recommend a modification to the ingredient list in response to an identified interaction, and report to a user the recommended modification.

27 Claims, 45 Drawing Sheets

Related U.S. Application Data continuation-in-part of application No. 14/255,653, filed on Apr. 17, 2014, which is a continuation-in-part of application No. 14/192,613, filed on Feb. 27, 2014, now Pat. No. 10,010,704, which is a continuation-in-part of application No. 14/091,762, filed on Nov. 27, 2013, now Pat. No. 9,526,480, which is a continuation-in-part of application No. 14/091,832, filed on Nov. 27, 2013, now Pat. No. 9,549,703, which is a continuation-in-part of application No. 13/975,055, filed on Aug. 23, 2013, now Pat. No. 9,390,312.

(56) References Cited

U.S. PATENT DOCUMENTS

| | | |
|---|---|---|
| 5,077,210 A | 12/1991 | Eigler et al. |
| 5,299,121 A * | 3/1994 | Brill .................. G06F 19/326 128/923 |
| 5,464,013 A | 11/1995 | Lemelson |
| 5,544,651 A | 8/1996 | Wilk |
| 5,728,028 A | 3/1998 | Dusch |
| 5,747,022 A | 5/1998 | Slavtcheff |
| 6,106,457 A | 8/2000 | Perkins et al. |
| 6,199,557 B1 | 3/2001 | Laughlin |
| 6,255,461 B1 | 7/2001 | Mosbach et al. |
| 6,291,234 B1 | 9/2001 | Raz et al. |
| 6,371,370 B2 | 4/2002 | Sadler et al. |
| 6,379,920 B1 | 4/2002 | El-Sayed et al. |
| 6,433,244 B1 | 8/2002 | Roe et al. |
| 6,782,307 B2 | 8/2004 | Wilmott et al. |
| 6,797,522 B1 | 9/2004 | Still et al. |
| 6,802,811 B1 | 10/2004 | Slepian |
| 6,905,692 B2 | 6/2005 | Farmer |
| 6,961,517 B2 * | 11/2005 | Merola .................. G03B 1/00 356/369 |
| 7,070,590 B1 | 7/2006 | Santini, Jr. et al. |
| 7,215,976 B2 | 5/2007 | Brideglall |
| 7,303,875 B1 | 12/2007 | Bock et al. |
| 7,314,453 B2 | 1/2008 | Kuo |
| 7,319,038 B2 | 1/2008 | Southard |
| 7,349,857 B2 * | 3/2008 | Manzo .................. G06F 19/00 705/2 |
| 7,386,333 B1 | 6/2008 | Birecki et al. |
| 7,413,567 B2 | 8/2008 | Weckwerth et al. |
| 7,494,465 B2 | 2/2009 | Brister et al. |
| 7,507,402 B1 | 3/2009 | Farmer et al. |
| 7,931,592 B2 | 4/2011 | Currie et al. |
| 8,028,708 B2 | 10/2011 | Molema et al. |
| 8,041,147 B2 | 10/2011 | Molnar et al. |
| 8,109,875 B2 | 2/2012 | Gizewski |
| 8,260,010 B2 | 9/2012 | Chhibber et al. |
| 8,280,471 B2 | 10/2012 | Rainone et al. |
| 8,358,348 B2 | 1/2013 | Mohammadi et al. |
| 8,385,619 B2 | 2/2013 | Soenksen |
| 8,475,789 B2 | 7/2013 | Bisgaard-Frantzen |
| 8,557,560 B2 | 10/2013 | Martin Jiménez et al. |
| 8,620,451 B2 | 12/2013 | Kennedy |
| 9,028,846 B2 | 5/2015 | Eddy |
| 9,186,278 B2 | 11/2015 | Baym et al. |
| 9,289,140 B2 | 3/2016 | Ross et al. |
| 2003/0007942 A1 | 1/2003 | Koenig |
| 2003/0108896 A1 | 6/2003 | Vogt |
| 2003/0173525 A1 | 9/2003 | Seville |
| 2003/0225362 A1 | 12/2003 | Currie et al. |
| 2004/0013828 A1 | 1/2004 | Tewes-Schwarzer |
| 2004/0078219 A1 | 4/2004 | Kaylor et al. |
| 2004/0111035 A1 | 6/2004 | Kondoh et al. |
| 2004/0125996 A1 * | 7/2004 | Eddowes ............. A61B 5/0059 382/128 |
| 2004/0202685 A1 | 10/2004 | Manzo |
| 2004/0223985 A1 | 11/2004 | Dunfield et al. |
| 2005/0019291 A1 | 1/2005 | Zolotarsky et al. |
| 2005/0021173 A1 * | 1/2005 | Pinney ............... G06F 19/3462 700/231 |
| 2005/0142093 A1 | 6/2005 | Skover et al. |
| 2005/0154381 A1 | 7/2005 | Altshuler et al. |
| 2005/0154382 A1 | 7/2005 | Altshuler et al. |
| 2005/0171434 A1 | 8/2005 | Madden et al. |
| 2005/0197652 A1 | 9/2005 | Nat |
| 2006/0037197 A1 | 2/2006 | Hawes et al. |
| 2006/0048278 A1 | 3/2006 | Pitsolis |
| 2006/0052739 A1 | 3/2006 | Henley et al. |
| 2006/0111620 A1 | 5/2006 | Squilla et al. |
| 2006/0172318 A1 | 8/2006 | Medinz et al. |
| 2006/0257993 A1 | 11/2006 | McDevitt et al. |
| 2007/0031028 A1 | 2/2007 | Vetter et al. |
| 2007/0035815 A1 | 2/2007 | Edgar et al. |
| 2007/0059736 A1 | 3/2007 | Saito et al. |
| 2007/0128589 A1 | 6/2007 | Sanders et al. |
| 2007/0134337 A1 | 6/2007 | Villanueva et al. |
| 2007/0134649 A1 | 6/2007 | Kolari et al. |
| 2008/0060148 A1 | 3/2008 | Pinyayev et al. |
| 2008/0139974 A1 | 6/2008 | Da Silva |
| 2008/0262321 A1 | 10/2008 | Erad et al. |
| 2008/0262576 A1 | 10/2008 | Creamer et al. |
| 2009/0001012 A1 | 1/2009 | Kepner et al. |
| 2009/0041727 A1 | 2/2009 | Suzuki et al. |
| 2009/0186342 A1 | 7/2009 | Bruno et al. |
| 2009/0202045 A1 | 8/2009 | Guertin et al. |
| 2009/0286263 A1 | 11/2009 | Graham et al. |
| 2010/0055161 A1 | 3/2010 | Ahn |
| 2010/0063565 A1 | 3/2010 | Beerwerth et al. |
| 2010/0068247 A1 | 3/2010 | Mou et al. |
| 2010/0074872 A1 | 3/2010 | Blaser et al. |
| 2010/0185064 A1 | 7/2010 | Bandic et al. |
| 2010/0204802 A1 | 8/2010 | Wilson et al. |
| 2010/0239625 A1 | 9/2010 | Puckett et al. |
| 2010/0292964 A1 | 11/2010 | Tam et al. |
| 2010/0331641 A1 | 12/2010 | Bangera et al. |
| 2011/0035898 A1 | 2/2011 | Marek et al. |
| 2011/0040571 A1 | 2/2011 | Warren |
| 2011/0117025 A1 | 5/2011 | Dacosta et al. |
| 2011/0172591 A1 | 7/2011 | Babaev |
| 2011/0212485 A1 | 9/2011 | Mitragotri et al. |
| 2011/0245094 A1 | 10/2011 | Washburn et al. |
| 2011/0274676 A1 | 11/2011 | Farmer et al. |
| 2011/0300196 A1 | 12/2011 | Mohammadi et al. |
| 2012/0017929 A1 | 1/2012 | Samain et al. |
| 2012/0058464 A1 | 3/2012 | Ermantraut et al. |
| 2012/0065086 A1 | 3/2012 | Benson |
| 2012/0092461 A1 | 4/2012 | Fisker et al. |
| 2012/0171193 A1 | 7/2012 | Blaser et al. |
| 2012/0192884 A1 | 8/2012 | Nasu et al. |
| 2012/0241391 A1 | 9/2012 | Carlson et al. |
| 2012/0253224 A1 | 10/2012 | Mir et al. |
| 2013/0057866 A1 * | 3/2013 | Hillebrand .......... A45D 44/005 356/421 |
| 2013/0078298 A1 | 3/2013 | Av-Gay et al. |
| 2013/0079605 A1 | 3/2013 | Bandaru et al. |
| 2013/0084259 A1 | 4/2013 | Lee |
| 2013/0115317 A1 | 5/2013 | Charbonneau et al. |
| 2013/0115610 A1 | 5/2013 | Lanzalaco et al. |
| 2013/0178791 A1 | 7/2013 | Javitt |
| 2013/0217947 A1 | 8/2013 | Fishman |
| 2013/0218024 A1 | 8/2013 | Boctor et al. |
| 2013/0224155 A1 | 8/2013 | Kaplan et al. |
| 2013/0244977 A1 | 9/2013 | Lee et al. |
| 2013/0317741 A1 | 11/2013 | Brashear et al. |
| 2013/0338039 A1 | 12/2013 | Mazed et al. |
| 2014/0037688 A1 | 2/2014 | Berkes et al. |
| 2014/0271964 A1 | 9/2014 | Roberts, IV et al. |
| 2014/0309662 A1 | 10/2014 | Brewer et al. |
| 2015/0054944 A1 | 2/2015 | Bangera et al. |
| 2015/0054945 A1 | 2/2015 | Bangera et al. |
| 2015/0148684 A1 | 5/2015 | Baym et al. |
| 2015/0148685 A1 | 5/2015 | Baym et al. |
| 2015/0339513 A1 | 11/2015 | Bolea |
| 2016/0032365 A1 | 2/2016 | Maitra et al. |

FOREIGN PATENT DOCUMENTS

| | | |
|---|---|---|
| WO | WO 2008/086596 A1 | 7/2008 |
| WO | WO 2010/093503 A2 | 8/2010 |
| WO | WO 2010/094976 A1 | 8/2010 |

(56) References Cited

FOREIGN PATENT DOCUMENTS

| WO | WO 2011/103144 A1 | 8/2011 |
|----|-------------------|--------|
| WO | WO 2012/044794 A2 | 4/2012 |
| WO | WO 2013/012924 A2 | 1/2013 |
| WO | WO 2013/070893 A1 | 5/2013 |

OTHER PUBLICATIONS

Alexander et al.; "Molecular imprinting science and technology: a survey of the literature for the years up to and including 2003"; Journal of Molecular Recognition; Jan. 4, 2006; pp. 106-180; vol. 19; John Wiley & Sons, Ltd.
Ammor, Mohammed Salim; "Recent Advances in the Use of Intrinsic Fluorescence for Bacterial Identification and Characterization"; J Fluoresc; Mar. 12, 2007; pp. 1-5; Springer Science + Business Media, LLC.
Baddour et al.; "High Frequency Ultrasound Imaging of Changes in Cell Structure Including Apoptosis"; PDF created on Aug. 12, 2013; pp. 1-6; IEEE.
Banin et al.; "Iron and *Pseudomonas aeruginosa* biofilm formation"; PNAS; Aug. 2, 2005; pp. 11076-11081; vol. 102, No. 31; The National Academy of Sciences of the USA.
Barlen et al.; "Detection of *Salmonella* by Surface Plasmon Resonance"; Sensors; Aug. 7, 2007; pp. 1427-1446; vol. 7; MDPI.
Bateni et al.; The Use of Konjac Glucomannan Hydrolysates (GMH) to Improve the Health of the Skin and Reduce Acne Vulgaris; American Journal of Dermatology and Venereology; pp. 10-14; bearing a date of 2013; created on Feb. 19, 2014; Scientific & Academic Publishing.
Belkaid et al; "Compartmentalized and Systemic Control of Tissue Immunity by Commensals"; Nat. Immunol.; Jul. 2013; pp. 1-17; vol. 14; Issue 7.
Bernardini et al.; "The 3D Model Acquisition Pipeline"; Computer Graphics Forum; 2002; pp. 149-172; vol. 21; No. 2; The Eurographics Association and Blackwell Publishers Ltd.
Bhatta et al.; "Use of Fluorescence Spectroscopy to Differentiate Yeast and Bacterial Cells"; Applied Microbiology and Biotechnology; 2006; pp. 121-126; vol. 71; No. 1.
Blank et al.; "A force-based protein biochip"; PNAS; Sep. 30, 2003; pp. 11356-11360; vol. 100; No. 20; The National Academy of Sciences of the USA.
Bouchard et al.; "Optical characterization of Pseudomonas fluorescens on meat surfaces using time-resolved fluorescence"; Journal of Biomedical Optics; Jan./Feb. 2006; pp. 014011-1-014011-7; vol. 11; No. 1.
Brennan, John D.; "Preparation and Entrapment of Fluorescently Labeled Proteins for the Development of Reagentless Optical Biosensors"; Journal of Fluorescence; Apr. 28, 1999; pp. 295-312; vol. 9; No. 4; Plenum Publishing Corporation.
Buckley et al.; A Three-Dimensional Morphometric Study of Craniofacial Shape in Schizophrenia; Am J Psychiatry; Mar. 2005; pp. 606-608.
Bright et al.; "Regenerable Fiber-Optic-Based Immunosensor"; Analytical Chemistry; May 15, 1990; pp. 1065-1069; vol. 62, No. 10; American Chemical Society.
Cady et al.; "Optimized linkage and quenching strategies for quantum dot molecular beacons"; Molecular and Cellular Probes; 2007; pp. 116-124; vol. 21; Elsevier Ltd.
Cao et al.; "Molecular Beacon Aptamers for Protein Monitoring in Real-Time and in Homogeneous Solutions"; Current Proteomics; 2005; pp. 31-40; vol. 2; Bentham Science Publishers Ltd.
Chawla et al.; "An overview of passive RFID"; IEEE Applications & Practice; Sep. 2007; pp. 11-17; IEEE.
Chen et al.; "Aptamer from whole-bacterium SELEX as new therapeutic reagent against virulent *Mycobacterium tuberculosis*"; Biochemical and Biophysical Research Communications; Apr. 11, 2007; pp. 743-748; vol. 357; Elsevier Inc.
Cho et al.; "The Human Microbiome: at the interface of health and disease"; Nat Rev Genet; Oct. 1, 2012; pp. 260-270; vol. 13; No. 4.

Chung et al.; "Size Comparisons among Integral Membrane Transport Protein Homologues in Bacteria, Archaea, and Eucarya"; Journal of Bacteriology; Feb. 2001; pp. 1012-1021; vol. 183; No. 3; American Society for Microbiology.
Cockburn et al.; "High throughput DNA sequencing to detect differences in the subgingival plaque microbiome in elderly subjects with and without dementia"; Investigative Genetics; 2012; pp. 1-12; vol. 3; No. 19; Cockburn et al, Biomed Central Ltd.
Cole et al.; "The Ribosomal Database Project: improved alignments and new tools for rRNA analysis"; Nucleic Acids Research; published online Nov. 12, 2008; pp. D141-D145; vol. 37; The Author(s).
Cowan et al.; "Development of engineered biofilms on poly-L-lysine patterned surfaces"; Biotechnology Letters; Accepted May 23, 2001; pp. 1235-1241; vol. 23; Kluwer Academic Publishers; Netherlands.
Crawford et al.; "Peptide aptamers: Tools for biology and drug discovery"; Briefings in Functional Genomics and Proteomics; Apr. 2003; pp. 72-79; vol. 2; No. 1; Henry Stewart Publications.
Crowe et al.; "Candida albicans binds human plasminogen: identification of eight plasminogen-binding proteins"; Molecular Microbiology; 2003; pp. 1637-1651; vol. 47; No. 6; Blackwell Publishing Ltd.
De Château et al.; "Protein PAB, an Albumin-binding Bacterial Surface Protein Promoting Growth and Virulence"; The Journal of Biological Chemistry; revised Jul. 22, 1996; pp. 26609-26615; vol. 271; No. 43; Issue of Oct. 25, 1996; The American Society for Biochemistry and Molecular Biology, Inc.; USA.
Dewhirst et al.; "The Human Oral Microbiome"; Journal of Bacteriology; Accepted Jul. 10, 2010; pp. 5002-5017; vol. 192; No. 19; American Society for Microbiology.
Didenko et al.; "Horseradish peroxidase-driven fluorescent labeling of nanotubes with quantum dots"; Biotechniques; NIH Public Access Author Manuscript; Mar. 2006; pp. 295-302; vol. 40; No. 3.
Doornbos et al.; "White Blood Cell Differentiation Using a Solid State Flow Cytometer"; Cytometry; accepted Mar. 16, 1993; pp. 589-594; vol. 14; Wiley-Liss, Inc.
Dwarakanath et al.; "Quantum dot-antibody and aptamer conjugates shift fluorescence upon binding bacteria"; Biochemical and Biophysical Research Communications; pp. 739-743; vol. 325; Elsevier Inc.
Elston, Dirk M.; "Fluorescence of fungi in superficial and deep fungal infections"; BMC Microbiology; Sep. 24, 2001; pp. 1-4; vol. 1; No. 21; Elston.
Fan et al.; "Sensitive optical biosensors for unlabeled targets: A review"; Analytica Chimica Acta; 2008; pp. 8-26; vol. 620; Elsevier B.V.
Fan et al.; "Structures in Bacillus subtilis Are Recognized by CD14 in a Lipopolysaccharide Binding Protein-Dependent Reaction"; Infection and Immunity; Jun. 1999; pp. 2964-2968; vol. 67; No. 6; American Society for Microbiology.
Fei-Fei et al.; "One-Shot Learning of Object Categories"; IEEE Transactions on Pattern Analysis and Machine Intelligence; Apr. 2006; pp. 594-611; vol. 28; No. 4; IEEE Computer Society.
Feng et al.; "Computer-assisted technique for the design and manufacture of realistic facial prostheses"; British Journal of Oral and Maxillofacial Surgery; 2010; pp. 105-109; vol. 48; The British Association of Oral and Maxillofacial Surgeons.
Finkenzeller, Klaus; "RFID Handbook: Fundamentals and Applications in Contactless Smart Cards and Identification"; 2003; pp. 29-59; John Wiley & Sons, Ltd.
Frank et al.; "The Human Nasal Microbiota and *Staphylococcus aureus* Carriage"; PLoS One; May 2010; pp. 1-15; vol. 5; Issue 5.
Freeman et al.; "Chemiluminescent and Chemiluminescence Resonance Energy Transfer (CRET) Detection of DNA, Metal Ions, and Aptamer—Substrate Complexes Using Hemin/G-Quadruplexes and CdSe/ZnS Quantum Dots"; Journal of The American Chemical Society; 2011; pp. 11597-11604; vol. 133; American Chemical Society.
Froebe et al.; "Axillary malodor production: A new mechanism"; J. Soc. Cosmet. Chem.; May/Jun. 1990; pp. 173-185; vol. 41.
Gaitanis et al.; "The *Malassezia* Genus in Skin and Systemic Diseases"; Clinical Microbiology Reviews; Jan. 2012; pp. 106-141; vol. 25; No. 1; American Society for Microbiology.

(56) References Cited

OTHER PUBLICATIONS

Gao et al.; "A Micro Sensing Probe for Detecting Individual Biological Cells"; Proceedings of the 25th Annual International Conference of the IEEE EMBS, Cancun, Mexico; Sep. 17-21, 2003; pp. 3348-3351; IEEE.
Gauglitz et al.; "Host Defence Against Candida albicans and the Role of Pattern-recognition Receptors"; Acta Derm Venereol; 2012; pp. 291-298; vol. 92; The Authors; Journal Compilation: Acta Dermato-Venereologica.
Giana et al.; "Rapid Identification of Bacterial Species by Fluorescence Spectroscopy and Classification Through Principal Components Analysis"; Journal of Fluorescence; Nov. 2003; pp. 489-493; vol. 13, No. 6; Plenum Publishing Corporation.
Gopinath et al.; "Aptamer That Binds to the gD Protein of Herpes Simplex Virus 1 and Efficiently Inhibits Viral Entry"; Journal of Virology; Jun. 2012; pp. 6732-6744; vol. 86; No. 12; American Society for Microbiology.
Graham, Anna R.; "Fungal Autofluorescence with Ultraviolet Illumination"; American Journal of Clinical Pathology; Feb. 1983; pp. 231-234; vol. 79; No. 2; American Society of Clinical Pathologists.
Grice et al.; "A diversity profile of the human skin microbiota"; Genome Research; 2008; pp. 1043-1050; vol. 18; Cold Spring Harbor Laboratory Press.
Grice et al.; "The skin microbiome"; Nature Reviews—Microbiology; Apr. 2011; pp. 244-253; vol. 9; Macmillan Publishers Limited.
Grice et al.; "Topographical and Temporal Diversity of the Human Skin Microbiome"; Science; May 29, 2009; pp. 1-7; vol. 324; No. 5931.
Griffen et al.; "CORE: A Phylogenetically-Curated 16S rDNA Database of the Core Oral Microbiome"; PLoS One; Apr. 2011; pp. 1-10; vol. 6; Issue 4.
Gueniche et al.; Bifidobacterium longum lysate, a new ingredient for reactive skin; Experimental Dermatology; bearing a date of Jun. 3, 2009; pp. 1-8; vol. 19; John Wiley & Sons A/S.
Guinane et al.; "Role of the gut microbiota in health and chronic gastrointestinal disease: understanding a hidden metabolic organ"; Therapeutic Advances in Gastroenterology; created on Apr. 16, 2014; pp. 295-308; vol. 6; No. 4; SAGEJournals.
Hagleitner et al.; "Smart single-chip gas sensor microsystem"; Nature; Nov. 15, 2001; pp. 293-296; vol. 414; Macmillan Magazines Ltd.
Hammami et al.; "BACTIBASE: a new web-accessible database for bacteriocin characterization"; BMC Microbiology; bearing a date of Oct. 17, 2007; 6 total pages; BioMed Central Ltd.
Hardy et al.; "Probiotics, Prebiotics and Immunomodulation of Gut Mucosal Defences: Homeostasis and Immunopathology"; Nutrients; bearing a date of Mar. 5, 2013; pp. 1869-1912; vol. 5.
Harz et al.; "Vibrational Spectroscopy—A Powerful Tool for the Rapid Identification of Microbial Cells at the Single-Cell Level"; Cytometry Part A Journal of the International Society for Advancement of Cytometry; 2009; created on Aug. 26, 2013; pp. 104-113; vol. 75A; International Society for Advancement of Cytometry.
Hayes, Tim; Next-Generation Cell Phone Cameras; OPN Optics & Photonics News; Feb. 2012; pp. 16-21.
Helm et al.; "Classification and identification of bacteria by Fourier-transform infrared spectroscopy"; Journal of General Microbiology; 1991; pp. 69-79; vol. 137; SGM; Printed in Great Britain.
Hemmerling et al.; "Phase 1 Dose-ranging Safety Trial of *Lactobacillus crispatus* CTV-05 (Lactin-V) for the Prevention of Bacterial Vaginosis"; Sex Transm Dis.; Sep. 2009; pp. 1-12; vol. 36; No. 9.
Hildebrand et al.; "Acoustic microscopy of living cells"; Proc. Natl. Acad. Sci.; Mar. 1981; pp. 1656-1660; vol. 78; No. 3.
Hilton, Peter J.; "Laser induced fluorescence imaging of bacteria"; SPIE; PDF created on Aug. 12, 2013; pp. 1174-1178; vol. 3491.
Hornyak, Tim; "RFID Powder"; Scientific American; Feb. 2008; pp. 68-71; Scientific American, Inc.
Huff et al.; "Light-scattering sensor for real-time identification of Vibrio parahaemolyticus, Vibrio vulnificus and Vibrio cholera colonies on solid agar plate"; Microbial Biotechnology; 2012; pp. 607-620; vol. 5, No. 5; The Authors; Microbial Biotechnology-Society for Applied Microbiology and Blackwell Publishing Ltd.
Ikanovic et al.; "Fluorescence Assay Based on Aptamer-Quantum Dot Binding to Bacillus Thuringiensis Spores"; J Fluoresc; 2007; pp. 193-199; vol. 17; Springer Science + Business Media, LLC.
Jaiswal et al.; "Long-term multiple color imaging of live cells using quantum dot biocoiljugates"; Nature Biotechnology; Jan. 2003; pp. 47-51; vol. 21; Nature Publishing Group; www.nature.com/naturebiotechnology.
Jhaveri et al.; "In vitro selection of signaling aptamers"; Nature Biotechnology; Dec. 2000; pp. 1293-1297; vol. 18; Nature America Inc.
Kashyap et al.; "Surface Plasmon Resonance-Based Fiber and Planar Waveguide Sensors"; Journal of Sensors; Accepted Jun. 26, 2009; pp. 1-9; vol. 2009; Hindawi Publishing Corporation.
Kim et al.; "Lens-Free Imaging for Biological Applications"; Journal of Laboratory Automation; Jan. 27, 2012; pp. 43-49; vol. 17; No. 1; Society for Laboratory Automation and Screening.
Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.
Koenig et al.; "Laser-Induced Autofluorescence for Medical Diagnosis"; Journal of Fluorescence; 1994; pp. 17-40; vol. 4; No. 1; Plenum Publishing Corporation.
Koo et al.; "Development of a Streptavidin-Conjugated Single-Chain Antibody That Binds Bacillus cereus Spores"; Applied and Environmental Microbiology; Jul. 1998; pp. 2497-2502; vol. 64; No. 7; American Society for Microbiology.
Korting et al.; "Differences in the Skin Surface pH and Bacterial Microflora Due to the Long-term Application of Synthetic Detergent Preparations of pH 5.5 and pH 7.0—Results of a Crossover Trial in Healthy Volunteers"; Sonderdruck aus Acta. Derm Venereol (Stockholm); bearing a date of Oct. 16, 1989; pp. 235-240.
Kumar et al.; "AnimalLectinDB: An integrated animal lectin database"; Bioinformation; published Apr. 22, 2011; pp. 134-136; vol. 6; No. 3; Biomedical Informatics.
Kumari et al.; "Effect of the Bacteriocin Produced by *Lactococcus lactis* Subsp. *lactis* CCSUB202, on Mode of Action of *Lactococcus lactis* Subsp. *lactis* MTCC3038"; bearing a date of Dec. 23, 2008; 5 total pages; International Journal of Probiotics and Prebiotics; vol. 4, No. 3; New Century Health Publishers, LLC.
Kupper et al.; "Generation of human antibody fragments against *Streptococcus* mutans using a phage display chain shuffling approach"; BMC Biotechnology; Jan. 25, 2005; pp. 1-12; vol. 5; No. 4; Kupper et al.
Lee et al.; "A micro-machined LC-resonator for high-frequency magnetic sensor applications"; Intermag 2006; Downloaded on Nov. 17, 2009; pp. 1.
Lee et al.; "Graphene-Based Chemiluminescence Resonance Energy Transfer for Homogeneous Immunoassay"; ACS NANO; 2012; pp. 2978-2983; vol. 6; No. 4; American Chemical Society.
Liu et al.; "Deep Sequencing of the Oral Microbiome Reveals Signatures of Periodontal Disease"; PLos One; Jun. 2012; pp. 1-16; vol. 7; Issue 6; Liu et al.
Low et al.; "A DNA Aptamer Recognizes the Asp f 1 Allergen of Aspergillus fumigatus"; Biochem Biophys Res Commun.; Aug. 28, 2009; pp. 544-548; vol. 386; No. 3; Elsevier Inc.
Majid et al.; "Integration of stereophotogrammetry and triangulation-based laser scanning system for precise mapping of craniofacial morphology"; The International Archives of the Photogrammetry, Remote Sensing and Spatial Information Sciences; 2008; pp. 805-812; vol. XXXVII; Part B5; Beijing.
Manafi, M.; "New developments in chromogenic and fluorogenic culture media"; International Journal of Food Microbiology; created on May 1, 2014; pp. 205-218; vol. 60; Elsevier Science B.V.
Manafi et al.; "Fluorogenic and Chromogenic Substrates Used in Bacterial Diagnostics"; Microbiological Reviews; Sep. 1991; pp. 335-348; vol. 55, No. 3; American Society for Microbiology.
Markiewicz et al.; "The Use of 3D Imaging Tools in Facial Plastic Surgery"; Facial Plast Surg Clin N Am; 2011; pp. 655-682; vol. 19; Elsevier Inc.

(56) References Cited

OTHER PUBLICATIONS

Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26; No. 5; IEEE Computer Society.

Martin et al.; Role of commensal and probiotic bacteria in human health: a focus on inflammatory bowel disease; Microbial Cell Factories; bearing a date of 2013; created on Feb. 14, 2014; pp. 1-11; BioMed Central Ltd.

Mason et al.; "Deep Sequencing Identifies Ethnicity-Specific Bacterial Signatures in the Oral Microbiome"; PLoS One; Oct. 2013; pp. 1-7; vol. 8; Issue 10.

Mastromarino et al.; "Bacterial vaginosis: a review on clinical trials with probiotics"; New Microbiologica; bearing a date of May 12, 2013; pp. 229-238; vol. 36.

Mateus et al.; "Adherence of Candida albicans to Silicone Induces Immediate Enhanced Tolerance to Fluconazole"; Antimicrobial Agents and Chemotherapy; Sep. 2004; pp. 3358-3366; vol. 48; No. 9; American Society for Microbiology.

Meerwaldt et al.; "Skin Autofluorescence, a Measure of Cumulative Metabolic Stress and Advanced Glycation End Products, Predicts Mortality in Hemodialysis Patients"; Journal of the American Society of Nephrology; 2005; pp. 3687-3693; vol. 16; American Society of Nephrology.

Modlin, Robert L.; "Innate Immunity: Ignored for decades, but not forgotten"; J Invest Dermatol.; Mar. 2012; pp. 882-886; vol. 132; No. 3.

Mohan et al.; "Bokode: Imperceptible Visual tags for Camera Based Interaction from a Distance"; PDF created on Aug. 12, 2013; pp. 1-8; http://cameraculture.media.mit.edu/bokode.

Mohanty et al.; "Micro Electrical Impedance Spectroscopy of Bovine Chromaffin Cells"; printed on Nov. 14, 2013; pp. 1-5.

Murakami et al.; "A miniature confocal optical microscope with mems gimbal scanner"; Transducers '03; The 12th International Conference on Solid State Sensors, Actuators and Microsystems, Boston, Jun. 8-12, 2003; pp. 587-590; IEEE.

Nakatsuji et al.; "Antibodies Elicited by Inactivated Propionibacterium acnes-Based Vaccines Exert Protective Immunity and Attenuate the IL-8 Production in Human Sebocytes: Relevance to Therapy for Acne Vulgaris"; Journal of Investigative Dermatology; published online May 8, 2008; pp. 2451-2457; vol. 128; The Society for Investigative Dermatology.

Nitsche et al.; "One-step selection of Vaccinia virus-binding DNA aptamers by MonoLEX"; BMC Biotechnology; published Aug. 15, 2007; pp. 1-12; vol. 7; No. 48; Nitsche et al.

Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.

Oh et al.; "Shifts in human skin and nares microbiota of healthy children and adults"; Genome Medicine; bearing a date of 2012; created on Apr. 16, 2014; pp. 1-11; vol. 4; Issue 77; BioMed Central.

Peppas et al.; "Polymers and Gels as Molecular Recognition Agents"; Pharmaceutical Research; May 2002; pp. 578-587; vol. 19; No. 5; Plenum Publishing Corporation.

Proske et al.; "Aptamers—basic research, drug development, and clinical applications"; Appl Microbiol Biotechnol; Published online Nov. 11, 2005; pp. 367-374; vol. 69; Springer-Verlag.

Quast et al.; "The SILVA ribosomal RNA gene database project: improved data processing and web-based tools"; Nucleic Acids Research; Published Nov. 28, 2012; pp. D590-D596; vol. 41; The Author(s) 2012; Oxford University Press.

Raghavan et al.; "BIAcore: a microchip based system for analyzing the formation of macromolecular complexes"; Structure; Apr. 15, 1995; pp. 351-333; vol. 3; No. 4; Current Biology Ltd.

Rucker et al.; "Functional Antibody Immobilization on 3-Dimensional Polymeric Surfaces Generated by Reactive Ion Etching"; Langmuir; In Final Form Jun. 2, 2005; pp. 7621-7625; vol. 21; American Chemical Society.

Schrezenmeir et al.; Probiotics, prebiotics, and synbiotics—approaching a definition; The American Journal of Clinical Nutrition; bearing a date of Jan. 14, 2014; pp. 361-364; American Society for Clinical Nutrition.

Savage et al.; "Urinary levels of triclosan and parabens are associated with aeroallergen and food sensitization"; J. Allergy Clin. Immunol.; Aug. 2012; pp. 1-19; vol. 130, No. 2; Mosby, Inc.

Sciarra et al.; Aerosols; Remington—The Science and Practice of Pharmacy; created on Mar. 3, 2014; pp. 1000-1017 (plus cover); Lipponcott Williams & Wilkins.

Seidl et al.; "Opto-mechanical combination of a line scanning camera and a micro laser scanner system"; PDF created on Aug. 12, 2013; pp. 1-6.

Selinuivimi et al.; "Software for quantification of labeled bacteria from digital microscope images by automated image analysis"; BioTechniques; Dec. 2005; pp. 859-863; vol. 39; No. 6.

Shetty et al.; "Opportunities and challenges for gut microbiome studies in the Indian population"; Microbiome; bearing a date of Apr. 9, 2013; pp. 1-12; vol. 1; Issue 24; BioMed Central Ltd.

Shimobaba et al.; "Gigapixel inline digital holographic microscopy using a consumer scanner"; Physics Optics; May 27, 2013; pp. 1-6; Optical Society of America.

Shu et al.; Fermentation of Propionibacterium acnes, a Commensal Bacterium in the Human Skin Microbiome, as Skin Probiotics against Methicillin-Resistant *Staphylococcus aureus*; PLoS One; Feb. 2013; pp. 1-11; vol. 8—Issue 2.

Smart et al.; "Microbiological spoilage in pharmaceuticals and cosmetics"; J. Soc. Cosmet. Chem.; bearing a date of Sep. 29, 1971; pp. 721-737; vol. 23; Society of Cosmetic Chemists of Great Britain.

Snow et al.; "Chemical Detection with a Single-Walled Carbon Nanotube Capacitor"; Science; Mar. 25, 2005; pp. 1942-1945; vol. 307; American Association for the Advancement of Science.

Son et al.; "An implantable wireless microdosimeter for radiation oncology"; MEMS 2008, Tucson, AZ, USA; Jan. 13-17, 2008; pp. 256-259; IEEE.

Spear et al.; "Isolation, characterization, and recovery of small peptide phage display epitopes selected against viable malignant glioma cells"; Cancer Gene Therapy; pp. 506-511; vol. 8, No. 7; Nature Publishing Group.

Sun et al.; "An Enhanced Active Shape Model for Facial Features Extraction"; 2008 11th IEEE International Conference on Communication Technology Proceedings; 2008; pp. 661-664; IEEE.

Sun et al.; "Broadband single cell impedance spectroscopy using maximum length sequences: theoretical analysis and practical considerations"; Measurement Science and Technology; 2007; pp. 2589-2868; vol. 18; IOP Publishing Ltd, UK.

Szeliski, Richard; "Image Alignment and Stitching: A Tutorial"; Computer Graphics and Vision; 2006; pp. 1-104; vol. 2; No. 1; R. Szeliski.

Tachon et al.; "Experimental conditions affect the site of tetrazolium violet reduction in the electron transport chain of Lactococcus lactis"; Microbiology; Accepted Jun. 7, 2009; pp. 2941-2948; vol. 155; SGM.

Terada et al.; "Bacterial adhesion to and viability on positively charged polymer surfaces"; Microbiology; Accepted on Aug. 22, 2006; pp. 3575-3583; vol. 152; SGM.

Ulicny, J.; "Lorenz-Mie Light Scattering in Cellular Biology"; Gen. Physiol. Biophys.; 1992; pp. 133-151; vol. 11.

Valm et al.; "Systems-level analysis of microbial community organization through combinatorial labeling and spectral imaging"; PNAS; Mar. 8, 2011; pp. 4152-4157; vol. 108; No. 10.

Van Heerbeek et al.; "Three dimensional measurement of rhinoplasty results"; Rhinology; 2009; pp. 121-125; vol. 47.

Vashist, Sandeep Kumar; "A Review of Microcantilevers for Sensing Applications"; AZojono Journal of Nanotechnology Online; Jun. 2007; pp. 1-15; vol. 3; AZoM.com Pty Ltd.

Wachi et al.; "Decomposition of surface-active agents by bacteria isolated from deionized water"; J. Soc. Cosmet. Chem.; Mar./Apr. 1980; pp. 67-84; vol. 31.

Yanagi et al.; "Assimilation of Selected Cosmetic Ingredients by Microorganisms"; J. Soc. Cosmet. Chem.; Dec. 9, 1971; pp. 851-865; vol. 22.

(56) References Cited

OTHER PUBLICATIONS

Yasuda et al.; "Lectin Microarray Reveals Binding Profiles of Lactobacillus casei Strains in a Comprehensive Analysis of Bacterial Cell Wall Polysaccharides"; Applied and Environmental Microbiology; Jul. 2011; pp. 4539-4546; vol. 77, No. 13; American Society for Microbiology.

Yatsunenko et al.; "Human gut microbiome viewed across age and geography"; Nature; bearing a date of Dec. 14, 2012; pp. 1-15; vol. 486; No. 7402.

Ye et al.; "Molecularly imprinted polymers as antibody and receptor mimics for assays, sensors and drug discovery"; Anal Bioanal Chem; Published online Jan. 22, 2004; pp. 1887-1897; vol. 378; Springer-Verlag.

Yusa et al.; "Controlled multiple quantum coherences of nuclear spins in a nanometre-scale device"; Nature; Apr. 21, 2005; pp. 1001-1005; vol. 434; Nature Publishing Group.

Zelada-Guillen et al.; "Immediate Detection of Living Bacteria at Ultralow Concentrations Using a Carbon Nanotube Based Potentiometric Aptasensor"; Angew. Chem. Int. Ed; 2009; pp. 1-4; vol. 48; Wiley-VCH Verlag GmbH & Co. KGaA; Weinheim.

Zharov et al.; "In vivo high-speed imaging of individual cells in fast blood flow"; Journal of Biomedical Optics; Sep./Oct. 2006; pp. 054034-1-054034-4; vol. 11; No. 5; SPIE.

Zharov et al.; "In vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zheng et al.; "Enhanced active shape model for facial feature localization"; Proceedings of the Seventh International Conference on Machine Learning and Cybernetics, Kunming; Jul. 12-15, 2008; pp. 2841-2845; IEEE.

Zitova et al.; "Image registration methods: a survey"; Image and Vision Computing; accepted Jun. 2003; pp. 977-1000; vol. 21; Elsevier B.V.

Ozalp et al.; "Antimicrobial aptamers for detection and inhibition of microbial pathogen growth"; Future Microbiology; Mar. 2013; pp. 387-401; vol. 8, No. 3; 1 page.

"Antibody Mimetic"; Wikipedia; Feb. 6, 2011; pp. 1-2; located at: http://en.wikipedia.org/wiki/Antibody_mimetic.

PCT International Search Report; International App. No. PCT/US2014/052081; dated Nov. 20, 2014; pp. 1-8.

PCT International Search Report; International App. No. PCT/US2014/052077; dated Nov. 28, 2014; pp. 1-4.

PCT International Search Report; International App. No. PCT/US2014/052086; dated Nov. 28, 2014; pp. 1-3.

PCT International Search Report; International App. No. PCT/US2014/051928; dated Dec. 1, 2014; pp. 1-3.

PCT International Search Report; International App. No. PCT/US2014/051934; dated Dec. 1, 2014; pp. 1-3.

European Patent Office, Supplementary European Search Report, Pursuant to Rule 62 EPC; App. No. EP 14838160; dated Mar. 27, 2017; pp. 1-9.

European Patent Office, Supplementary European Search Report, Pursuant to Rule 62 EPC; App. No. EP 14838524; dated Apr. 3, 2017; pp. 1-11.

European Patent Office, Supplementary European Search Report, Pursuant to Rule 62 EPC; App. No. EP 14838438; dated Nov. 10, 2017; pp. 1-11.

\* cited by examiner

FIG. 1

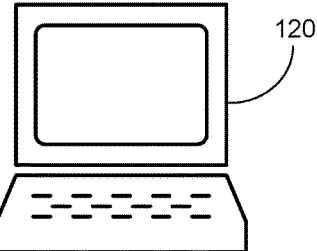

100

110
Ingredient-Microbe Interaction Dataset

120

130 Circuitry

140
Circuitry configured to receive information associated with a microbe profile of an individual, the microbe profile including a distribution of one or more types of microbes on a skin surface of the individual

150
Circuitry configured to receive information associated with an ingredient list of the cosmetic product, the ingredient list including one or more cosmetic ingredients

160
Circuitry configured to compare the received information associated with the microbe profile of the individual and the received information associated with the ingredient list of the cosmetic product to the ingredient-microbe interaction dataset

170
Circuitry configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients

180
Circuitry configured to recommend a modification to the ingredient list of the cosmetic product in response to the identified interaction

190
Circuitry configured to report to a user the recommended modification to the ingredient list of the cosmetic product

110 Ingredient-Microbe Interaction Dataset

200 One or more reference cosmetic ingredients

205 One or more of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax 210 One or more probiotic agents, one or more prebiotic agents, or one or more therapeutic agents

215 One or more types of reference microbes

220 One or more types of skin-associated microbes

225 Information associated with the interactions between the one or more reference cosmetic ingredients and the one or more types of reference microbes

230 Information associated with the potential effect on the one or more reference cosmetic ingredients in response to the one or more types of reference microbes 235 Information associated with a potential color effect on the one or more reference cosmetic ingredients in response to the one or more types of reference microbes 240 Information associated with a potential texture effect on the one or more reference cosmetic ingredients in response to the one or more types of reference microbes 245 Information associated with a potential pH effect on the one or more reference cosmetic ingredients in response to the one or more types of reference microbes 250 Information associated with a potential odor effect on the one or more reference cosmetic ingredients in response to the one or more types of reference microbes 255 Ingredient-microbe interaction dataset is incorporated into a memory component of the computing device 260 Ingredient-microbe interaction dataset is stored on a portable data storage device 265 Ingredient-microbe interaction dataset is stored on a remote computing device 270 Ingredient-microbe interaction dataset is updatable

120

130 Circuitry

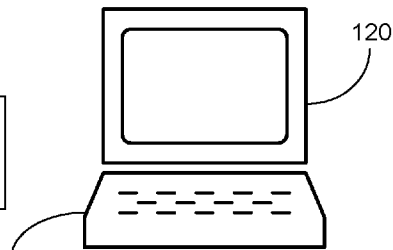
120

110
Ingredient-Microbe
Interaction Dataset

130 Circuitry

140 Circuitry configured to receive information associated with a microbe profile of an individual, the microbe profile including a distribution of one or more types of microbes on a skin surface of the individual

400 Circuitry configured to receive the information associated with the microbe profile of the individual from a microbe profiling device

420 Circuitry configured to receive the information associated with the microbe profile of the individual from a computing component associated with at least one of a microbe profiling device or a microbe profiling system

410 Circuitry configured to receive the information associated with the microbe profile of the individual from a microbe profiling system

430 Circuitry configured to receive the information associated with the microbe profile of the individual from a portable data storage device

440 Circuitry configured to receive the information associated with the microbe profile of the individual from the Internet

150 Circuitry configured to receive information associated with an ingredient list of the cosmetic product, the ingredient list including one or more cosmetic ingredients

160 Circuitry configured to compare the received information associated with the microbe profile of the individual and the received information associated with the ingredient list of the cosmetic product to the ingredient-microbe interaction dataset

170 Circuitry configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients

180 Circuitry configured to recommend a modification to the ingredient list of the cosmetic product in response to the identified interaction

190 Circuitry configured to report to a user the recommended modification to the ingredient list of the cosmetic product

500 Ingredient List

510 Ingredient list of the cosmetic product includes at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax 520 Ingredient list of the cosmetic product includes one or more probiotic agents, one or more prebiotic agents, or one or more therapeutic agents 530 Ingredient list of the cosmetic product is stored in at least one of a memory component of the computing device, a portable data storage device, or a remote server

110 Ingredient-Microbe Interaction Dataset

120

130 Circuitry

140

150 Circuitry configured to receive information associated with an ingredient list of the cosmetic product, the ingredient list including one or more ingredients 540 Circuitry configured to receive the information associated with the ingredient list of the cosmetic product from a remote computing device 550 Circuitry configured to receive the information associated with the ingredient list of the cosmetic product from at least one of a cosmetic distributer, a cosmetic manufacturer, or a cosmetic formulary 560 Circuitry configured to receive the information associated with the ingredient list of the cosmetic product from a portable data storage device 570 Circuitry configured to receive the information associated with the ingredient list of the cosmetic product from the Internet

110
Ingredient-Microbe Interaction Dataset

600
Scanning Device

130 Circuitry

140
Circuitry configured to receive information associated with a microbe profile of an individual, the microbe profile including a distribution of one or more types of microbes on a skin surface of the individual

150
Circuitry configured to receive information associated with an ingredient list of the cosmetic product, the ingredient list including one or more cosmetic ingredients

610
Circuitry configured to receive information associated with the ingredient list of the cosmetic product from a scanning device

160
Circuitry configured to compare the received information associated with the microbe profile of the individual and the received information associated with the ingredient list of the cosmetic product to the ingredient-microbe interaction dataset

170
Circuitry configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients

180
Circuitry configured to recommend a modification to the ingredient list of the cosmetic product in response to the identified interaction

190
Circuitry configured to report to a user the recommended modification to the ingredient list of the cosmetic product

FIG. 7

100

120

| 110<br>Ingredient-Microbe<br>Interaction Dataset |

130 Circuitry

140

150

160 Circuitry configured to compare the received information associated with the microbe profile of the individual and the received information associated with the ingredient list of the cosmetic product to the ingredient-microbe interaction dataset 700 Circuitry configured to compare the one or more types of microbes in the microbe profile of the individual to the one or more types of reference microbes in the ingredient-microbe interaction dataset 710 Circuitry configured to compare the one or more cosmetic ingredients in the ingredient list of the cosmetic product to the one or more reference cosmetic ingredients in the ingredient-microbe interaction dataset 170 Circuitry configured to identify an interaction between least one of the one or more ingredients in the cosmetic product and at least one of the one or more types of microbes in the microbe profile of the individual, wherein the interaction has a potential effect on the at least one of the one or more ingredients in the cosmetic product 720 Circuitry configured to identify the potential effect on the at least one of the one or more cosmetic ingredients in the ingredient list of the cosmetic product in response to at least one of the one or more types of microbes in the microbe profile of the individual 730 Circuitry configured to identify a potential color effect on the at least one of the one or more cosmetic ingredients in the ingredient list of the cosmetic product in response to at least one of the one or more types of microbes in the microbe profile of the individual 740 Circuitry configured to identify a potential texture effect on the at least one of the one or more cosmetic ingredients in the ingredient list of the cosmetic product in response to at least one of the one or more types of microbes in the microbe profile of the individual 750 Circuitry configured to identify a potential pH effect on the at least one of the one or more cosmetic ingredients in the ingredient list of the cosmetic product in response to at least one of the one or more types of microbes in the microbe profile of the individual 760 Circuitry configured to identify a potential odor effect on the at least one of the one or more cosmetic ingredients in the ingredient list of the cosmetic product in response to at least one of the one or more types of microbes in the microbe profile of the individual

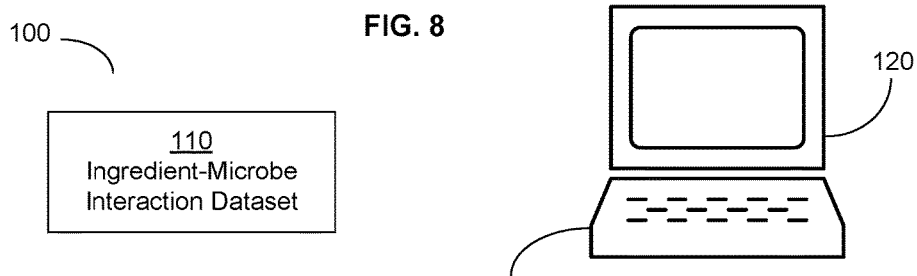

100

110
Ingredient-Microbe
Interaction Dataset

120

130 Circuitry

140 Circuitry configured to receive information associated with a microbe profile of an individual, the microbe profile including a distribution of one or more types of microbes on a skin surface of the individual 150 Circuitry configured to receive information associated with an ingredient list of the cosmetic product, the ingredient list including one or more cosmetic ingredients 160 Circuitry configured to compare the received information associated with the microbe profile of the individual and the received information associated with the ingredient list of the cosmetic product to the ingredient-microbe interaction dataset 170 Circuitry configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients 180 Circuitry configured to recommend a modification to the ingredient list of the cosmetic product in response to the identified interaction 800 Circuitry configured to recommend a modification to the ingredient list of the cosmetic product to alleviate the identified interaction 810 Circuitry configured to recommend a modification to the ingredient list of the cosmetic product to enhance the identified interaction 820 Circuitry configured to recommend an addition of at least one cosmetic ingredient to the ingredient list of the cosmetic product 830 Circuitry configured to recommend a subtraction of at least one cosmetic ingredient from the ingredient list of the cosmetic product 840 Circuitry configured to recommend a relative change in the concentration of at least one cosmetic ingredient in the ingredient list of the cosmetic product 190 Circuitry configured to report to a user the recommended modification to the ingredient list of the cosmetic product

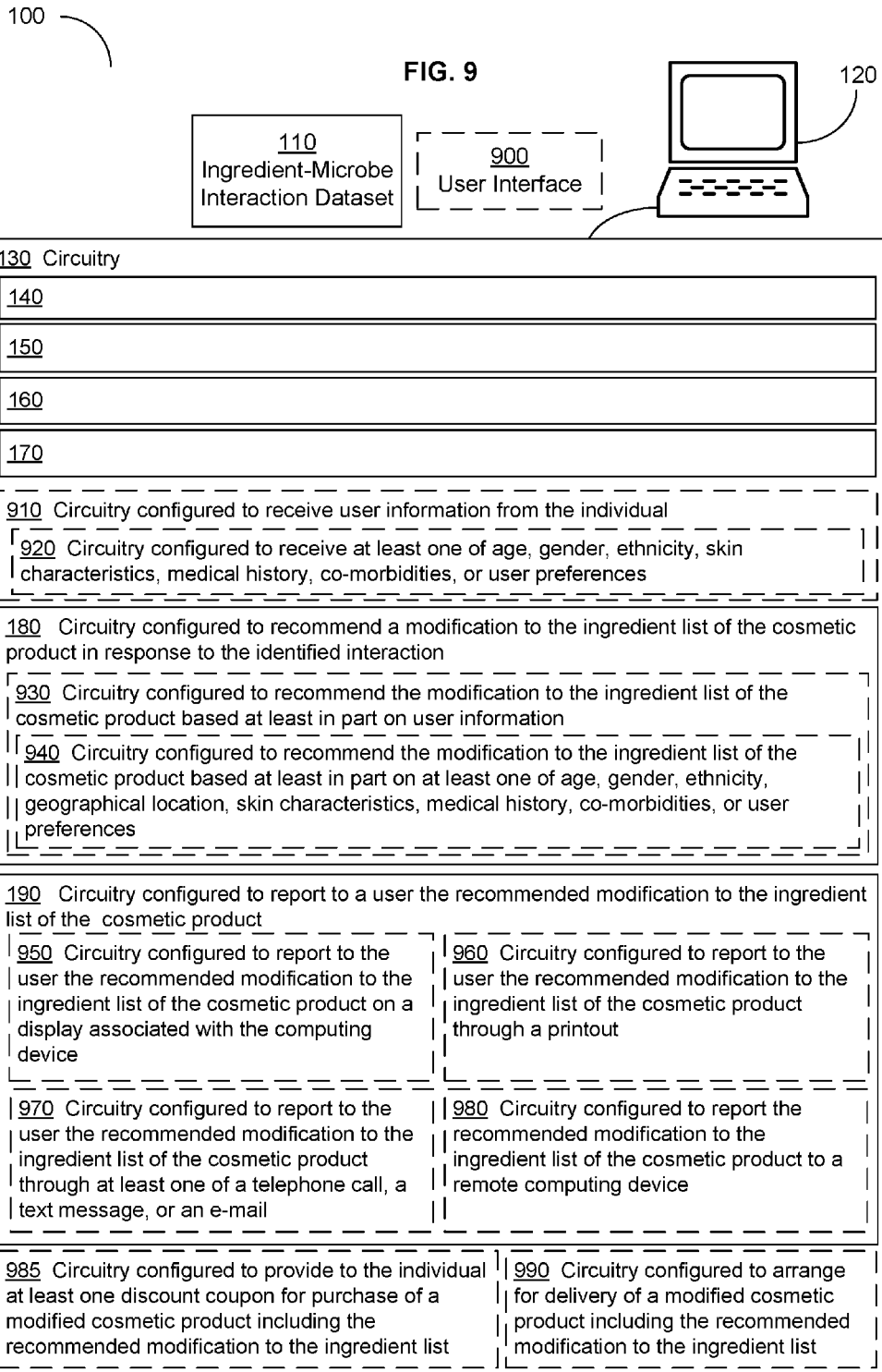

FIG. 10

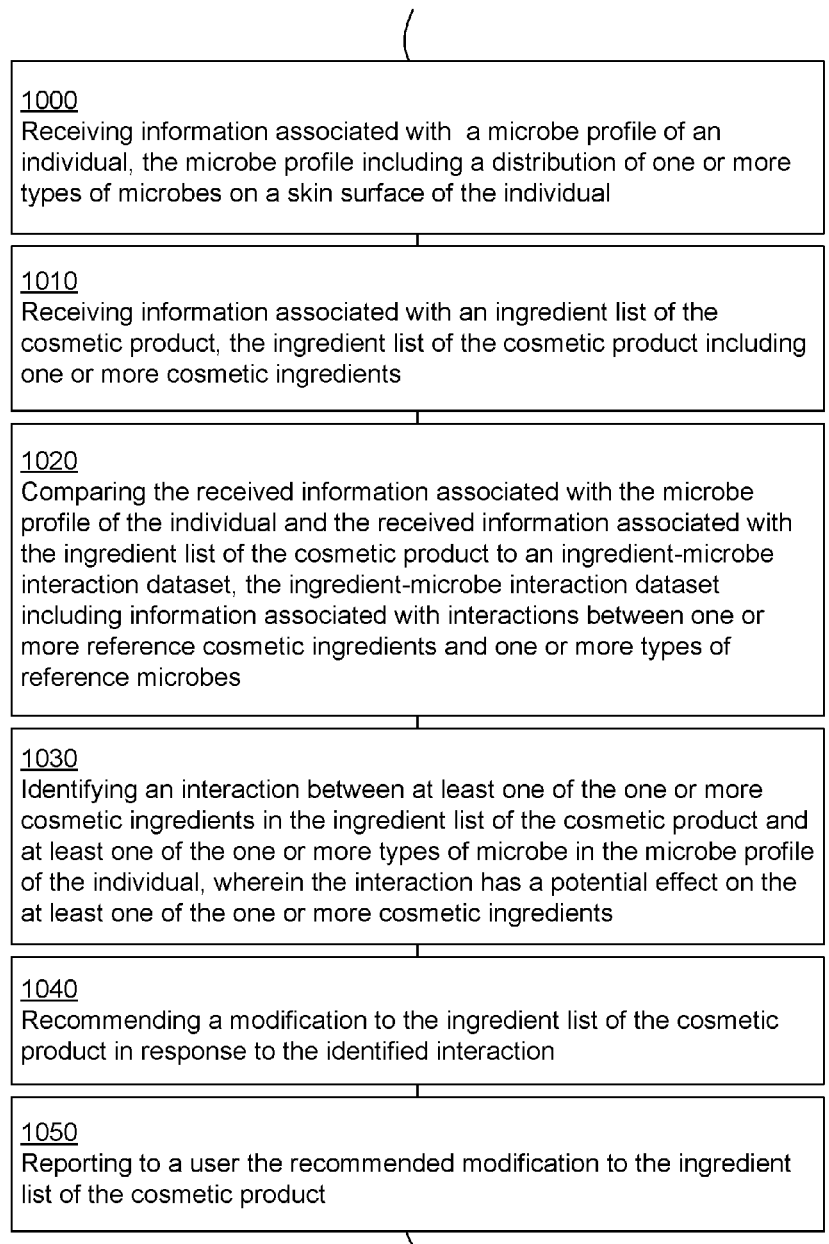

1000
Receiving information associated with a microbe profile of an individual, the microbe profile including a distribution of one or more types of microbes on a skin surface of the individual 1010
Receiving information associated with an ingredient list of the cosmetic product, the ingredient list of the cosmetic product including one or more cosmetic ingredients 1020
Comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes 1030
Identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients 1040
Recommending a modification to the ingredient list of the cosmetic product in response to the identified interaction 1050
Reporting to a user the recommended modification to the ingredient list of the cosmetic product

FIG. 11

1000 Receiving information associated with a microbe profile of an individual, the microbe profile including a distribution of one or more types of microbes on a skin surface of the individual 1100 Receiving the information associated with the microbe profile of the individual from a microbe profiling device 1110 Receiving the information associated with the microbe profile of the individual from a microbe profiling system 1120 Receiving the information associated with the microbe profile of the individual from a computing component associated with at least one of a microbe profiling device or a microbe profiling system 1130 Receiving the information associated with the microbe profile of the individual from a portable data storage device 1140 Receiving the information associated with the microbe profile of the individual from at least one of a remote computing device, a remote server, or the Internet 1010 Receiving information associated with an ingredient list of the cosmetic product, the ingredient list of the cosmetic product including one or more cosmetic ingredients 1020 Comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes 1030 Identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients 1040 Recommending a modification to the ingredient list of the cosmetic product in response to the identified interaction 1050 Reporting to a user the recommended modification to the ingredient list of the cosmetic product

FIG. 12

1000 Receiving information associated with a microbe profile of an individual, the microbe profile including a distribution of one or more types of microbes on a skin surface of the individual

1010 Receiving information associated with an ingredient list of the cosmetic product, the ingredient list of the cosmetic product including one or more cosmetic ingredients > 1200 Receiving information associated with the one or more cosmetic ingredients in the ingredient list of the cosmetic product
>
>> 1210 Receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax in the ingredient list of the cosmetic product
>>
>> 1220 Receiving information associated with at least one of one or more probiotic agents, one or more prebiotic agents, or one or more therapeutic agents in the ingredient list of the cosmetic product
>
> 1230 Receiving the information associated with the ingredient list of the cosmetic product from a remote source
>
> 1240 Receiving the information associated with the ingredient list of the cosmetic product from a cosmetic distributer, a cosmetic manufacturer, or a cosmetic formulary
>
> 1250 Receiving the information associated with the ingredient list of the cosmetic product from a portable data storage device
>
> 1260 Receiving the information associated with the ingredient list of the cosmetic product from a scanning device

1020 Comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes

1030 Identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients

1040 Recommending a modification to the ingredient list of the cosmetic product in response to the identified interaction

1050 Reporting to a user the recommended modification to the ingredient list of the cosmetic product

FIG. 13

| 1000 Receiving information associated with a microbe profile of an individual, the microbe profile including a distribution of one or more types of microbes on a skin surface of the individual |
|---|
| 1010 Receiving information associated with an ingredient list of the cosmetic product, the ingredient list of the cosmetic product including one or more cosmetic ingredients |
| 1020 Comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes |
|    1300 Comparing the one or more types of microbes in the microbe profile of the individual to the one or more types of reference microbes in the ingredient-microbe interaction dataset |
|    1310 Comparing the one or more cosmetic ingredients in the ingredient list of the cosmetic product to the one or more reference cosmetic ingredients in the ingredient-microbe interaction dataset |
| 1030 Identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients |
|    1320 Identifying the potential effect on the at least one of the one or more cosmetic ingredients in the ingredient list of the cosmetic product in response to at least one of the one or more types of microbes in the microbe profile of the individual |
|       1330 Identifying a potential color effect on the at least one of the one or more cosmetic ingredients in the ingredient list of the cosmetic product |
|       1340 Identifying a potential texture effect on the at least one of the one or more cosmetic ingredients in the ingredient list of the cosmetic product |
|       1350 Identifying a potential pH effect on the at least one of the one or more cosmetic ingredients in the ingredient list of the cosmetic product |
|       1360 Identifying a potential odor effect on the at least one of the one or more cosmetic ingredients in the ingredient list of the cosmetic product |
| 1040 Recommending a modification to the ingredient list of the cosmetic product in response to the identified interaction |
| 1050 Reporting to a user the recommended modification to the ingredient list of the cosmetic product |

FIG. 14

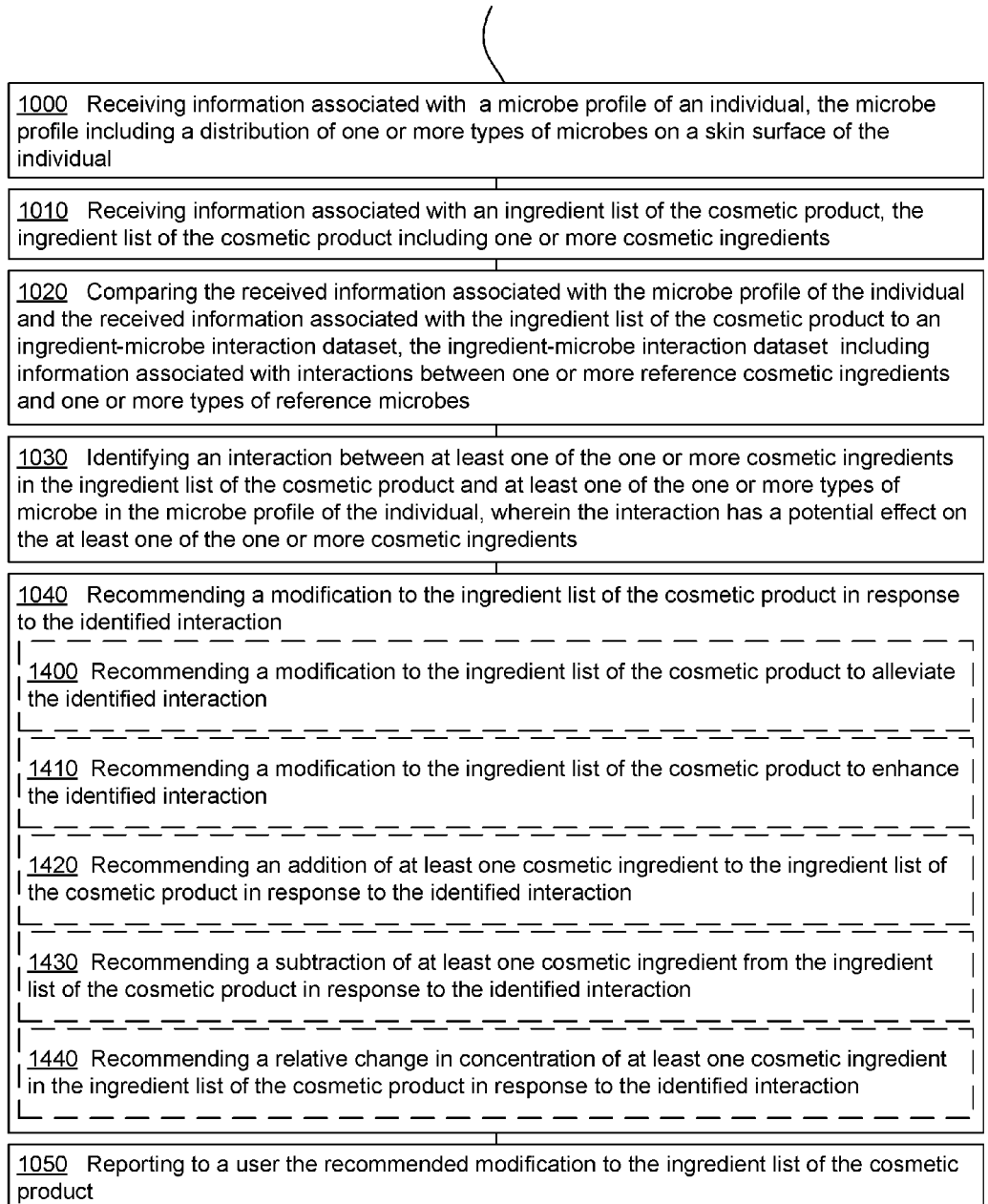

1000  Receiving information associated with a microbe profile of an individual, the microbe profile including a distribution of one or more types of microbes on a skin surface of the individual 1010  Receiving information associated with an ingredient list of the cosmetic product, the ingredient list of the cosmetic product including one or more cosmetic ingredients 1020  Comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes 1030  Identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients 1040  Recommending a modification to the ingredient list of the cosmetic product in response to the identified interaction 1400  Recommending a modification to the ingredient list of the cosmetic product to alleviate the identified interaction 1410  Recommending a modification to the ingredient list of the cosmetic product to enhance the identified interaction 1420  Recommending an addition of at least one cosmetic ingredient to the ingredient list of the cosmetic product in response to the identified interaction 1430  Recommending a subtraction of at least one cosmetic ingredient from the ingredient list of the cosmetic product in response to the identified interaction 1440  Recommending a relative change in concentration of at least one cosmetic ingredient in the ingredient list of the cosmetic product in response to the identified interaction 1050  Reporting to a user the recommended modification to the ingredient list of the cosmetic product

1610 Circuitry

1620
Circuitry for receiving information associated with a microbe profile of an individual, the microbe profile including a distribution of one or more types of microbes on a skin surface of the individual

1630
Circuitry for receiving information associated with an ingredient list of the cosmetic product, the ingredient list of the cosmetic product including one or more cosmetic ingredients

1640
Circuitry for comparing the received information associated with the microbe profile of the individual and the received information associated with the ingredient list of the cosmetic product with an ingredient-microbe interaction dataset, the ingredient-microbe interaction dataset including information associated with interactions between one or more reference cosmetic ingredients and one or more types of reference microbes

1650
Circuitry for identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients

1660
Circuitry for recommending a modification to the ingredient list of the cosmetic product in response to the identified interaction

1670
Circuitry for sending a signal to report to a user the recommended modification to the ingredient list of the cosmetic product

FIG. 17

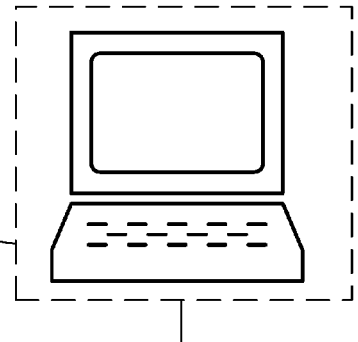

1600

1700

1610 Circuitry

1620
Circuitry for receiving information associated with a microbe profile of an individual, the microbe profile including a distribution of one or more types of microbes on a skin surface of the individual

1630
Circuitry for receiving information associated with an ingredient list of the cosmetic product, the ingredient list of the cosmetic product including one or more cosmetic ingredients

1640
Circuitry for comparing the received information associated with the microbe profile of the individual and the received information associated with the ingredient list of the cosmetic product with an ingredient-microbe interaction dataset, the ingredient-microbe interaction dataset including information associated with interactions between one or more reference cosmetic ingredients and one or more types of reference microbes

1650
Circuitry for identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients

1660
Circuitry for recommending a modification to the ingredient list of the cosmetic product in response to the identified interaction

1670
Circuitry for sending a signal to report to a user the recommended modification to the ingredient list of the cosmetic product

FIG. 18

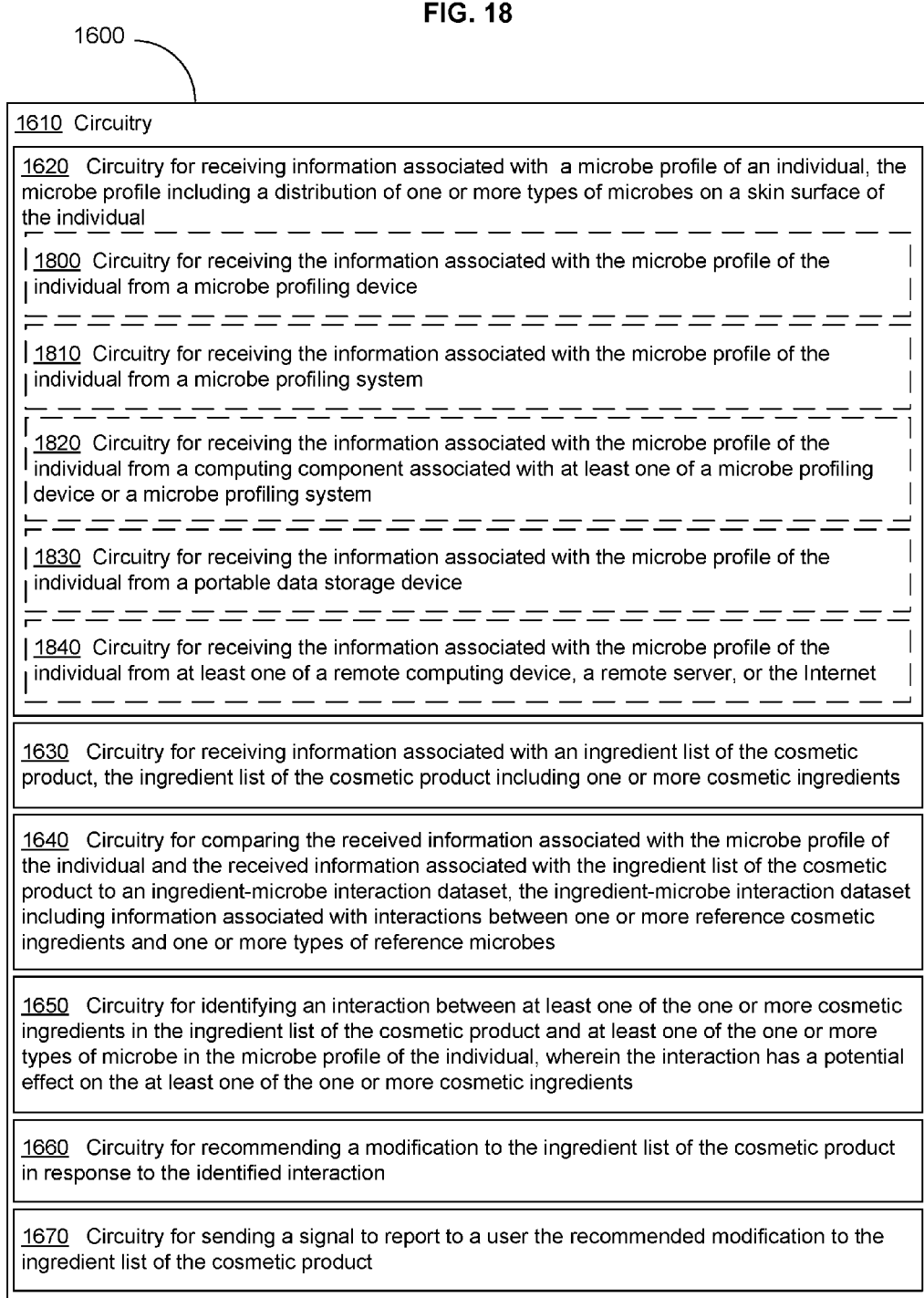

1600

1610 Circuitry

1620 Circuitry for receiving information associated with a microbe profile of an individual, the microbe profile including a distribution of one or more types of microbes on a skin surface of the individual

| 1800 Circuitry for receiving the information associated with the microbe profile of the individual from a microbe profiling device

| 1810 Circuitry for receiving the information associated with the microbe profile of the individual from a microbe profiling system

| 1820 Circuitry for receiving the information associated with the microbe profile of the individual from a computing component associated with at least one of a microbe profiling device or a microbe profiling system

| 1830 Circuitry for receiving the information associated with the microbe profile of the individual from a portable data storage device

| 1840 Circuitry for receiving the information associated with the microbe profile of the individual from at least one of a remote computing device, a remote server, or the Internet 1630 Circuitry for receiving information associated with an ingredient list of the cosmetic product, the ingredient list of the cosmetic product including one or more cosmetic ingredients 1640 Circuitry for comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes 1650 Circuitry for identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients 1660 Circuitry for recommending a modification to the ingredient list of the cosmetic product in response to the identified interaction 1670 Circuitry for sending a signal to report to a user the recommended modification to the ingredient list of the cosmetic product

| 1610 Circuitry |
|---|
| 1620 Circuitry for receiving information associated with a microbe profile of an individual, the microbe profile including a distribution of one or more types of microbes on a skin surface of the individual |
| 1630 Circuitry for receiving information associated with an ingredient list of the cosmetic product, the ingredient list of the cosmetic product including one or more cosmetic ingredients |
|    1900 Circuitry for receiving information associated with the one or more ingredients in the ingredient list of the cosmetic product |
|       1910 Circuitry for receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax |
|       1920 Circuitry for receiving information associated with one or more probiotic agents, one or more prebiotic agents, or one or more therapeutic agents |
|    1930 Circuitry for receiving the information associated with the ingredient list of the cosmetic product from a remote source |
|    1940 Circuitry for receiving the information associated with the ingredient list of the cosmetic product from a cosmetic distributer, a cosmetic manufacturer, or a cosmetic formulary |
|    1950 Circuitry for receiving the information associated with the ingredient list of the cosmetic product from a portable data storage device       1960 Circuitry for receiving the information associated with the ingredient list of the cosmetic product from a scanning device |
| 1640 Circuitry for comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes |
| 1650 Circuitry for identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients |
| 1660 Circuitry for recommending a modification to the ingredient list of the cosmetic product in response to the identified interaction |
| 1670 Circuitry for sending a signal to report to a user the recommended modification to the ingredient list of the cosmetic product |

1600 — FIG. 20

| 1610 Circuitry |
|---|
| 1620 Circuitry for receiving information associated with a microbe profile of an individual, the microbe profile including a distribution of one or more types of microbes on a skin surface of the individual |
| 1630 Circuitry for receiving information associated with an ingredient list of the cosmetic product, the ingredient list of the cosmetic product including one or more cosmetic ingredients |
| 1640 Circuitry for comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes |
|    2000 Circuitry for comparing the one or more types of microbes in the microbe profile of the individual to the one or more types of reference microbes in the ingredient-microbe interaction dataset |
|    2010 Circuitry for comparing the one or more cosmetic ingredients in the ingredient list of the cosmetic product to the one or more reference cosmetic ingredients in the ingredient-microbe interaction dataset |
| 1650 Circuitry for identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients |
|    2020 Circuitry for identifying the potential effect on the at least one of the one or more cosmetic ingredients in the ingredient list of the cosmetic product in response to at least one of the one or more types of microbes in the microbe profile of the individual |
|       2030 Circuitry for identifying a potential color effect on the at least one of the one or more cosmetic ingredients in the ingredient list of the cosmetic product |
|       2040 Circuitry for identifying a potential texture effect on the at least one of the one or more cosmetic ingredients in the ingredient list of the cosmetic product |
|       2050 Circuitry for identifying a potential pH effect on the at least one of the one or more cosmetic ingredients in the ingredient list of the cosmetic product |
|       2060 Circuitry for identifying a potential odor effect on the at least one of the one or more cosmetic ingredients in the ingredient list of the cosmetic product |
| 1660 Circuitry for recommending a modification to the ingredient list of the cosmetic product in response to the identified interaction |
| 1670 Circuitry for sending a signal to report to a user the recommended modification to the ingredient list of the cosmetic product |

1610 Circuitry

1620 Circuitry for receiving information associated with a microbe profile of an individual, the microbe profile including a distribution of one or more types of microbes on a skin surface of the individual

1630 Circuitry for receiving information associated with an ingredient list of the cosmetic product, the ingredient list of the cosmetic product including one or more cosmetic ingredients

1640 Circuitry for comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes

1650 Circuitry for identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients

1660 Circuitry for recommending a modification to the ingredient list of the cosmetic product in response to the identified interaction

| 2100 Circuitry for recommending a modification to the ingredient list of the cosmetic product to alleviate the identified interaction

| 2110 Circuitry for recommending a modification to the ingredient list of the cosmetic product to enhance the identified interaction

| 2120 Circuitry for recommending an addition of at least one cosmetic ingredient to the ingredient list of the cosmetic product in response to the identified interaction

| 2130 Circuitry for recommending a subtraction of at least one cosmetic ingredient from the ingredient list of the cosmetic product in response to the identified interaction

| 2140 Circuitry for recommending a relative change in concentration of at least one cosmetic ingredient in the ingredient list of the cosmetic product in response to the identified interaction

1670 Circuitry for sending a signal to report to a user the recommended modification to the ingredient list of the cosmetic product

1600 ⟶ FIG. 22

| |
|---|
| 1610 Circuitry |
| 1620 Circuitry for receiving information associated with a microbe profile of an individual, the microbe profile including a distribution of one or more types of microbes on a skin surface of the individual |
| 1630 Circuitry for receiving information associated with an ingredient list of the cosmetic product, the ingredient list of the cosmetic product including one or more cosmetic ingredients |
| 1640 Circuitry for comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes |
| 1650 Circuitry for identifying an interaction between at least one of the one or more cosmetic ingredients in the ingredient list of the cosmetic product and at least one of the one or more types of microbe in the microbe profile of the individual, wherein the interaction has a potential effect on the at least one of the one or more cosmetic ingredients |
| 2200 Circuitry for receiving user information from the individual |
|    2210 Circuitry for receiving at least one of age, gender, ethnicity, geographical location, skin characteristics, medical history, co-morbidities, or user preferences |
| 1660 Circuitry for recommending a modification to the ingredient list of the cosmetic product in response to the identified interaction |
|    2220 Circuitry for recommending the modification to the ingredient list of the cosmetic product based at least in part on user information |
|       2230 Circuitry for recommending the modification to the ingredient list of the cosmetic product based at least in part on at least one of age, gender, ethnicity, geographical location, skin characteristics, medical history, co-morbidities, or user preferences |
| 1670 Circuitry for sending a signal to report to a user the recommended modification to the ingredient list of the cosmetic product |
| 2240 Circuitry for sending a signal to report to the user the recommended modification to the ingredient list of the cosmetic product on a display associated with a computing device | 2260 Circuitry for sending a signal to report to the user the recommended modification to the ingredient list of the cosmetic product through at least one of a telephone call, a text message, or an e-mail |
| 2250 Circuitry for sending a signal to report to the user the recommended modification to the ingredient list of the cosmetic product through a printout. | 2270 Circuitry for sending a signal to report the recommended modification to the ingredient list of the cosmetic product to a computing device |
| 2280 Providing to the individual at least one discount coupon for purchase of a modified cosmetic product including the recommended modification to the ingredient list |
| 2290 Arranging for delivery of a modified cosmetic product including the recommended modification to the ingredient list |

FIG. 25

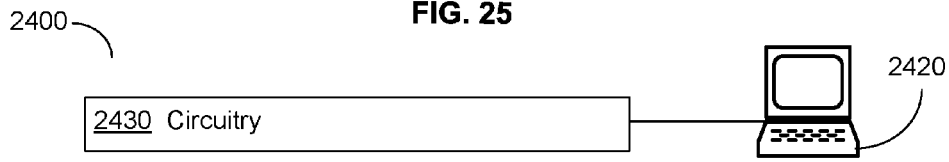

2400

2430 Circuitry

2420

2410 Ingredient-Microbe Interaction Dataset

2500 One or more reference cosmetic ingredients

2505 One or more of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax 2510 One or more probiotic agents, one or more prebiotic agents, or one or more therapeutic agents 2515 One or more types of reference microbes 2520 One or more types of skin-associated microbes 2525 Information associated with the interactions between the one or more reference cosmetic ingredients and the one or more types of reference microbes 2530 Information associated with a potential effect on the one or more types of reference microbes in response to the one or more reference cosmetic ingredients 2535 Information associated with a potential growth promoting effect on the one or more types of reference microbes in response to the one or more reference cosmetic ingredients 2540 Information associated with a potential growth inhibiting effect on the one or more types of reference microbes in response to the one or more reference cosmetic ingredients 2545 Information associated with a potential biofilm formation effect on the one or more types of reference microbes in response to the one or more reference cosmetic ingredients 2550 Ingredient-microbe interaction dataset is incorporated into a memory component of the computing device 2555 Ingredient-microbe interaction dataset is stored on a portable data storage device 2560 Ingredient-microbe interaction dataset is stored on a remote computing device 2565 Ingredient-microbe interaction dataset is updatable

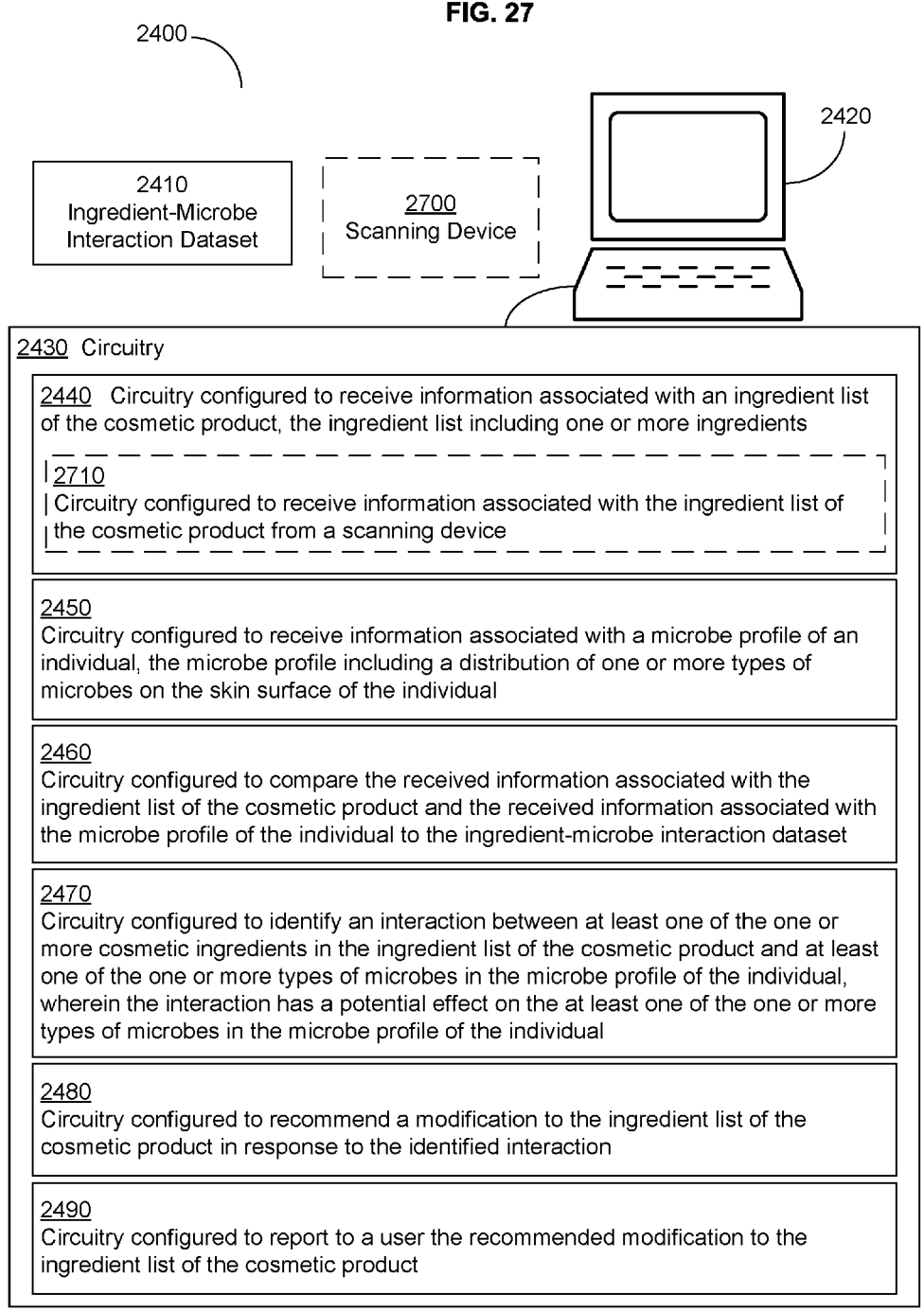

FIG. 28

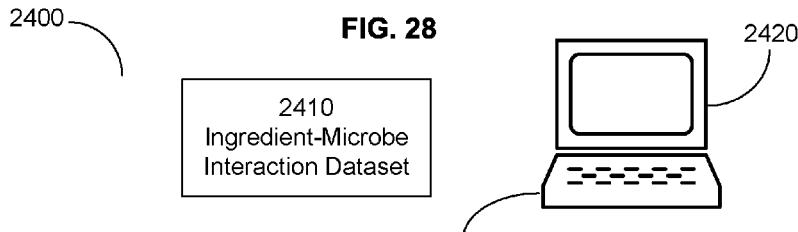

2400

2410 Ingredient-Microbe Interaction Dataset

2420

2430 Circuitry

2440 Circuitry configured to receive information associated with an ingredient list of the cosmetic product, the ingredient list including one or more cosmetic ingredients 2450 Circuitry configured to receive information associated with a microbe profile of an individual, the microbe profile including a distribution of one or more types of microbes on the skin surface of the individual 2800 Circuitry configured to receive the information associated with the microbe profile of the individual from a microbe profiling device 2820 Circuitry configured to receive the information associated with the microbe profile of the individual from a computing component associated with at least one of a microbe profiling device or a microbe profiling system 2810 Circuitry configured to receive the information associated with the microbe profile of the individual from a microbe profiling system 2830 Circuitry configured to receive the information associated with the microbe profile of the individual from a portable data storage device 2840 Circuitry configured to receive the information associated with the microbe profile of the individual from the Internet 2460 Circuitry configured to compare the received information associated with the ingredient list of the cosmetic product and the received information associated with the microbe profile of the individual to the ingredient-microbe interaction dataset 2470 Circuitry configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual 2480 Circuitry configured to recommend a modification to the ingredient list of the cosmetic product in response to the identified interaction 2490 Circuitry configured to report to a user the recommended modification to the ingredient list of the cosmetic product

FIG. 30

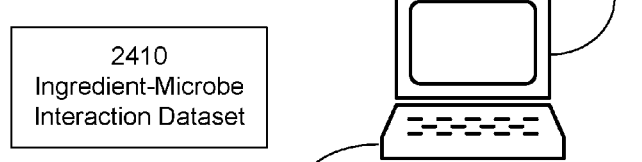

2400

2410 Ingredient-Microbe Interaction Dataset

2420

2430 Circuitry

2440 Circuitry configured to receive information associated with an ingredient list of the cosmetic product, the ingredient list including one or more cosmetic ingredients 2450 Circuitry configured to receive information associated with a microbe profile of an individual, the microbe profile including a distribution of one or more types of microbes on the skin surface of the individual 2460 Circuitry configured to compare the received information associated with the ingredient list of the cosmetic product and the received information associated with the microbe profile of the individual to the ingredient-microbe interaction dataset 2470 Circuitry configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual 2480 Circuitry configured to recommend a modification to the ingredient list of the cosmetic product in response to the identified interaction 3000 Circuitry configured to recommend a modification to the ingredient list of the cosmetic product to alleviate the identified interaction 3010 Circuitry configured to recommend a modification to the ingredient list of the cosmetic product to enhance the identified interaction 3020 Circuitry configured to recommend an addition of at least one cosmetic ingredient to the ingredient list of the cosmetic product 3030 Circuitry configured to recommend a subtraction of at least one cosmetic ingredient from the ingredient list of the cosmetic product 3040 Circuitry configured to recommend a relative change in the concentration of at least one cosmetic ingredient in the ingredient list of the cosmetic product 2490 Circuitry configured to report to a user the recommended modification to the ingredient list of the cosmetic product

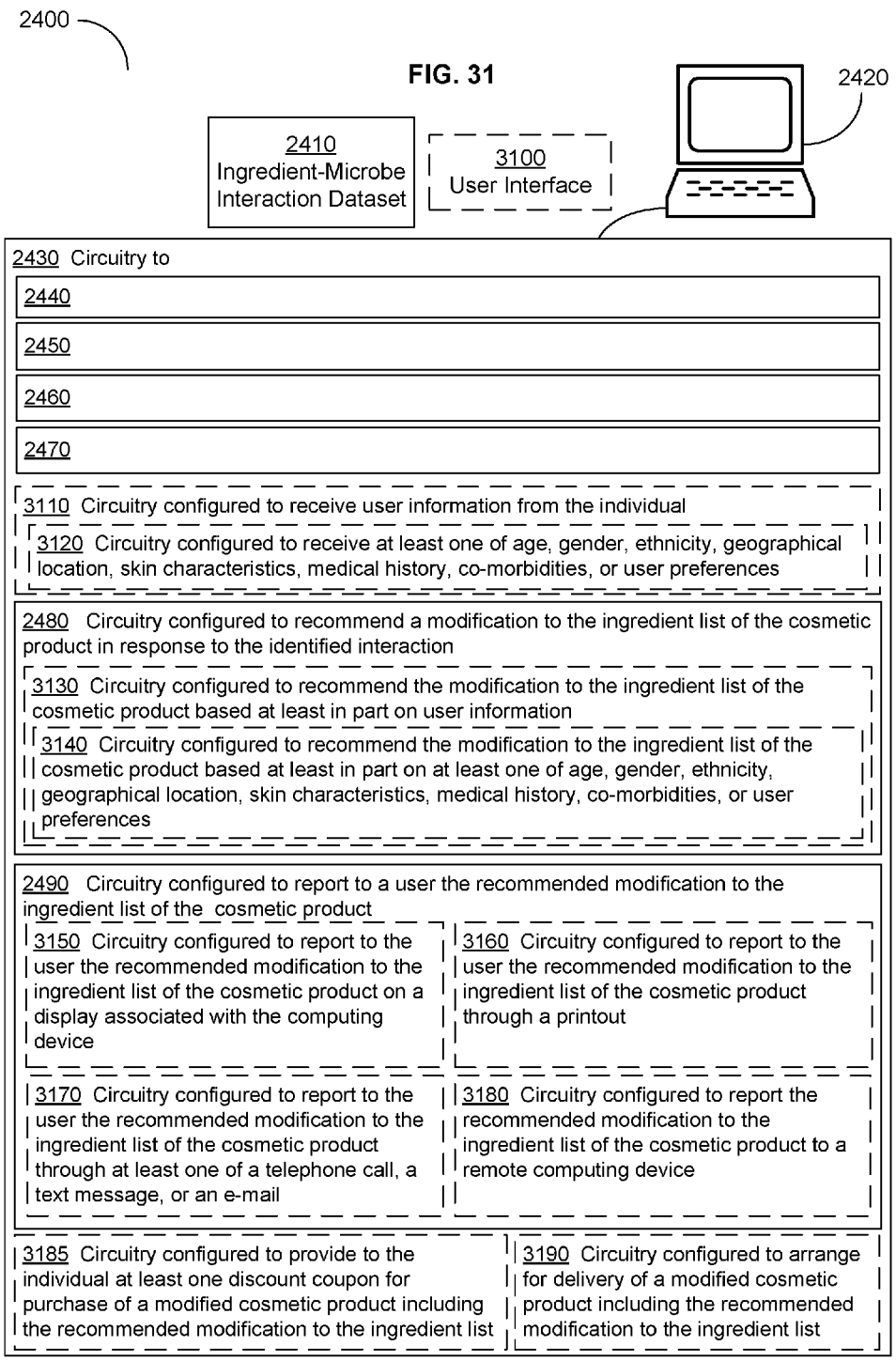

FIG. 33

3300
Receiving information associated with an ingredient list of the cosmetic product, the ingredient list of the cosmetic product including one or more cosmetic ingredients

3310
Receiving information associated with a microbe profile of an individual, the microbe profile including a distribution of one or more types of microbes on a skin surface of the individual

3320
Comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes

3330
Identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual

3340
Recommending a modification to the ingredient list of the cosmetic product in response to the identified interaction

3350
Reporting to a user the recommended modification to the ingredient list of the cosmetic product

FIG. 34

3300 Receiving information associated with an ingredient list of the cosmetic product, the ingredient list of the cosmetic product including one or more cosmetic ingredients 3400 Receiving the information associated with the one or more ingredients in the ingredient list of the cosmetic product 3410 Receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax in the ingredient list of the cosmetic product 3420 Receiving information associated with at least one of one or more probiotic agents, one or more prebiotic agents, or one or more therapeutic agents in the ingredient list of the cosmetic product 3430 Receiving the information associated with the ingredient list of the cosmetic product from a remote source 3440 Receiving the information associated with the ingredient list of the cosmetic product from a cosmetic distributer, a cosmetic manufacturer, or a cosmetic formulary 3450 Receiving the information associated with the ingredient list of the cosmetic product from a portable data storage device 3460 Receiving the information associated with the ingredient list of the cosmetic product from a scanning device 3310 Receiving information associated with a microbe profile of an individual, the microbe profile including a distribution of one or more types of microbes on a skin surface of the individual 3320 Comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes 3330 Identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual 3340 Recommending a modification to the ingredient list of the cosmetic product in response to the identified interaction 3350 Reporting to a user the recommended modification to the ingredient list of the cosmetic product

FIG. 35

| 3300 Receiving information associated with an ingredient list of the cosmetic product, the ingredient list of the cosmetic product including one or more cosmetic ingredients |
|---|
| 3310 Receiving information associated with a microbe profile of an individual, the microbe profile including a distribution of one or more types of microbes on a skin surface of the individual <br><br> 3500 Receiving the information associated with the microbe profile of the individual from a microbe profiling device <br><br> 3510 Receiving the information associated with the microbe profile of the individual from a microbe profiling system <br><br> 3520 Receiving the information associated with the microbe profile of the individual from a computing component associated with at least one of a microbe profiling device or a microbe profiling system <br><br> 3530 Receiving the information associated with the microbe profile of the individual from a portable data storage device <br><br> 3540 Receiving the information associated with the microbe profile of the individual from at least one of a remote computing device, a remote server, or the Internet |
| 3320 Comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes |
| 3330 Identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual |
| 3340 Recommending a modification to the ingredient list of the cosmetic product in response to the identified interaction |
| 3350 Reporting to a user the recommended modification to the ingredient list of the cosmetic product |

FIG. 37

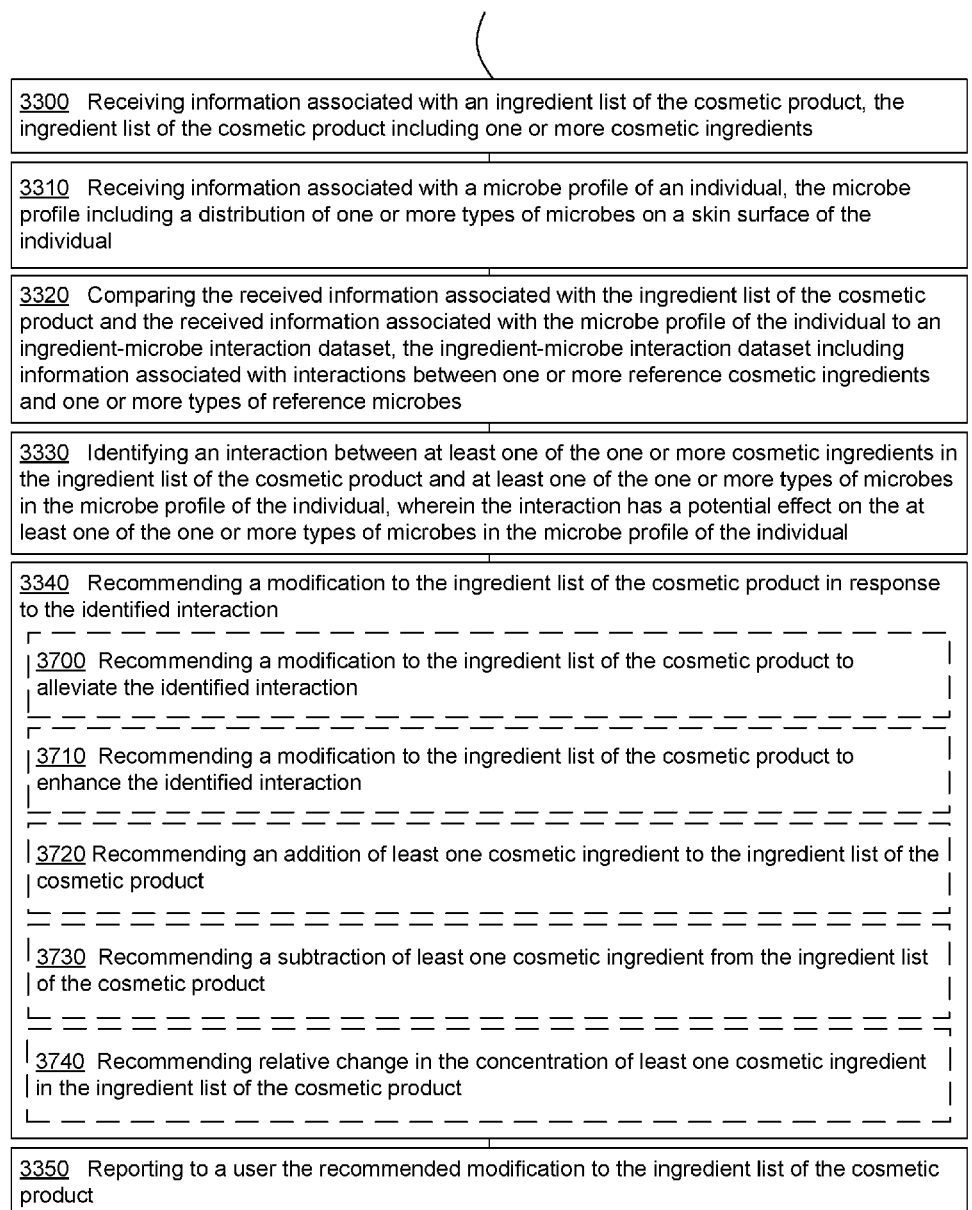

3300 Receiving information associated with an ingredient list of the cosmetic product, the ingredient list of the cosmetic product including one or more cosmetic ingredients 3310 Receiving information associated with a microbe profile of an individual, the microbe profile including a distribution of one or more types of microbes on a skin surface of the individual 3320 Comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes 3330 Identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual 3340 Recommending a modification to the ingredient list of the cosmetic product in response to the identified interaction 3700 Recommending a modification to the ingredient list of the cosmetic product to alleviate the identified interaction 3710 Recommending a modification to the ingredient list of the cosmetic product to enhance the identified interaction 3720 Recommending an addition of least one cosmetic ingredient to the ingredient list of the cosmetic product 3730 Recommending a subtraction of least one cosmetic ingredient from the ingredient list of the cosmetic product 3740 Recommending relative change in the concentration of least one cosmetic ingredient in the ingredient list of the cosmetic product 3350 Reporting to a user the recommended modification to the ingredient list of the cosmetic product

FIG. 38

| |
|---|
| 3300 Receiving information associated with an ingredient list of the cosmetic product, the ingredient list of the cosmetic product including one or more cosmetic ingredients |
| 3310 Receiving information associated with a microbe profile of an individual, the microbe profile including a distribution of one or more types of microbes on a skin surface of the individual |
| 3320 Comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes |
| 3330 Identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual |
| 3800 Receiving user information from the individual |
| 3810 Receiving at least one of age, gender, ethnicity, geographical location, skin characteristics, medical history, co-morbidities, or user preferences |
| 3340 Recommending a modification to the ingredient list of the cosmetic product in response to the identified interaction |
| 3820 Recommending the modification to the ingredient list of the cosmetic product based at least in part on user information |
| 3830 Recommending the modification to the ingredient list of the cosmetic product based at least in part on at least one of age, gender, ethnicity, geographical location, skin characteristics, medical history, co-morbidities, or user preferences |
| 3350 Reporting to a user the recommended modification to the ingredient list of the cosmetic product |

| | |
|---|---|
| 3840 Reporting to the user the recommended modification to the ingredient list of the cosmetic product on a display associated with a computing device | 3860 Reporting to the user the recommended modification to the ingredient list of the cosmetic product through at least one of a telephone call, a text message, or an e-mail |
| 3850 Reporting to the user the recommended modification to the ingredient list of the cosmetic product through a printout. | 3870 Reporting the recommended modification to the ingredient list of the cosmetic product to a computing device |

| |
|---|
| 3880 Providing to the individual at least one discount coupon for purchase of a modified cosmetic product including the recommended modification to the ingredient list |
| 3890 Arranging for delivery of a modified cosmetic product including the recommended modification to the ingredient list |

3910 Circuitry

3920
Circuitry for receiving information associated with an ingredient list of the cosmetic product, the ingredient list of the cosmetic product including one or more cosmetic ingredients

3930
Circuitry for receiving information associated with a microbe profile of an individual, the microbe profile including a distribution of one or more types of microbes on a skin surface of the individual

3940
Circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes

3950
Circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual

3960
Circuitry for recommending a modification to the ingredient list of the cosmetic product in response to the identified interaction

3970
Circuitry for reporting to a user the recommended modification to the ingredient list of the cosmetic product

FIG. 40

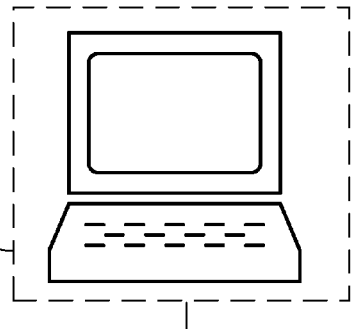

3900

4000

3910 Circuitry

3920
Circuitry for receiving information associated with an ingredient list of the cosmetic product, the ingredient list of the cosmetic product including one or more cosmetic ingredients 3930
Circuitry for receiving information associated with a microbe profile of an individual, the microbe profile including a distribution of one or more types of microbes on a skin surface of the individual 3940
Circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes 3950
Circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual 3960
Circuitry for recommending a modification to the ingredient list of the cosmetic product in response to the identified interaction 3970
Circuitry for reporting to a user the recommended modification to the ingredient list of the cosmetic product

3910  Circuitry

---

3920  Circuitry for receiving information associated with an ingredient list of the cosmetic product, the ingredient list of the cosmetic product including one or more cosmetic ingredients 4100  Circuitry for receiving the information associated with the one or more ingredients in the ingredient list of the cosmetic product 4110  Circuitry for receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax 4120  Circuitry for receiving information associated with at least one of one or more probiotic agents, one or more prebiotic agents, or one or more therapeutic agents 4130  Circuitry for receiving the information associated with the ingredient list of the cosmetic product from a remote source 4140  Circuitry for receiving the information associated with the ingredient list of the cosmetic product from a cosmetic distributer, a cosmetic manufacturer, or a cosmetic formulary 4150  Circuitry for receiving the information associated with the ingredient list of the cosmetic product from a portable data storage device 4160  Circuitry for receiving the information associated with the ingredient list of the cosmetic product from a scanning device

---

3930  Circuitry for receiving information associated with a microbe profile of an individual, the microbe profile including a distribution of one or more types of microbes on a skin surface of the individual

---

3940  Circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes

---

3950  Circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual

---

3960  Circuitry for recommending a modification to the ingredient list of the cosmetic product in response to the identified interaction

---

3970  Circuitry for reporting to a user the recommended modification to the ingredient list of the cosmetic product

| 3910 Circuitry |
|---|
| 3920 Circuitry for receiving information associated with an ingredient list of the cosmetic product, the ingredient list of the cosmetic product including one or more cosmetic ingredients |
| 3930 Circuitry for receiving information associated with a microbe profile of an individual, the microbe profile including a distribution of one or more types of microbes on a skin surface of the individual |
| 4200 Circuitry for receiving the information associated with the microbe profile of the individual from a microbe profiling device |
| 4210 Circuitry for receiving the information associated with the microbe profile of the individual from a microbe profiling system |
| 4220 Circuitry for receiving the information associated with the microbe profile of the individual from a computing component associated with at least one of a microbe profiling device or a microbe profiling system |
| 4230 Circuitry for receiving the information associated with the microbe profile of the individual from a portable data storage device |
| 4240 Circuitry for receiving the information associated with the microbe profile of the individual from at least one of a remote computing device, a remote server, or the Internet |
| 3940 Circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes |
| 3950 Circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual |
| 3960 Circuitry for recommending a modification to the ingredient list of the cosmetic product in response to the identified interaction |
| 3970 Circuitry for reporting to a user the recommended modification to the ingredient list of the cosmetic product |

| 3910 Circuitry |  |
|---|---|
| 3920 | 3930 |
| 3940 Circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes ||
| 4300 Circuitry for comparing the one or more types of microbes in the microbe profile of the individual to the one or more types of reference microbes in the ingredient-microbe interaction dataset ||
| 4310 Circuitry for comparing the one or more cosmetic ingredients in the ingredient list of the cosmetic product to the one or more reference cosmetic ingredients in the ingredient-microbe interaction dataset ||
| 3950 Circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual ||
| 4320 Circuitry for identifying the potential effect on the at least one of the one or more types of microbes in the microbe profile of the individual in response to the at least one of the one or more cosmetic ingredients in the ingredient list of the cosmetic product ||
| 4330 Circuitry for identifying a potential growth promoting effect on the at least one of the one or more types of microbes in the microbe profile of the individual in response to the at least one of the one or more cosmetic ingredients in the ingredient list of the cosmetic product ||
| 4340 Circuitry for identifying a potential growth inhibiting effect on the at least one of the one or more types of microbes in the microbe profile of the individual in response to the at least one of the one or more cosmetic ingredients in the ingredient list of the cosmetic product ||
| 4350 Circuitry for identifying a potential biofilm formation effect on the at least one of the one or more types of microbes in the microbe profile of the individual in response to the at least one of the one or more cosmetic ingredients in the ingredient list of the cosmetic product ||
| 3960 | 3970 |

| 3910 Circuitry |
|---|
| 3920 Circuitry for receiving information associated with an ingredient list of the cosmetic product, the ingredient list of the cosmetic product including one or more cosmetic ingredients |
| 3930 Circuitry for receiving information associated with a microbe profile of an individual, the microbe profile including a distribution of one or more types of microbes on a skin surface of the individual |
| 3940 Circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes |
| 3950 Circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual |
| 3960 Circuitry for recommending a modification to the ingredient list of the cosmetic product in response to the identified interaction |
|    4400 Circuitry for recommending a modification to the ingredient list of the cosmetic product to alleviate the identified interaction |
|    4410 Circuitry for recommending a modification to the ingredient list of the cosmetic product to enhance the identified interaction |
|    4420 Circuitry for recommending an addition of least one cosmetic ingredient to the ingredient list of the cosmetic product |
|    4430 Circuitry for recommending a subtraction of least one cosmetic ingredient from the ingredient list of the cosmetic product |
|    4440 Circuitry for recommending a relative change in the concentration of least one cosmetic ingredient in the ingredient list of the cosmetic product |
| 3970 Circuitry for reporting to a user the recommended modification to the ingredient list of the cosmetic product |

| 3910 Circuitry |
|---|
| 3920 Circuitry for receiving information associated with an ingredient list of the cosmetic product, the ingredient list of the cosmetic product including one or more cosmetic ingredients |
| 3930 Circuitry for receiving information associated with a microbe profile of an individual, the microbe profile including a distribution of one or more types of microbes on a skin surface of the individual |
| 3940 Circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes |
| 3950 Circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual |
| 4500 Circuitry for receiving user information from the individual |
|     4510 Circuitry for receiving at least one of age, gender, ethnicity, geographical location, skin characteristics, medical history, co-morbidities, or user preferences |
| 3960 Circuitry for recommending a modification to the ingredient list of the cosmetic product in response to the identified interaction |
|     4520 Circuitry for recommending the modification to the ingredient list of the cosmetic product based at least in part on user information |
|         4530 Circuitry for recommending the modification to the ingredient list of the cosmetic product based at least in part on at least one of age, gender, ethnicity, geographical location, skin characteristics, medical history, co-morbidities, or user preferences |
| 3970 Circuitry for reporting to a user the recommended modification to the ingredient list of the cosmetic product |
| 4540 Circuitry for reporting to the user the recommended modification to the ingredient list of the cosmetic product on a display associated with a computing device   |   4560 Circuitry for reporting to the user the recommended modification to the ingredient list of the cosmetic product through at least one of a telephone call, a text message, or an e-mail |
| 4550 Circuitry for reporting to the user the recommended modification to the ingredient list of the cosmetic product through a printout.   |   4570 Circuitry for reporting the recommended modification to the ingredient list of the cosmetic product to a computing device |
| 4580 Circuitry for providing to the individual at least one discount coupon for purchase of a modified cosmetic product including the recommended modification to the ingredient list   |   4590 Circuitry for arranging for delivery of a modified cosmetic product including the recommended modification to the ingredient list |

MODIFYING A COSMETIC PRODUCT BASED ON A MICROBE PROFILE

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority application(s)).

PRIORITY APPLICATIONS

The present application constitutes a continuation of U.S. patent application Ser. No. 14/294,491, entitled Modifying a Cosmetic Product Based on a Microbe Profile, naming Michael H. Baym, Roderick A. Hyde, Jordin T. Kare, Eric C. Leuthardt, Gary L. McKnight, Tony S. Pan, Elizabeth A. Sweeney, Clarence T. Tegreene, and Lowell L. Wood, Jr. as inventors, filed 3 Jun. 2014, which is currently co-pending or in an application of which a currently co-pending application is entitled to the benefit of the filing date.

The present application constitutes a continuation-in-part of U.S. patent application Ser. No. 13/975,055, entitled SYSTEMS, METHODS, AND DEVICES FOR ASSESSING MICROBIOTA OF SKIN, naming Mahalaxmi G. Bangera, Michael H. Baym, Roderick A. Hyde, Jordin T. Kare, Eric C. Leuthardt, Gary L. McKnight, Tony S. Pan, Katherine E. Sharadin, Elizabeth A. Sweeney, Clarence T. Tegreene, and Lowell L. Wood, Jr. as inventors, filed 23, Aug., 2013, which is currently co-pending or is an application of which a currently co-pending application is entitled to the benefit of the filing date.

The present application constitutes a continuation-in-part of U.S. patent application Ser. No. 14/091,762, entitled DEVICES AND METHODS FOR PROFILING MICROBIOTA OF SKIN, naming Michael H. Baym, Roderick A. Hyde, Jordin T. Kare, Eric C. Leuthardt, Gary L. McKnight, Tony S. Pan, Elizabeth A. Sweeney, Clarence T. Tegreene, Lowell L. Wood, Jr. as inventors, filed 27, Nov., 2013, which is currently co-pending or is an application of which a currently co-pending application is entitled to the benefit of the filing date.

The present application constitutes a continuation-in-part of U.S. patent application Ser. No. 14/091,832, entitled DEVICES AND METHODS FOR SAMPLING AND PROFILING MICROBIOTA OF SKIN, naming Michael H. Baym, Roderick A. Hyde, Jordin T. Kare, Eric C. Leuthardt, Gary L. McKnight, Tony S. Pan, Elizabeth A. Sweeney, Clarence T. Tegreene, Lowell L. Wood, Jr. as inventors, filed 27, Nov., 2013, which is currently co-pending or is an application of which a currently co-pending application is entitled to the benefit of the filing date.

The present application constitutes a continuation-in-part of U.S. patent application Ser. No. 14/192,613 entitled SYSTEMS, METHODS, AND DEVICES FOR DELIVERING TREATMENT TO A SKIN SURFACE, naming Roderick A. Hyde and Gary L. McKnight as inventors, filed 27, Feb., 2014, which is currently co-pending or is an application of which a currently co-pending application is entitled to the benefit of the filing date.

The present application constitutes a continuation-in-part of U.S. patent application Ser. No. 14/255,653 entitled SELECTING AND DELIVERING TREATMENT AGENTS BASED ON A MICROBE PROFILE, naming Michael H. Baym, Roderick A. Hyde, Jordin T. Kare, Eric C. Leuthardt, Gary L. McKnight, Tony S. Pan, Elizabeth A. Sweeney, Clarence T. Tegreene, Lowell L. Wood, Jr. as inventors, filed 17, Apr., 2014, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system for modifying a cosmetic product includes, but is not limited to, an ingredient-microbe interaction dataset including information associated with interactions between one or more reference cosmetic ingredients and one or more types of reference microbes; and a computing device including a processor and circuitry, the circuitry configured to receive information associated with a microbe profile of an individual, the microbe profile including a distribution of one or more types of microbes on a skin surface of the individual; receive information associated with an ingredient list of the cosmetic product, the ingredient list including one or more cosmetic ingredients; compare the received information associated with the microbe profile of the individual and the received information associated with the ingredient list of the cosmetic product to the ingredient-microbe interaction dataset; identify an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; recommend a modification to the ingredient list of the cosmetic product in response to the identified interaction; and report to a user the recommended modification to the ingredient list of the cosmetic product. In addition to the foregoing, other aspects of a system are described in the claims, drawings, and text forming a part of the present disclosure.

In an aspect, a method of modifying a cosmetic product includes, but is not limited to, receiving information associated with a microbe profile of an individual, the microbe profile including a distribution of one or more types of microbes on a skin surface of the individual; receiving information associated with an ingredient list of the cosmetic product, the ingredient list of the cosmetic product including one or more cosmetic ingredients; comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes; identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; recommending a modification to the ingredient list of the cosmetic product in response to the identified interaction; and reporting to a user the recommended modification to the ingredient list of the cosmetic product. In addition to the foregoing, other aspects of a method are described in the claims, drawings, and text forming a part of the present disclosure.

In an aspect, a system for modifying a cosmetic product includes, but is not limited to, circuitry for receiving information associated with a microbe profile of an individual, the microbe profile including a distribution of one or more types of microbes on a skin surface of the individual; circuitry for receiving information associated with an ingredient list of the cosmetic product, the ingredient list of the cosmetic product including one or more cosmetic ingredients; circuitry for comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes; circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; circuitry for recommending a modification to the ingredient list of the cosmetic product in response to the identified interaction; and circuitry for sending a signal to report to a user the recommended modification to the ingredient list of the cosmetic product. In addition to the foregoing, other aspects of a system are described in the claims, drawings, and text forming a part of the present disclosure.

In an aspect, a system for modifying a cosmetic product includes, but is not limited to, a computing device; an ingredient-microbe interaction dataset including information associated with interactions between one or more reference cosmetic ingredients and one or more types of reference microbes; and non-transitory machine-readable media including one or more instructions for modifying the cosmetic product, the one or more instructions including one or more instructions for receiving information associated with a microbe profile of an individual, the microbe profile including a distribution of one or more types of microbes on a skin surface of the individual; one or more instructions for receiving information associated with an ingredient list of the cosmetic product, the ingredient list including one or more cosmetic ingredients; one or more instructions for comparing the received information associated with the microbe profile of the individual and the received information associated with the ingredient list of the cosmetic product to the ingredient-microbe interaction dataset; one or more instructions for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; one or more instructions for recommending a modification to the ingredient list of the cosmetic product in response to the identified interaction; and one or more instructions for reporting to a user the recommended modification to the ingredient list of the cosmetic product. In addition to the foregoing, other aspects of a system are described in the claims, drawings, and text forming a part of the present disclosure.

In an aspect, a system for modifying a cosmetic product includes, but is not limited to, an ingredient-microbe interaction dataset including information associated with interactions between one or more types of reference microbes and one or more reference cosmetic ingredients; a computing device including a processor and circuitry, the circuitry configured to receive an ingredient list of the cosmetic product, the ingredient list including one or more cosmetic ingredients; receive a microbe profile of an individual, the microbe profile including a distribution of one or more types of microbes on the skin surface of the individual; compare the received information associated with the ingredient list of the cosmetic product and the received information associated with the microbe profile of the individual to the ingredient-microbe interaction dataset; identify an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual; recommend a modification to the ingredient list of the cosmetic product in response to the identified interaction; and report to a user the recommended modification to the ingredient list of the cosmetic product. In addition to the foregoing, other aspects of a system are described in the claims, drawings, and text forming a part of the present disclosure.

In an aspect, a method for modifying a cosmetic product includes, but is not limited to, receiving an ingredient list of the cosmetic product, the ingredient list including one or more cosmetic ingredients; receiving a microbe profile of an individual, the microbe profile including a distribution of one or more types of microbes on the skin surface of the individual; comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes; identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual; recommending a modification to the ingredient list of the cosmetic product in response to the identified interaction; and reporting to a user the recommended modification to the ingredient list of the cosmetic product. In addition to the foregoing, other aspects of a method are described in the claims, drawings, and text forming a part of the present disclosure.

In an aspect, a system includes, but is not limited to, circuitry for receiving an ingredient list of the cosmetic product, the ingredient list including one or more cosmetic ingredients; circuitry for receiving a microbe profile of an individual, the microbe profile including a distribution of one or more types of microbes on the skin surface of the individual; circuitry for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes; circuitry for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual; circuitry for recommending a modification to the ingredient list of the cosmetic product in response to the identified interaction; and circuitry for reporting to a user the recommended modification to the ingredient list of the cosmetic product. In addition to the foregoing, other aspects of a system are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 illustrates a system for modifying a cosmetic product based on a microbe profile.

FIG. 2 illustrates further aspects of a system such as shown in FIG. 1.

FIG. 4 shows further aspects of a system such as depicted in FIG. 1.

FIG. 5 depicts further aspects of a system such as illustrated in FIG. 1.

FIG. 6 illustrates further aspects of a system such as shown in FIG. 1.

FIG. 7 shows further aspects of a system such as depicted in FIG. 1.

FIG. 8 depicts further aspects of a system such as illustrated in FIG. 1.

FIG. 9 illustrates further aspects of a system such as shown in FIG. 1.

FIG. 10 is a flowchart of a method of modifying a cosmetic product based on a microbe profile.

FIG. 11 illustrates further aspects of a method such as depicted in FIG. 10.

FIG. 12 depicts further aspects of a method such as shown in FIG. 10.

FIG. 13 shows further aspects of a method such as illustrated in FIG. 10.

FIG. 14 illustrates further aspects of a method such as depicted in FIG. 10.

FIG. 16 illustrates a system for modifying a cosmetic product based on a microbe profile.

FIG. 17 depicts further aspects of a system such as illustrated in FIG. 16.

FIG. 18 illustrates further aspects of a system such as shown in FIG. 16.

FIG. 19 shows further aspects of a system such as depicted in FIG. 16.

FIG. 20 depicts further aspects of a system such as illustrated in FIG. 16.

FIG. 21 illustrates further aspects of a system such as shown in FIG. 16.

FIG. 22 shows further aspects of a system such as depicted in FIG. 16.

FIG. 25 illustrates further aspects of a system such as shown in FIG. 24.

FIG. 27 depicts further aspects of a system such as illustrated in FIG. 24.

FIG. 28 illustrates further aspects of a system such as shown in FIG. 24.

FIG. 30 depicts further aspects of a system such as illustrated in FIG. 24.

FIG. 31 illustrates further aspects of a system such as shown in FIG. 24.

FIG. 33 is a flowchart of a method of modifying a cosmetic product based on a microbe profile.

FIG. 34 illustrates further aspects of a method such as shown in FIG. 33.

FIG. 35 shows further aspects of a method such as depicted in FIG. 33.

FIG. 37 illustrates further aspects of a method such as shown in FIG. 33.

FIG. 38 shows further aspects of a method such as depicted in FIG. 33.

FIG. 39 illustrates a system for modifying a cosmetic product based on a microbe profile.

FIG. 40 shows further aspects of a system such as depicted in FIG. 39.

FIG. 41 depicts further aspects of a system such as illustrated in FIG. 39.

FIG. 42 illustrates further aspects of a system such as shown in FIG. 39.

FIG. 43 shows further aspects of a system such as depicted in FIG. 39.

FIG. 44 depicts further aspects of a system such as illustrated in FIG. 39.

FIG. 45 illustrates further aspects of a system such as shown in FIG. 39.

DETAILED DESCRIPTION

Figure 3:
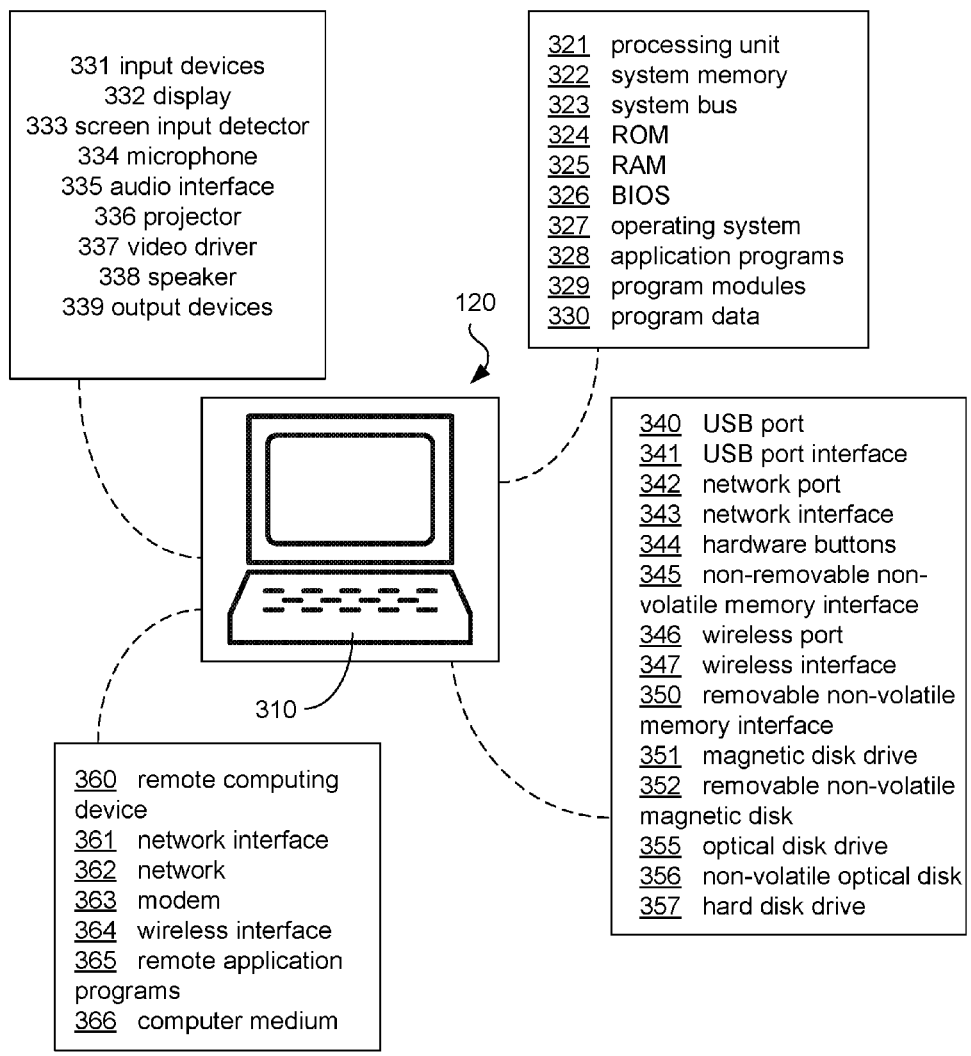
FIG. 3 illustrates aspects of a computing device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A microbiota, a collective microbial community inhabiting a specific environment, e.g., a human body, can include archaea, bacteria, viruses, and eukaryotes. The microbes comprising a microbiota can play important roles in the health of a body including metabolism, homeostasis of the immune system, and colonization resistance. The skin, the largest organ of the mammalian body, is inhabited by a diverse array of microbes, including bacteria, fungi, viruses, parasites, archaea, or small arthropods (e.g., mites). Variations in regional properties of the skin, e.g., variations in pH, moisture, pores, texture, and the like, from one body location to another contribute to the spatial diversity of skin-associated microbes. Similarly, the type of microbes and/or spatial distribution of one or more microbes on the skin surface may change in response to any disturbance of the area, such as cleaning of the skin surface; application of anti-microbial agents; application of irritating agents, e.g., make-up, lotion, sun screen; or exposure to irritating conditions, e.g., diet, disease, wind, or sun exposure. In some instances, skin-resident microbes on the skin surface, e.g., commensal bacteria, provide a benefit to the individual and have been linked to the body's ability to mount a robust immune response. For example, *Staphylococcus epidermidis* has been demonstrated to modulate the host innate immune response and inhibit other bacterial pathogens such as *Staphylococcus aureus* and Group A *Streptococcus*. See, e.g., Grice & Segre (2011) *Nat. Rev. Microbiol.* 9:244-53, which is incorporated herein by reference. In some instances, skin-resident microbes have been linked to pathological conditions including acne, eczema, and atopic dermatitis. See, e.g., Cho & Blaser (2012) *Nat. Rev. Genet.* 13:260-270, which is incorporated herein by reference. In general, understanding the identity and spatial distribution of skin-resident microbes on the skin under normal and/or pathological conditions can contribute to decisions regarding therapeutic, preventative, and/or cosmetic treatments. Described here are embodiments of systems and methods for modifying a cosmetic product based on a microbe profile of an individual.

With reference to FIG. 1, shown is a system for modifying a cosmetic product. System 100 includes an ingredient-microbe interaction dataset 110 including information associated with interactions between one or more reference cosmetic ingredients and one or more types of reference microbes; and a computing device 120. Computing device 120 includes a processor and circuitry 130. Circuitry 130 includes circuitry 140 configured to receive information associated with a microbe profile of an individual, the microbe profile including a distribution of one or more types of microbes on a skin surface of the individual; circuitry 150 configured to receive information associated with an ingredient list of the cosmetic product, the ingredient list including one or more cosmetic ingredients; circuitry 160 configured to compare the received information associated with the microbe profile of the individual and the received information associated with the ingredient list of the cosmetic product to the ingredient-microbe interaction dataset; circuitry 170 configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; circuitry 180 configured to recommend a modification to the ingredient list of the cosmetic product in response to the identified interaction; and circuitry 190 configured to report to a user the recommended modification to the ingredient list of the cosmetic product.

Ingredient-Microbe Interaction Dataset

System 100 includes ingredient-microbe interaction dataset 110 including information associated with interactions between one or more reference cosmetic ingredients and one or more types of reference microbes. For example, the ingredient-microbe interaction dataset can include a list of reference microbes, e.g., types of microbes commonly found on a skin surface or associated with pathogenesis, matched with interactions with reference cosmetic ingredients, e.g., ingredients commonly found in cosmetic products. For example, the ingredient-microbe interaction dataset can include a list of reference microbes and the ability of said reference microbes to assimilate, e.g., metabolize, all or part of a cosmetic ingredient, e.g., hydrocarbons, silicones, alcohols, esters, and/or fatty acids. See, e.g., Yanagi & Onishi (1971) *J. Soc. Cosmet. Chem.* 22:851-856, which is incorporated herein by reference. For example, the ingredient-microbe interaction dataset can include a list of reference microbes that consume and/or metabolize certain cosmetic ingredients in cosmetic products and by so doing, changing a characteristic, e.g., color, texture, pH, or odor, of the cosmetic product.

FIG. 2 illustrates further aspects of an ingredient-microbe interaction dataset. In an aspect, ingredient-microbe interaction dataset 110 includes one or more reference cosmetic ingredients 200. In an aspect, the one or more reference cosmetic ingredients include one or more cosmetic ingredients in at least one cosmetic product. For example, the one or more reference cosmetic ingredients can include a dataset of cosmetic ingredients commonly used in cosmetic products. For example, the one or more reference cosmetic ingredients can include a dataset of cosmetic ingredient lists of a plurality of cosmetic products. For example, the one or more reference cosmetic ingredients can include a list of cosmetic products and a corresponding list of the cosmetic ingredients included in each of the listed cosmetic products. For example, the ingredient list can include a dataset that includes any of a number of GRAS (Generally Regarded As Safe) ingredients as outlined under sections 201(s) and 409 of the Federal Food, Drug, and Cosmetic Act.

In an aspect, the one or more reference cosmetic ingredients 200 include one or more of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emollient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax, as shown in block 205.

In an aspect, the one or more reference cosmetic ingredients include one or more of colorants, fragrances, steric acid, lecithin, beeswax, carnauba wax, or other plant-based waxes, tocopherol, glycerin, hydrolyzed rice protein, kaolin, hydrolyzed corn starch, oleyl alcohol, dimethicone, talc, glyceryl stearate, mineral oil, propylene glycol, polypropylene glycol, butylene glycol, hexylene glycol, ethoxydiglycol, dipropylene glycol, triethanolamine, diethanolamine, ethanolamine, sodium chloride, squalane, squalene, or preservative ingredients.

In an aspect, the one or more reference cosmetic ingredients include one or more silicate, non-limiting examples of which include aluminum silicate, calcium silicate, magnesium aluminum silicate, magnesium silicate, magnesium tri silicate, sodium magnesium silicate, zirconium silicate, attapulgite, bentonite, Fuller's earth, hectorite, kaolin, lithium magnesium silicate, lithium magnesium sodium silicate, montmorillonite, pyrophyllite, or zeolite. Silicates may be used as abrasives, absorbents, anticaking agents, binders, bulking agents, emulsion stabilizers, opacifying agents, slip modifiers, suspending agents, and viscosity altering agents.

In an aspect, the one or more reference cosmetic ingredients include one or more cosmetic ingredients derived from *Ricinus communis* (castor) seed oil, non-limiting examples of which include cetyl rinoleate, ethyl ricinoleate, glyceryl ricinoleate, glyceryl ricinoleate, glycol ricinoleate, hydrogenated castor oil, isopropyl ricinoleate, methyl ricinoleate, octyldodecyl ricinoleate, potassium ricinoleate, ricinoleic acid, sodium ricinoleate, or zinc ricinoleate. Castor seed oil derivatives can be used as anticaking agents, deodorizing agents, emulsion stabilizers, opacifying agents, surfactants, and viscosity altering agents.

In an aspect, the one or more reference cosmetic ingredients include cellulose and/or one or more modified forms of cellulose polymer, non-limiting examples of which include calcium carboxymethyl cellulose, carboxymethyl cellulose acetate butyrate, carboxymethyl hydroxyethylcellulose, cellulose acetate, cellulose acetate butyrate, cellulose gum, cellulose acetate propionate, cellulose acetate propionate carboxylate, cellulose succinate, cetyl hydroxyethylcellulose, ethylcellulose, hydrolyzed cellulose gum, hydroxybutyl methylcellulose, hydroxyethyl cellulose, hydroxyethyl ethylcellulose, hydroxypropylcellulose, hydroxypropyl methylcellulose, methylcellulose, hydroxypropyl methylcellulose acetate/succinate, methylcellulose, methyl ethylcellulose, methyl hydroxyethyl cellulose, microcrystalline cellulose, potassium cellulose succinate, or sodium cellulose sulfate. Cellulose and modified cellulose forms can be used as abrasives, absorbents, adhesives, anticaking agents, binders, bulking agents, emulsion stabilizers, film formers, opacifying agents, slip modifiers, and viscosity altering agents.

In an aspect, the one or more reference cosmetic ingredients include tocopherol or vitamin E, or derivatives thereof, non-limiting examples of which include tocophersolan, tocopheryl acetate, tocopheryl linoleate, tocopheryl linoleate/oleate, tocopheryl nicotinate, tocopheryl succinate, dioleyl tocopheryl methylsilanol, or potassium ascorbyl tocopheryl phosphate. In an aspect, the one or more reference cosmetic ingredients include vitamin C derivatives, non-limiting examples of which include ascorbyl palmitate, ascorbyl dipalmitate, ascorbyl stearate, erythorbic acid, or sodium erythorbate. Vitamin E and vitamin C derivatives can be used as antioxidants.

In an aspect, the one or more reference cosmetic ingredients include one or more fatty acids, non-limiting examples of which include stearic acid, lauric acid, myristic acid, oleic acid, palmitic acid, and derivatives thereof. In an aspect, the one or more reference cosmetic ingredients include one or more acyl sarcosine fatty acids or acyl sarcosinate salts thereof. In an aspect, the one or more reference cosmetic ingredients include one or more polyethylene glycol (PEG) sorbitan/sorbital fatty acid esters, e.g., PEG-20 sorbitan cocoate. In an aspect, the one or more reference cosmetic ingredients include one or more sucrose fatty acid esters, e.g., sucrose distearate. In an aspect, the one or more reference cosmetic ingredients include one or more propylene glycol monoesters or diesters, fatty acid derivatives of diethanolamine, or glyceryl diesters. Fatty acids can be used as opacifying and/or surfactant agents. In an aspect, the one or more reference cosmetic ingredients can include one or more lipids. Non-limiting examples of lipids include ceramide derivatives, cholesterol, phytosphingosine. Lipids can be used to moisturize the skin.

In an aspect, the one or more reference cosmetic ingredients include silicone based polymers, non-limiting examples of which include dimethicone, methicone, amino bispropyl dimethicone, aminopropyl dimethicone, amodimethicone, amodimethicone hydroxystearate, behenoxy dimethicone, C30-45 alkyl dimethicone, C24-28 alkyl dimethicone, C30-45 alkyl methicone, cetearyl methicone, cetyl dimethicone, dimethoxysilyl ethylenediaminopropyl dimethicone, hexyl methicone, hydroxypropyldimethicone, stearamidopropyl dimethicone, stearoxy dimethicone, stearyl methicone, stearyl dimethicone, or vinyl dimethicone. Silicone based polymers can be used as antifoaming agents, corrosion inhibitors, film formers, skin-conditioning agents, skin protectant, surface modifier, and/or viscosity altering agents.

In an aspect, the one or more reference cosmetic ingredients include one or more colorants. Some colorants can be described as organic or inorganic. Some colorants can derive from natural sources or synthetic sources. Non-limiting examples of organic colorant include plant extracts, henna, annatto, caramel, or beta-carotene. Non-limiting examples of inorganic colorants include minerals. Non-limiting examples of minerals used in cosmetics include bismuth citrate, disodium EDTA-copper, potassium sodium copper chlorophyllin, dihydroxyacetone, bismuth oxychloride, guaiazulene, henna, iron oxides, ferric ammonium ferrocyanide, ferric ferrocyanide, chromium hydroxide green, guanine, lead acetate, pyrophyllite, mica, silver, titanium dioxide, aluminum powder, bronze powder, copper powder, ultramarines, manganese violet, zinc oxide, or luminescent zinc sulfide.

In an aspect, the one or more reference cosmetic ingredients include one or more dyes, non-limiting examples of which include D&C Black No. 2, D&C Black No. 3, D&C Blue No. 1, D&C Blue No. 4, D&C Brown No. 1, FD&C Green No. 3, D&C Green No. 5, D&C Green No. 6, D&C Green No. 7, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, D&C Yellow No.

5, FD&C Yellow No. 6, D&C Yellow No. 7, Ext. D&C Yellow No. 7, or D&C Yellow No. 8, D&C Yellow No. 10, or D&C Yellow No. 11.

In an aspect, the one or more reference cosmetic ingredients include one or more chromogenic agents capable of changing color in response to the presence of one or more types of microbes. For example, the one or more reference cosmetic ingredients can include a chromogenic agent that is an enzyme substrate which releases a chromogen upon metabolism by an enzyme system of the microbe. For example, the chromogenic agent can include an indoxyl substrate, non-limiting examples of which include indoxyl-β-glucopyranoside, indoxyl-myo-inositol-1-phosphate, indoxyl-N-acetyl-β-D-glucosaminide, indoxyl-phosphate, indoxyl-β-D-glucoside, indoxyl-β-glucuronide, indoxyl-β-galactoside, indoxyl-α-D-glucoside, indoxyl-β-D-glucuronide, indoxyl-α-galactoside, indoxyl-β-glucoside, indoxyl-β-D-ribofuranoside, 7-amido-1-pentyl-phenoxazin-3-one, indoxyl-fatty acid ester, indoxyl-α-D-glucopyranoside, phenolphthalein phosphate, indoxyl-N-acetyl-β-D-glusaminide, or inoxyl-β-D-xyloside.

In an aspect, the one or more reference cosmetic ingredients include one or more preservatives, non-limiting examples of which include paraben, formaldehyde, calcium sorbate, sodium sorbate, TEA-sorbate, imidazolidinyl urea, potassium undecylenate and related ingredients, propionic acid and related salts, sorbic acid, potassium sorbate, and other agents having antimicrobial or antioxidizing properties.

In an aspect, the one or more reference cosmetic ingredients include one or more antiseptic agents, non-limiting examples of which include alcohols (e.g., ethanol or isopronanol), quaternary ammonium compounds (e.g., benzalkonium chloride), boric acid, chlorhexidine gluconate, hydrogen peroxide, iodine, povidone-iodine, octenidine dihydrochloride, phenol, or polyhexanide, In an aspect, the one or more reference cosmetic ingredients include one or more anesthetic agents. In an aspect, the one or more anesthetic agents include one or more topical anesthetic agents. Non-limiting examples of anesthetic agents include benzocaine, butamben, dibucaine, lidocaine, oxybuprocaine, pramoxine, proparacaine, proxymetacaine, or tetracaine.

In an aspect, the one or more reference cosmetic ingredients include one or more buffers or buffering agents. In an aspect, the one or more reference cosmetic ingredients include one or more buffers or buffering agents for maintaining the pH of the cosmetic product and/or the skin surface of the individual. In an aspect, the one or more reference cosmetic ingredients include one or more buffers for modulating the pH of the cosmetic product and/or the skin surface of the individual. In an aspect, the one or more reference cosmetic ingredients include weak acids and/or bases for use as buffers. In an aspect, the one or more reference cosmetic ingredients include at least one of calcium carbonate, sodium phosphate, potassium acetate, potassium citrate, sodium acetate, sodium citrate, sodium bicarbonate, boric acid, ammonium phosphate, potassium pyrophosphate, sodium pyrophosphate, HEPES, diethylamine, sodium succinate, sodium lactate, potassium lactate, sodium silicate, ammonium lactate, or any other weak acid and/or weak base appropriate for buffering and use on a skin surface.

In an aspect, the one or more reference cosmetic ingredients include at least one of a moisturizer, an astringent, an anti-aging treatment agent, a retinoid, or a cosmetic agent. In an aspect, the one or more reference cosmetic ingredients include at least one of witch hazel, calamine, rubbing alcohol, or zinc oxide. In an aspect, the one or more reference cosmetic ingredients include one or more of keratoregulators, keratolytics, healing and/or restructuring agents of the cutaneous barrier, PPAR, RXR or LXR agonists, sebum-regulating agents, anti-irritation and/or anti-inflammatory and/or soothing agents, antioxidant agents, anti-aging agents, depigmenting or hypopigmenting agents, pigmenting agents, lipolytic or lipogenesis inhibitor agents or anti-cellulitis or slimming agents, organic or mineral sunscreens and filters, preservatives, or immunomodulators.

In an aspect, the one or more reference cosmetic ingredients 200 include at least one of one or more probiotic agents, one or more prebiotic agents, or one or more therapeutic agents 210. In an aspect, the one or more reference cosmetic ingredients include one or more probiotic agents. In an aspect, the one or more probiotic agents include one or more skin commensal microorganisms which positively affect the skin microbiota. For example, the one or more probiotic agents can include microorganisms that positively affect the skin surface environment, e.g., by altering the pH or inhibiting growth of pathogenic microorganisms. In an aspect, the one or more probiotic agents can include one or more microorganisms naturally found on the skin surface of an individual. In an aspect, the one or more probiotic agents can include one or more microorganisms that are not naturally found on the skin surface of an individual, but positively affect the skin surface environment. In an aspect, the one or more probiotic agents can include one or more engineered microorganisms. For example, the one or more probiotic agents can include a microorganism genetically engineered to have a property that positively affects the skin surface environment, e.g., by synthesizing and excreting an inhibitor of pathogenic microorganisms. See, e.g., Martin et al. (2013) *Microbial Cell Factories*, 12:71, which is incorporated herein by reference. In an aspect, the probiotic comprises live probiotic microorganisms. In an aspect, the probiotic agent may be included in a live form, dead form, semi-active or in deactivated form, or as fragments or fractions originating from the microorganism either live or dead (e.g., as a lyophilized powder). In an aspect, the probiotic agent includes culture supernatants of the microorganisms.

In an aspect, the one or more reference cosmetic ingredients include one or more bacterial probiotic agents. See, e.g., U.S. Pat. No. 8,557,560, U.S. Patent Applications 2011/0274676, 2014/0037688, Schrezenmeir & De Vrese (2001) *Am. J. Clin. Nutr.* 73(suppl):3615-3645, and Gueniche et al. (2009) *Exp. Dermatol.* 19:e1-e8, which are incorporated herein by reference. In an aspect, the one or more bacterial probiotic agents include at least one type of bacteria from Firmicutes, Actinobacteria, Bacteriodetes, Proteobacteria, or Cyanobacteria. In an aspect, the one or more bacterial probiotic agents include at least one type of bacteria from Corynebacteria, Propionibacteria, Micrococci, or Staphylococci. In an aspect, the one or more bacterial probiotic agents include non-lactic acid and/or lactic acid producing bacteria (LAB) and can include *Bacteroides, Bifidobacterium,* and *Lactobacillus*. In an aspect, the one or more bacterial probiotic agents include certain strains of *Aerococcus, E. coli, Bacillus, Enterococcus, Fusobacterium, Lactococcus, Leuconostoc, Melissacoccus, Micrococcus, Oenococcus, Sporolactobacillus, Streptococcus, Staphylococcus, Saccharomyces, Pediococcus, Peptostreptococcus, Proprionebacterium,* and *Weissella*. A wide variety of strains of bacteria are available from the ATCC (American Type Culture Collection), Manassas, Va. In an aspect, the one or more probiotic agents include at least one of a non-pathogenic strain of a pathogenic bacterium.

In an aspect, the one or more reference cosmetic ingredients include a bacterial probiotic agent that is a bacterial strain that inhibits a second bacterial strain, e.g., by out competing for resources or by inhibiting the growth of the second bacterial stain. In an aspect, the bacterial probiotic agent can include *Staphylococcus epidermidis*, a skin commensal microorganism. For example, *Staphylococcus epidermidis* may be used as a probiotic to modulate growth of pathogenic bacteria on the skin surface by producing microbial peptides that inhibit *Staphylococcus aureus* biofilm formation and/or by producing lanthionine-containing antibacterial peptides, e.g., bacteriocins, which are known to exhibit antibacterial properties toward certain species of harmful bacteria, e.g., *Streptococcus aureus* and *Streptococcus pyogenes*. For example, *Staphylococcus epidermidis* may be used as a probiotic to stimulate the immune system by influencing the innate immune response of keratinocytes through Toll-like receptor ("TLR") signaling. For example, *Staphylococcus epidermidis* may be used as a probiotic to inhibit the action of more virulent microorganisms such as *Staphylococcus aureus* by occupying receptors on a host cell that also bind the virulent microorganism. See, e.g., Grice & Segre (2011) *Nat. Rev. Microbiol.* 9:244-53, which is incorporated herein by reference. Non-limiting examples of other bacteriocins are described in the BACTIBASE database referenced in Hammami et al (2007) *BMC Microbiology* 7:89, which is incorporated herein by reference.

In an aspect, the one or more reference cosmetic ingredients include *Propionibacterium acnes*, another skin commensal microorganism. As an example, *Propionibacterium acnes* can be used as a probiotic to consume skin oil and to produce byproducts such as short-chain fatty acids and propionic acid known to help maintain a healthy skin barrier. See, e.g., Shu et al. (2013) *PLoS ONE* 8(2):e55380, which is incorporated herein by reference.

In an aspect, the one or more reference cosmetic ingredients include one or more prebiotic agents. In an aspect, the one or more prebiotic agents promote the survival and/or growth of microorganisms of interest on the skin surface of the individual. In an aspect, the one or more prebiotic agents include at least one of oligosaccharides, e.g., galacto-oligosaccharides and/or fructo-oligosaccharides, inulin, or lactulose. In an aspect, the one or more prebiotic agents include one or more of iron, biotin, nicotinic acid, D-pantothenic acid, pyridoxal, pyridoxamine dihydrochloride, thiamin hydrochloride, valine, arginine, galactose, mannose, fructose, sucrose, lactose, or maltose. In an aspect, the one or more prebiotic agents include one or more of plant derived prebiotics, e.g., derived from acacia gum, konjac, chicory root, Jerusalem artichoke, asparagus, or dandelion greens. See, e.g., U.S. Patent Application 2013/0115317; and Bateni et al. (2013) *Am. J. Dermatology Venereology* 2:10-14, which are incorporated herein by reference.

In an aspect, the one or more reference cosmetic ingredients include one or more antimicrobial agents, e.g., antibacterial agents, antifungal agents, or antiviral agents. In an aspect, the one or more antimicrobial agents include one or more antibacterial agents configured to prevent or minimize a bacterial infection on a skin surface of an individual. Non-limiting examples of antibacterial agents commonly used for topical applications include benzoyl peroxide, sodium sulfacetamide, erythromycin, mupirocin, retapamulin, bacitracin, neomycin, polymyxin b/e, silver sulfadiazine, or tetracycline. In an aspect, the one or more antimicrobial agents include one or more antiviral agents configured to prevent or treat a viral infection. For example, the one or more reference cosmetic ingredients can include an antiviral agent to prevent or treat viral infection of the skin surface associated with herpes simplex types 1 or 2. Non-limiting examples of antiviral agents commonly used for topical applications include acyclovir, docosanol, famciclovir, imiquimod, penciclovir, valacyclovir, and vidarabine. In an aspect, the one or more antimicrobial agents include one or more antifungal agents configured to prevent or treat a fungal infection on the skin surface of a user. Non-limiting examples of antifungal agents commonly used for topical applications include clotrimazole, amphotericin B, butaconazole, butenafine, ciclopirox olamine, econazole, ketoconazole, miconazole, naftifine, natamycin, nystatin, oxiconazole, sulconazole, terbinafine, terconazole, tioconazole, and tolnaftate.

In an aspect, the one or more reference cosmetic ingredients include one or more enzymes or enzyme inhibitors. In an aspect, the one or more reference cosmetic ingredients include one or more substrates for a microbial enzyme for use in competing with endogenous substrates. In an aspect, the one or more reference cosmetic ingredients include one or more ester or esterase inhibitor. For example, *Corynebacteria* produce esterases that hydrolyze sebum fats to alcohols and free fatty acids, the latter of which can block sebaceous glands and contribute to the development of acne; the one or more reference cosmetic ingredients can include one or more esters that can compete for the esterase and/or can be an ester or ester derivative that is metabolized to an antibacterial compound. In an aspect, the one or more reference cosmetic ingredients include one or more lipase. For example, the one or more reference cosmetic ingredients can include a lipase able to degrade skin lipids and promote colonization of beneficial bacteria. In an aspect, the one or more reference cosmetic ingredients include one or more lipase inhibitors. For example, a lipase inhibitor can be used to inhibit deterioration of cosmetic solubilizers (polysorbate-20, polysorbate-80, polyethylene glycol, hydrogenated castor oil) by *Pseudomonas*. See, e.g., Wachi, et al (1980) *J. Soc. Cosmet. Chem.* 31:67-84, which is incorporated herein by reference.

In an aspect, the one or more reference cosmetic ingredients include one or more therapeutic agents. In an aspect, the one or more reference cosmetic ingredients include one or more therapeutic agents to treat other conditions of a skin surface. Non-limiting examples of conditions or diseases of the skin include inflammation, e.g., eczema, hives, atopic dermatitis, or psoriasis; a microbial infection, e.g., a bacterial, fungal, or viral infection; acne, actinic keratosis, rosacea, seborrheic dermatitis, seborrheic keratosis, warts, or skin cancer, e.g., melanoma, squamous cell carcinoma, or basal cell carcinoma; tinea pedis; aging skin; and dry or sensitive skin. In an aspect, the one or more therapeutic agents include at least one of an anti-inflammatory agent, a chemotherapeutic agent, an antiseptic agent, an anesthetic agent, or an anti-acne agent. In an aspect, the one or more therapeutic agents include one or more of vitamins (e.g., Vitamin A or Vitamin D), vitamin derivatives, benzoyl peroxide, salicylic acid or other acids, hormone or retinoid creams, steroids, cortisone, emollients, moisturizers, or chemotherapeutics, (e.g., 5-fluorourasil). In an aspect, the one or more therapeutic agents include one or more retinoids for treating various conditions of the skin including, but not limited to, acne, psoriasis, photodamaged skin and cancers including AIDS-related Kaposi's sarcoma and cutaneous T-cell lymphoma. Non-limiting examples of retinoids for topical use include alitretinoin, bexarotene, adapalene, tazarotene, and isotretinoin.

In an aspect, the one or more reference cosmetic ingredients include one or more corticosteroid for treating various inflammatory dermatoses including, but not limited to, atopic dermatitis, psoriasis, lupus erythematosus, and the like. Non-limiting examples of corticosteroids for topical use include hydrocortisone and derivatives, betamethasone and derivatives, dexamethasone, prednisolone and derivatives, fluocinolone acetonide, fluorometholone, alclometasone dipropionate, triamcinolone acetonide, clocortolone pivalate, flumethasone pivalate, mometasone furoate, flurandrenolide, prednicarbate, fluticasone propionate, desonide, halcinonide, desoximetasone, flurandrenolide, fluocinonide, amcinonide, fluocinolone acetonide, and diflorasone diacetate.

In an aspect, the one or more reference cosmetic ingredients include one or more chemotherapy agents for treating cancer or other conditions of the skin surface. Non-limiting examples of chemotherapy agents for topical use include fluorouracil used for treating actinic keratoses and some types of basal cell carcinomas of the skin.

In an aspect, the one or more reference cosmetic ingredients include at least one of an immunomodulator, non-limiting examples of which include imiquimod, tacrolimus and pimecrolimus. In an aspect, the one or more reference cosmetic ingredients include at least one agent for modulating pigmentation, non-limiting examples of which include hydroquinone, monobenzone, mequinol, trioxsalen and methoxsalen.

In an aspect, ingredient-microbe interaction dataset 110 includes a list of one or more types of reference microbes 215. In an aspect, the one or more types of reference microbes include one or more types of mutualistic microbes, commensal microbes, or pathogenic microbes. In an aspect, the one or more types of reference microbes include one or more types of skin-associated microbes 220. For example, the one or more types of reference microbes can include one or more types of commensal microbes resident on the skin surface. For example, the one or more types of reference microbes can include one or more types of pathogenic microbes associated with the skin surface. Non-limiting examples of skin-associated or skin-resident bacteria include proteobacteria, e.g., *Pseudomonas* sp., *Janthinobacterium* sp, *Alphaproteobacteria*, other gammaproteobacteria, and betaproteobacteria; *Actinobacteria*, e.g., *Kocuria* sp., *Propionibacteria* sp.; *Firmicutes*, e.g., *Staphylococcus epidermidis*; *Bacteroidetes*; and *Spirochaetes*. See, e.g., Grice et al. (2008) *Genome Res.* 18:1043-1050; Grice & Segre (2011) *Nat. Rev. Microbiol.* 9:244-253, which are incorporated herein by reference. Non-limiting examples of fungi, including skin-resident or associated types of fungi, include dermatophtyes, e.g., *trichophyton, microsporum, epidermophyton*, tinea capitis. Other skin-associated fungi include but are not limited to yeast, *Candida*, e.g., *Candida albicans*; and *Malassezia* spp (e.g., *M. dermatis, M. furfur, M. globosa*, and *M. restricta*). See, e.g., Gaitanis et al. (2012) *Clin. Microbiol. Rev.* 25:106-141, which is incorporated herein by reference. Non-limiting examples of skin-associated or skin-resident viruses include herpes simplex virus type I (HSV-1), herpes zoster, Molluscum contagiosum, human papillomavirus (HPV), Coxsackie virus A16, and herpes gladiatorum. Non-limiting examples of other parasites resident or associated with a skin surface include skin-associated parasitic arthropods including parasitic mites, e.g., *Demodex* spp including *D. folliculorum* and *D. brevis*, and *Sarcoptes scabiei*, a skin parasite associated with scabies.

Ingredient-microbe interaction dataset 110 includes information associated with interactions between one or more reference cosmetic ingredients and one or more types of reference microbes, as shown in block 225. In an aspect, ingredient-microbe interaction dataset 110 includes information associated with the potential effect on the one or more reference cosmetic ingredients in response to the one or more types of reference microbes, as shown in block 230. For example, the ingredient-microbe interaction dataset can include a list of reference cosmetic ingredients, e.g., a list of ingredients commonly used in cosmetic ingredients, and a corresponding list of reference microbes, e.g., skin-associated microbes, that effect properties of the reference cosmetic ingredients.

In an aspect, ingredient-microbe interaction dataset 110 includes information associated with a potential color effect on the one or more reference cosmetic ingredients in response to the one or more types of reference microbes, as shown in block 235. In an aspect, the potential color effect is caused by alterations in the one or more reference cosmetic ingredients in response to pH, redox, or other reactions caused by the metabolic activities of a microbe. For example, bacteria in the *Pseudomonas* genus metabolize a broad range of compounds and can produce soluble pigments ranging in color from blue-green to brown. See, e.g., Smart & Spooner (1972) *J. Soc. Cosmet. Chem.* 23:721-737, which is incorporated herein by reference. For example, the color of an ingredient may change in response to fermentation of certain sugars, e.g., dextrose or lactose, or other carbohydrates in the cosmetic product. In an aspect, the potential color effect occurs in response to a change in pH due to interaction of a reference cosmetic ingredient with a type of reference microbe. For example, a weak acid pigment with a conjugate base form may undergo a striking color change when the pigment is neutralized. In an aspect, the potential color effect occurs in response to reference cosmetic ingredient that is a microbe-responsive chromogenic agent. In an aspect, an individual may prefer a specific color effect, e.g., a color change, over the course of wearing a particular cosmetic product. For example, the cosmetic product may include a pH sensitive pigment that changes color over the course of the day as microbes on the skin surface interact with one or more cosmetic ingredients in the cosmetic product and modulate the skin surface pH. For example, the cosmetic product may include a chromogenic agent that is responsive to enzymatic activity of microbe-specific enzymes. See, e.g., Manafi (2000) *Int. J. Food Microbiol.* 60:205-218, which is incorporated herein by reference.

In an aspect, ingredient-microbe interaction dataset 110 includes information associated with a potential texture effect on the one or more reference cosmetic ingredients in response to the one or more types of reference microbes, as shown in block 240. For example, the interaction of one or more reference cosmetic ingredients with one or more types of microbes can result in texture changes. For example, microbial metabolism may result in a homogeneous product becoming visibly heterogeneous, e.g., separating into different phases. Emulsions, for instance, are susceptible to changes in physicochemical conditions; hydrolysis of the oil phase or changes in pH of an aqueous phase will upset the equilibrium and cause visible changes in the emulsion. In liquid products, changes of viscosity can be seen to occur when microbes break down large molecules, metabolize sugars, or cause aggregation of particles in suspension. For example, the change in texture can include creams becoming lumpy or gritty. See, e.g., Smart & Spooner (1972) *J. Soc. Cosmet. Chem.* 23:721-737, which is incorporated herein by reference.

In an aspect, ingredient-microbe interaction dataset 110 includes information associated with a potential pH effect on the one or more reference cosmetic ingredients in response to the one or more types of reference microbes, as shown in block 245. In general, normal skin pH ranges from about 4.4 to about 5.8. The pH of a cosmetic ingredient can alter the pH of the skin surface. In addition, changes in skin pH can also increase and/or decrease microbes associated with the skin surface. In an acidic product, oxidative yeast can cause a rise in pH by utilizing organic acids which will in turn encourage bacterial growth. For example, increases in skin pH lead to increases in coagulate-negative Staphylococci and Propionibacteria. See, e.g., Korting et al (1990) *Acta Derm. Venereol.* 70:429-431, which is incorporated herein by reference.

In an aspect, ingredient-microbe interaction dataset 110 includes information associated with a potential odor effect on the one or more reference cosmetic ingredients in response to the one or more types of reference microbes, as shown in block 250. For example, the interaction can include an interaction between one or more reference cosmetic ingredients and one or more types of odor-producing bacteria. For example, enzymes secreted by bacteria, e.g., exoesterases, beta-glucuronidase and/or aryl sulfatase, can react with a reference cosmetic ingredient, e.g., water-soluble steroid conjugates, to release volatile, odorous, free steroids. See, e.g., Froebe et al (1990) *J. Soc. Cosmet. Chem.* 41:173-185. For example, the odor can include sulfur-containing metabolites such as hydrogen sulfide, sickly smells of fatty acids, fishy odors of amines, or the astringency of ammonia. For example, the acrid odor of steroids is apparent in the presence of Coryneform bacteria, but the odor of isovaleric acid prevails in the presence of *Staphylococcus epidermidis*. See, e.g., Smart & Spooner (1972) *J. Soc. Cosmet. Chem.* 23:721-737, which is incorporated herein by reference.

In an aspect, ingredient-microbe interaction dataset 110 is incorporated into a memory component of computing device 120, as shown in block 255. In an aspect, the ingredient-microbe interaction dataset is loaded into a memory component of computing device 120 prior to sale or distribution to a user, e.g., the individual or other individual. In an aspect, the ingredient-microbe interaction dataset is in the form of a look-up table. In an aspect, the ingredient-microbe interaction dataset is loaded into a memory component of computing device 120 from a portable data storage component, e.g., a memory stick or CD ROM, or from a remote computing device.

In an aspect, ingredient-microbe interaction dataset 110 is stored on a portable data storage device, as shown in block 260. Non-limiting examples of portable data storage devices include flash memory cards, Memory Sticks, mass storage devices, CompactFlash, non-volatile memory cards, Secure Digital™ (SD) cards, mini SD cards, microSD cards, USB flash drive, or XQD cards. In an aspect, computing device 120 includes a port or docking site sized to accept a portable data storage device that includes ingredient-microbe interaction dataset 110, and circuitry configured to access ingredient-microbe interaction dataset 110 from the inserted or docked portable data storage device. For example, the computing device of the system can include a port or docking site sized to accept a portable data storage device, e.g., a CD-ROM, or memory card or stick, and circuitry configured to access the ingredient-microbe interaction dataset from the inserted or docked portable data storage device.

In an aspect, ingredient-microbe interaction dataset 110 is stored on a remote computing device, as shown in block 265. In an aspect, the remote computing device is associated with a cosmetic supplier, distributer, and/or manufacturer. In an aspect, the ingredient-microbe interaction dataset is accessible to the computing device from a remote computing device through the Internet or other web-based communication link. In an aspect, the ingredient-microbe interaction dataset is accessible to the computing device from a remote computing device through a server, e.g., a cloud-based server. In an aspect, the remote computing device includes a smart phone, cellular phone, a tablet, or other personal computing device.

In an aspect, ingredient-microbe interaction dataset 110 is updatable, as shown in block 270. For example, as new data becomes available regarding the interaction of specific microbes or classes of microbes with specific reference cosmetic ingredients, the data can be added to the ingredient-microbe interaction dataset. In an aspect, updates to the ingredient-microbe interaction dataset are accessible to the computing device of the system through a web-based communication link, e.g., through the Internet, or through delivery of a portable data storage device, e.g., a memory card, including an updated ingredient-microbe interaction dataset.

Computing Device and Circuitry

System 100 includes computing device 120. Computing device 120 can take various forms or be part of an object, such as a personal computer, a limited resource computing device, a wireless communication device, a mobile wireless communication device, a handheld electronic writing device, a tablet, a cell phone, a PDA, or an electronic tablet device. In an aspect, computing device 120 includes a computing component including a processor and circuitry associated with a device or system. In an aspect, computing device 120 is associated with a microbe profiling device, e.g., a hand-held microbe profiling device. In an aspect, computing device 120 is associated with a microbe profiling system, e.g., an at-home microbe profiling system. In an aspect, computing device 120 is associated with a kiosk in a medical facility, e.g., in a dermatology clinic, or in a commercial space, e.g., in a shopping center. In an aspect, computing device 120 is associated with a manufacturing device, e.g., a device or apparatus configured to formulate a cosmetic product and/or to fill a container, e.g., a glass or plastic bottle or vial, with a cosmetic product.

Computing device 120 includes circuitry 130 configured to receive information associated with a microbe profile of an individual, the microbe profile including a distribution of one or more types of microbes on a skin surface of the individual; circuitry configured to receive information associated with an ingredient list of the cosmetic product, the ingredient list including one or more cosmetic ingredients; circuitry configured to compare the received information associated with the microbe profile of the individual and the received information associated with the ingredient list of the cosmetic product to the ingredient-microbe interaction dataset; circuitry configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; circuitry configured to recommend a modification to the ingredient list of the cosmetic product in response to the identified interaction; and circuitry configured to report to a user the recommended modification to the ingredient list of the cosmetic product.

Computing device 120 further includes circuitry configured to execute one or more instructions. In an aspect, computing device 120 includes circuitry configured to execute one or more instructions for receiving information associated with a microbe profile of an individual, the microbe profile including a distribution of one or more types of microbes on a skin surface of the individual; one or more instructions for receiving an ingredient list of the cosmetic product, the ingredient list including one or more cosmetic ingredients; one or more instructions for comparing the received information associated with the microbe profile of the individual and the received information associated with the ingredient list of the cosmetic product to the ingredient-microbe interaction dataset; one or more instructions for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; one or more instructions for recommending a modification to the ingredient list of the cosmetic product in response to the identified interaction; and one or more instructions for reporting to a user the recommended modification to the ingredient list of the cosmetic product.

FIG. 3 illustrates further aspects of computing device 120. Computing device 120 includes a processing unit 321, a system memory 322, and a system bus 323 that couples various system components including the system memory 322 to the processing unit 321. Processing unit 321 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGA having a plurality of programmable logic commands.

The system bus 323 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing device can include one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In one embodiment, one or more user input/output components are operably coupled to the computing device to control (electrical, electromechanical, software-implemented, firmware-implemented, or other control, or combinations thereof) receiving the microbe profile of the individual, receiving the ingredient list of the cosmetic product, comparing the received information with an ingredient-microbe interaction dataset, identifying an interaction, recommending a modification to the ingredient list of the cosmetic product in response to the identified interaction, and reporting the recommended modification to a user.

The system memory includes read-only memory (ROM) 324 and random access memory (RAM) 325. A basic input/output system (BIOS) 326, containing the basic routines that help to transfer information between sub-components within computing device 120, such as during start-up, is stored in the ROM 324. A number of program modules may be stored in the ROM 324 or RAM 325, including an operating system 327, one or more application programs 328, other program modules 329 and program data 330.

In an aspect, computing device 120 includes a user interface. The user interface may include a character, a key-based, or another user data input including a keyboard or touch sensitive display. The user interface may include a stylus. Moreover, the user interface is not limited to an actual touch-sensitive panel arranged for directly receiving input, but may alternatively or in addition respond to another input device such as the microphone 334. For example, spoken words may be received at the microphone 334 and recognized.

In an aspect, the user interface includes input devices 331 for inputting commands and/or information into computing device 120. In an aspect, input devices include, but are not limited to a microphone, keyboard, or pointing device, commonly referred to as a mouse, trackball, or touch pad. Other input devices may include at least one of a touch sensitive display, joystick, game pad, satellite dish, and scanner. These and other input devices are often connected to the processing unit through a user input interface that is coupled to the system bus, but may be connected by other interface and bus structures, such as a parallel port, game port, or a universal serial bus (USB). In an aspect, the individual or other user may enter commands and information into computing device 120 through a number of switches and buttons, illustrated as hardware buttons 344, connected to the system via a suitable non-removable non-volatile memory interface 345. Input devices 331 may further include a touch-sensitive display with suitable input detection circuitry, illustrated as a display 332 and screen input detector 333. The output circuitry of the touch-sensitive display 332 is connected to the system bus 323 via a video driver 337. Other input devices may include a microphone 334 connected through a suitable audio interface 335, and a physical hardware keyboard 310.

In an aspect, the user interface includes output devices 339 for outputting commands and/or information from computing device 120. Output devices 339 may include at least one display 332, a speaker 338, or a projector 336. In addition to the display 332, the computing device 120 may include other peripheral output devices 339, such as at least one speaker 338.

In an aspect, other external input devices 331 or output devices 339, such as a joystick, game pad, satellite dish, scanner or the like, may be connected to the processing unit 321 through a USB port 340 and USB port interface 341, to the system bus 323. Alternatively, the other external input devices 331 and output devices 339 may be connected by other interfaces, such as a parallel port, game port or other port.

The computing device 120 may further include or be capable of connecting to a flash card memory through an appropriate connection port. The computing device 120 may further include or be capable of connecting with a network through a network port 342 and network interface 343, and through wireless port 346 and corresponding wireless interface 347 may be provided to facilitate communication with other peripheral devices, including a microbe profiling device, a microbe profiling system, an analyzer, or a kiosk. It will be appreciated that the various components and connections shown are examples and other components and means of establishing communication links may be used.

In certain instances, the computing device typically includes a variety of computer-readable media products. Computer-readable media may include any media that can be accessed by the computing device and may include both volatile and nonvolatile media, removable and non-removable media. By way of example, and not of limitation, computer-readable media may include computer storage media. By way of further example, and not of limitation, computer-readable media may include a communication media. By way of further example, and not of limitation, computer readable media may include non-transitory signal bearing media. Non-limiting examples of non-transitory signal-bearing media include a recordable type medium such as magnetic tape, a hard disk drive, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. By way of example, and not of limitation, computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing component. By way of further example, and not of limitation, computer-readable media may include a communication media, e.g., wired media, such as a wired network and a direct-wired connection, and wireless media such as acoustic, RF, optical, and infrared media.

Communication media may typically embody computer-readable instructions, data structures, program modules, or other data in a modulated data signal such as a carrier wave or other transport mechanism, and include any information delivery media. The term "modulated data signal" means a signal that has one or more of its characteristics set or changed in such a manner as to encode information in the signal. By way of example, and not limitation, communication media may include wired media, such as a wired network and a direct-wired connection, and wireless media such as acoustic, RF, optical, and infrared media.

The computing device may also include other removable/non-removable, volatile/nonvolatile computer storage media products. For example, such media includes a non-removable non-volatile memory interface (hard disk interface) 345 reads from and writes for example to non-removable, non-volatile magnetic media, or a removable non-volatile memory interface 350 that, for example, is coupled to a magnetic disk drive 351 that reads from and writes to a removable, non-volatile magnetic disk 352, or is coupled to an optical disk drive 355 that reads from and writes to a removable, non-volatile optical disk 356, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 357 is typically connected to the system bus 323 through a non-removable memory interface, such as the interface 345, and magnetic disk drive 351 and optical disk drive 355 are typically connected to the system bus 323 by a removable non-volatile memory interface, such as interface 350.

The drives and their associated computer storage media discussed above provide storage of computer-readable instructions, data structures, program modules, and other data for the computing device. In an aspect, the computer storage media discussed above provides storage for the ingredient-microbe interaction dataset including information associated with potential interactions of one or more ingredient in a cosmetic product with one or more types of reference microbes. In an aspect, the computer storage media discussed above provides storage for the ingredient list of one or more cosmetic products.

The computing device may operate in a networked environment using logical connections to one or more remote computers, such a remote computing device 360. The remote computing device 360 may be a personal computer, a server, a router, a network PC, a peer device, or other common network node, and typically includes many or all of the elements described above relative to the computing device 120. The remote computing device 360 may further include a computing component associated with a microbe profiling device, a microbe profiling system, a kit including an analyzer, or a kiosk. The remote computing device 360 may further include a personal computing device, e.g., a cellular phone, smart phone, tablet, or other hand-held and mobile personal computing device. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing device is connected to the network 362 through a network interface, such as the network interface 361, the modem 363, or the wireless interface 364. The network may include a LAN network environment, or a WAN network environment, such as the Internet. In a networked environment, program modules depicted relative to the computing device 120, or portions thereof, may be stored in a remote memory storage device. By way of example, and not limitation, remote application programs 365 may reside on computer medium 366. It will be appreciated that the network connections shown are examples and other means of establishing a communication link between the computers may be used.

In certain instances, one or more elements of the computing device 120 may be deemed not necessary and omitted. In other instances, one or more other components may be deemed necessary and added to the computing device 120.

In one embodiment, image-based applications such as viewers and/or toolkits (e.g., Insight Segmentation and Registration Toolkit (ITK)), are incorporated for further intake of information. In one embodiment, CAD implementations or image segmentation may allow processing of received digital images.

In one embodiment, the computing device includes a computer-readable media drive or memory slot that is configured to accept non-transitory signal-bearing medium (e.g., computer-readable memory media, computer-readable recording media, or the like). In one embodiment, a program for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, cloud, or the like.

In one embodiment, the computing device includes one or more modules optionally operable for communication with one or more input/output components that are configured to relay user output/input. In one embodiment, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electromechanical systems (MEMS) elements, or other actuators.

Circuitry 130 of system 100 includes circuitry 140 configured to receive information associated with a microbe profile of an individual, the microbe profile including a distribution of one or more types of microbes on a skin surface of the individual. In an aspect, the microbe profile of the individual includes a spatial distribution of one or more types of microbes on a skin surface of the individual. For example, the microbe profile of the individual can include a spatial distribution of one or more types of microbes on a skin surface associated with the face, neck, head, scalp, torso, buttocks, upper extremities, lower extremities, or genital regions of the individual. For example, the microbe profile of the individual can include a spatial distribution of a first type of microbe, e.g., a first type of bacteria, relative to a spatial distribution of a second type of microbe, e.g., a second type of bacteria. In an aspect, the microbe profile of the individual includes the identity of one or more types of microbes on the skin surface of the individual. In an aspect, the one or more types of microbes include one or more types of bacteria, fungus, virus, parasite, archaea, or small arthropod (e.g., mites). In an aspect, the one or more types of microbes include at least one type of mutualistic microbe, commensal microbe, or pathogenic microbe. In an aspect, the one or more types of microbes include at least one type of introduced microbe, e.g., a probiotic or genetically engineered microbe. In an aspect, the one or more types of microbes include at least one type of commensal or pathogentic microbe, e.g., at least one type of commensal or pathogenic skin-resident microbe.

In an aspect, the microbe profile of the individual includes a spatial distribution and/or identification of one or more types of microbes on the skin surface of the individual. Non-limiting examples of commensal or pathogenic skin-associated or skin-resident bacteria include proteobacteria, e.g., *Pseudomonas* sp., *Janthinobacterium* sp, *Alphaproteobacteria*, other gammaproteobacteria, and betaproteobacteria; *Actinobacteria*, e.g., *Kocuria* sp., *Propionibacteria* sp.; *Firmicutes*, e.g., *Staphylococcus epidermidis; Bacteroidetes*; and *Spirochaetes*. See, e.g., Grice et al. (2008) *Genome Res.* 18:1043-1050; Grice & Segre (2011) *Nat. Rev. Microbiol.* 9:244-253, which are incorporated herein by reference. Non-limiting examples of commensal or pathogenic fungi, including commensal or pathogenic skin-resident or associated types of fungi, include dermatophtyes, e.g., *trichophyton, microsporum, epidermophyton*, tinea capitis. Other skin-associated fungi include but are not limited to yeast, *Candida*, e.g., *Candida albicans*; and *Malassezia* spp (e.g., *M. dermatis, M. furfur, M. globosa*, and *M. restricta*). See, e.g., Gaitanis et al. (2012) *Clin. Microbiol. Rev.* 25:106-141, which is incorporated herein by reference. Non-limiting examples of skin-associated or skin-resident viruses include herpes simplex virus type I (HSV-1), herpes zoster, Molluscum contagiosum, human papillomavirus (HPV), Coxsackie virus A16, and herpes gladiatorum. Non-limiting examples of other parasites resident on or associated with a skin surface include skin-associated parasitic arthropods including parasitic mites, e.g., *Demodex* spp including *D. folliculorum* and *D. brevis*, and *Sarcoptes scabiei*, a skin parasite associated with scabies.

FIG. 4 illustrates further aspects of a system such as shown in FIG. 1. In an aspect, circuitry 140 of system 100 includes circuitry 400 configured to receive the information associated with the microbe profile of the individual from a microbe profiling device. In an aspect, system 100 includes circuitry configured to receive the information associated with a microbe profiling device that directly detects one or more types of microbes on the skin surface of an individual. For example, the microbe profiling device can include an optical microbe profiling device that scans the skin surface with an optical energy source, e.g., light emitted from a fiber optic, laser, or light emitting diode, and detects signals emitted or reflected in situ from the microbes on the skin surface in response to the optical energy source. See, e.g., U.S. Pat. No. 8,280,471, to Rainone et al., and titled "Fiber optic based detection of fluorescent bacterial pathogens," which is incorporated herein by reference.

In an aspect, system 100 includes circuitry configured to receive the information associated with a microbe profiling device that indirectly detects one or more types of microbes on the skin surface of an individual. For example, the microbe profiling device can include a microbe sampling component for sampling one or more types of microbes from a skin surface and a detecting component for detecting the one or more types of microbes captured with the microbe sampling component. In an aspect, the microbe profiling device includes a microbe sampling unit including a microbe-capture region, e.g., one or more materials configured to selectively or non-selectively capture one or more types of microbes from a skin surface, at least one sensor component, e.g., an optical or fluorescence sensor, a user interface, e.g., a touchscreen display, and a computing component including a microprocessor and circuitry configured to generate a microbe profile. In an aspect, system 100 includes circuitry configured to receive the information associated with the microbe profile of the individual from a hand-held microbe profiling device that includes a device head and a hand-held housing, the device head including an epidermis-engaging component, e.g., a brush, a razor, or abrasive pad, and at least one access window, and the hand-held housing defining an opening aligned with the at least one access window of the device head, and including a microbe sampling unit, at least one sensor component, e.g., an optical or fluorescence sensor, at least one location-capture component, e.g., an image capture device, and a computing component including a microprocessor and circuitry configured to generate the microbe profile. Other non-limiting aspects of hand-held microbe profiling devices are described in U.S. patent application Ser. Nos. 14/091, 762, 14/091,793, and 14/091,805, each of which is incorporated herein by reference.

In an aspect, system 100 includes circuitry configured to receive the information associated with the microbe profile of the individual from a microbe profiling device that includes a rotatable microbe sampling unit including the microbe-capture region. For example, the hand-held microbe profiling device can include a rotatable microbe sampling unit that is a cassette with one or more rotatable components including the microbe capture region. Non-limiting aspects of a hand-held microbe profiling device with a rotatable microbe sampling unit are described in U.S. patent application Ser. Nos. 14/091,832, and 14/091,856, each of which is incorporated herein by reference. In an aspect, a hand-held microbe profiling device includes an analyzer and a replaceable microbe sampling unit, e.g., a replaceable substrate including a microbe-capture region.

In an aspect, system 100 includes circuitry configured to receive the information associated with the microbe profile of the individual from a microbe profiling device that includes a microbe sampling unit with a microbe-capture region including one or more materials configured to non-selectively capture one or more types of microbes. For example, the microbe-capture region can include a material, e.g., an adhesive, which non-selectively binds microbes from the skin surface of an individual. In an aspect, the microbe-capture region includes one or more materials that interact with biomolecules on the outer surface of microbes, e.g., proteins, polysaccharides, carbohydrates, phospholipids, proteoglycans, and the like, non-limiting examples of which include poly-ionic surfaces, e.g., poly-cationic surfaces such as polyamino acids (e.g., polylysine), fibronectin, nitrocellulose, cellulose nitrate, hydrophobic polymers, polyvinylidene fluoride coating, nylon coating, streptavidin or biotin, proteins, peptides, Concanavalin A, epoxy for binding proteins and peptides, aldehydes for immobilizing amino modified oligos and cDNAs, native proteins, tissues, and cells, and amines for immobilizing long oligos and cDNAs. Other non-limiting examples include adhesives, absorbents, adsorbents, gels (e.g., hydrogels, colloids, agar, or gelatin), biomolecule-binding polymers (e.g., nitrocellulose or poly-L-lysine), and extracellular matrix components (e.g., collagen, laminin, fibronectin, mucopolysaccharides, heparin sulfate, hyaluronidate, and chondroitin sulfate).

In an aspect, system 100 includes circuitry configured to receive the information associated with the microbe profile of the individual from a microbe profiling device that includes a microbe sampling unit with a microbe-capture region including one or more materials configured to selectively capture one or more types of microbes. In an aspect, the one or more materials configured to selectively capture the one or more types of microbes include one or more specific microbe-binding elements that recognize and bind at least one type of microbe, e.g., at least one type of bacteria, fungus, or virus, on the skin surface of an individual. In an aspect, the specific microbe-binding element is configured to specifically recognize and bind a particular microbe or class of microbes. In an aspect, the specific microbe-binding element may be specific for a particular type of microbe, e.g., bacteria versus fungus. In an aspect, the specific microbe-binding element may be specific for Gram-positive versus Gram-negative bacteria or for a particular genus of microbes, e.g., *Propionibacterium* versus *Staphylococcus*. In an aspect, the specific microbe-binding element may be specific for a particular species of bacteria within a genus, e.g., *S. aureus* versus *S. epidermidis*. Specific microbe-binding elements can include substances derived from natural or synthetic sources. Non-limiting examples of specific microbe-binding elements include antibodies, aptamers, oligonucelotides, or anti-16S rRNA ligands. Other non-limiting examples of specific microbe-binding elements include antibody fragments, peptides, DNA, RNA, peptide nucleic acids, proteins, viruses, lipid, glycolipids, sphingolipids, phospholipids, carbohydrates, enzymes, receptors, lectins, peptide aptamers, bacteria, cells, cell fragments, inorganic molecules, organic molecules, artificial binding substrates (e.g., those formed by molecular imprinting), or combinations thereof.

In an aspect, system 100 includes circuitry configured to receive the information associated with the microbe profile of the individual from a microbe profiling device that includes a microbe sampling unit with a microbe-capture region including one or more materials configured to selectively generate a signal in response to interaction with one or more types of microbes on the skin surface. For example, the system can include circuitry configured to receive the information associate with the microbe profile of the individual from a microbe profiling device that includes a microbe-capture region with a plurality of signal-generating complexes, e.g., a signal-generating element operably coupled to a specific microbe-binding element, which emit a signal in response to interaction with one or more types of microbes. For example, the plurality of signal-generating complexes can include optical signal-generating complexes, fluorescing signal-generating complexes, electromagnetic signal-generating complexes, radio signal-generating complexes, electrical current signal-generating complexes, acoustic signal-generating complexes, or magnetic signal-generating complexes.

In an aspect, circuitry 140 of system 100 includes circuitry 410 configured to receive the information associated with the microbe profile of the individual from a microbe profiling system. In an aspect, system 100 includes circuitry configured to receive the information associated with the microbe profile of the individual from a microbe profiling system that includes at least one of a microbe sampling unit including a microbe-capture region, a microbe sampling device, an analyzer including at least one sensor component to detect one or more signals emitted or reflected from the microbe sampling unit, and a computing component including a processor and circuitry configured to generate a microbe profile based on sensor output from the at least one sensor component. In an aspect, system 100 includes circuitry configured to receive the information associated with the microbe profile of the individual sampled using at least one of a mask, a mouthpiece, a strip, a swab, a brush, a sponge, or a razor. For example, system 100 can include circuitry configured to receive the information associated with the microbe profile of the individual from a microbe profiling system that includes a mask, e.g., a pre-formed or peelable mask, which substantially conforms to the topography of the skin surface of the individual and captures and/or interacts with microbes on the skin surface upon contact. For example, system 100 can include circuitry configured to receive the information associated with the microbe profile of the individual from a microbe profiling system that includes a mouthpiece formed from a settable material (e.g., sodium alginate, polyether, silicones, polyvinyl siloxane, agar, or zinc oxide eugenol) using a dental or impression tray. Other non-limiting aspects of microbe profiling systems for generating a microbe profile using a mask or a mouthpiece are described in U.S. patent application Ser. Nos. 13/975,055, 13/975,067, and 13/975,079, each of which is incorporated herein by reference.

In an aspect, system 100 includes circuitry configured to receive the information associated with the microbe profile of the individual from a microbe profiling system that includes a kiosk. For example, system 100 can include circuitry configured to receive the information associated with a microbe profile of an individual from a kiosk in a commercial space, the kiosk configured to dispense one or more microbe sampling units (e.g., swabs), analyze the microbe sampling units with at least one sensor component (e.g., a spectrophotometer) after the individual has sampled a skin surface, and generate a microbe profile of the individual with a computing component. In an aspect, system 100 includes circuitry configured to receive the information associated with the microbe profile of the individual from a microbe profiling system that includes a kit. For example, system 100 can include circuitry configured to receive the information associated with a microbe profile of an individual from an at-home kit, the kit including at least one microbe sampling unit, e.g., a peelable mask with a microbe capture region, and an analyzer with at least one sensor component, e.g., an optical scanner, a user interface, and a computing component. Other non-limiting aspects of a kiosk or kit for sampling a skin surface and generating a microbe profile are described in U.S. patent application Ser. No. 14/255,653.

In an aspect, circuitry of 140 of system 100 includes circuitry 420 configured to receive the information associated with the microbe profile of the individual from a computing component associated with at least one of a microbe profiling device or a microbe profiling system. For example, the computing component of the microbe profiling device or the microbe profiling system can include circuitry configured to receive sensor output from at least one sensor component of the microbe profiling device or microbe profiling system, the sensor output including information associated with at least one property, e.g., at least one optical, fluorescence, magnetic, acoustic, electrical, electromagnetic, or radiofrequency property, of the detected one or more signals emitted or reflected from the microbe-capture region of the microbe sampling unit; circuitry configured to compare the at least one property of the detected one or more signals emitted or reflected from the microbe-capture region of the microbe sampling unit with a reference dataset of signal properties; and circuitry configured to generate a microbe profile of the individual based on the comparison with the reference dataset of signal properties.

In an aspect, system 100 includes circuitry configured to receive the information associated with the microbe profile of the individual from a computing component associated with at least one of a microbe profiling device or a microbe profiling system through a wireless communication. The wireless communication means can include any of a number of wireless implementations, devices, and standards, non-limiting examples of which include cellular networks, e.g., 3G, short-range point-to-point communication, e.g., wireless USB, wireless sensor networks, e.g., Bluetooth, or wireless LAN, e.g., Wi-Fi. For example, system 100 can include circuitry configured to receive the information associated with the microbe profile of an individual via a cellular network communication. In an aspect, system 100 includes circuitry configured to receive the information associated with the microbe profile of the individual from a computing component associated with at least one of a microbe profiling device or a microbe profiling system through a wired communication, e.g., a cable, phone, or Internet connection, provided by a telephone, cable, or fiber-optic network. In an aspect, system 100 includes circuitry configured to receive the information associated with the microbe profile from a computing component associated with a hand-held microbe profiling device or an analyzer of a microbe profiling kit. For example, system 100 can include circuitry configured to receive the information associated with the microbe profile of the individual from a hand-held microbe profiling device or a microbe profiling kit used in a home environment and capable of communicating through a cellular network to a computing device associated with a cosmetic supplier and/or manufacturer. For example, system 100 can include circuitry configured to receive the information associated with the microbe profile of the individual from a kiosk or microbe profiling system associated with a medical or commercial space and capable of communicating through a telephone or cable connection with a computing device associated with a cosmetic supplier and/or manufacturer.

In an aspect, circuitry 140 of system 100 includes circuitry 430 configured to receive the information associated with the microbe profile of the individual from a portable data storage device. For example, the microbe profile of the individual can be generated using a microbe profiling device or system and the microbe profile downloaded to a portable data storage device and uploaded to computing device 120. Non-limiting examples of portable data storage devices have been described above herein.

In an aspect, circuitry 140 of system 100 includes circuitry 440 configured to receive the information associated with the microbe profile of the individual from the Internet. In an aspect, the microbe profile of the individual is downloaded from a microbe profiling device, microbe profiling system, and/or portable data storage device to the Internet, e.g., a specific client website, and then uploaded from the Internet onto computing device 120. For example, system 100 can include circuitry configured to receive the microbe profile of an individual from an Internet site to which the individual has downloaded his/her microbe profile. For example, the microbe profile may be downloaded to an Internet site as part of a user interaction at a medical or commercial kiosk, or through an analyzer as part of an at-home profiling kit.

FIG. 5 illustrates further aspects of a system 100. System 100 includes circuitry 150 configured to receive information associated with an ingredient list 500 of the cosmetic product, the ingredient list including one or more cosmetic ingredients. For example, the ingredient list can include the list of cosmetic ingredients printed on the label of a cosmetic product. For example, the ingredient list can include a dataset of cosmetic ingredients commonly used in cosmetic products. For example, the ingredient list can include a dataset of cosmetic ingredient lists of a plurality of cosmetic products. For example, the ingredient list can include a list of cosmetic products and a corresponding list of the cosmetic ingredients included in each of the listed cosmetic products. For example, the ingredient list can include a dataset that includes any of a number of GRAS (Generally Regarded As Safe) ingredients as outlined under sections 201(s) and 409 of the Federal Food, Drug, and Cosmetic Act.

In an aspect, the one or more cosmetic ingredients in the ingredient list of the cosmetic product include at least one of the one or more reference cosmetic ingredients in the ingredient-microbe interaction dataset. In an aspect, the ingredient list 500 of the cosmetic product includes at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax, as shown in block 510. In an aspect, the one or more ingredients in the cosmetic product include at least one of one or more probiotic agents, one or more prebiotic agents, or one or more therapeutic agents 520. Non-limiting examples of cosmetic ingredients have been described above herein.

In an aspect, the cosmetic product includes a product formulated for topical use. In an aspect, the cosmetic product includes at least one of a liquid, a solid, a semisolid, or aerosol. In an aspect, the cosmetic product includes a topical product that is a solution, emulsion, or colloidal dispersion of one or more ingredients in an aqueous or nonaqueous (oily) vehicle. In an aspect, the cosmetic product can include a mineral oil. In an aspect, the cosmetic product can include a semisolid ointment. For example, the cosmetic product can include a water-in-oil emulsion, an oil-in-water emulsion, or a petroleum-based ointment with limited amounts of aqueous component. In an aspect, the cosmetic product can include a wax. In an aspect, the cosmetic product can include a powder. In an aspect, the cosmetic product can include a mineral-based powder. In an aspect, the cosmetic product can include a natural or synthetic polymer, e.g., methylcellulose, silicone, or latex. In an aspect, the cosmetic product includes at least one of a primer, a concealer, a foundation, or a bronzer. In an aspect, the cosmetic product includes a lip product, e.g., lipstick, lip balm, lip gloss, lip liner, lip plumper, or lip conditioner. In an aspect, the cosmetic product includes rouge, blush, or blusher. In an aspect, the cosmetic product includes mascara, eyeliner, or eyebrow pencils, creams, waxes, gels or powders. In an aspect, the cosmetic product includes stage makeup. In an aspect, the cosmetic product includes a moisturizer, an anti-aging cream, a mask or peel, an exfoliant, a toner, or a sunscreen. In an aspect, the cosmetic product includes a deodorant, a shaving cream, or an aftershave cream or lotion. In an aspect, the cosmetic product includes a hair care product, e.g., a shampoo, conditioner, mousse, gel, hairspray, setting product, or hair colorant.

In an aspect, the ingredient list of the cosmetic product is stored in at least one of a memory component of computing device 120, a portable data storage device, or a remoter server, as shown in block 530. For example, computing device 120 can be delivered to a user, e.g., the individual or other individual, with the ingredient list loaded into a memory component of the computing device. In an aspect, circuitry 150 includes circuitry 540 configured to receive the information associated with the ingredient list of the cosmetic product from a remote computing device. For example, the system can include circuitry configured to receive the information associated with the ingredient list of the cosmetic product from a personal computing device, e.g., the individual's smart phone. In an aspect, circuitry 540 includes circuitry 550 configured to receive the information associated with the ingredient list of the cosmetic product from at least one of a cosmetic distributer, a cosmetic manufacturer, or a cosmetic formulary. For example, the system can include circuitry configured to receive the ingredient list from a cosmetic manufacturer manufacturing the cosmetic product at issue. In an aspect, the remote computing device includes a remote server accessible to computing device 120. For example, ingredient list 110 may be stored on a remote computing device associated with a cosmetic supplier and accessible to computing device 120 through a web-based connection. In an aspect, ingredient list 110 is stored on a cloud-based server. In an aspect, the remote computing device includes a personal computing device, e.g., a home computer, a tablet, or smart phone. In an aspect, circuitry 150 includes circuitry 570 configured to receive the information associated with the ingredient list of the cosmetic product from the Internet.

In an aspect, the ingredient list of the cosmetic product is stored on a portable data storage device. In an aspect, circuitry 150 includes circuitry 560 configured to receive the information associated with the ingredient list of the cosmetic product from a portable data storage device. For example, the ingredient list of a cosmetic product may be provided on a portable flash drive. Non-limiting examples of portable data storage devices have been described above herein. In an aspect, computing device 120 includes a port or docking site sized to accept a portable data storage device including the ingredient list of the cosmetic product and circuitry configured to access the ingredient list from the inserted or docked portable data storage device.

In an aspect, the ingredient list of the cosmetic product is updatable. In an aspect, circuitry 150 includes circuitry configured to receive information associated with an updated ingredient list of the cosmetic product. For example, the ingredient list of the cosmetic product is updatable in response to changes (e.g., additions and/or subtractions) of one or more cosmetic ingredients in the ingredient list of the cosmetic product. In an aspect, updates to the ingredient list are accessible to the computing device of the system through a web-based communication link, e.g., through the Internet, or through delivery of a portable data storage device, e.g., a memory card, including an updated ingredient list.

In an aspect, the computing device of the system includes circuitry configured to receive the information associated with the ingredient list of the cosmetic product through a user interface. For example, the individual or other user may manually enter the one or more cosmetic ingredients in the ingredient list of the cosmetic product into the computing device using a user interface, e.g., a keyboard, touch pad, microphone, or the like.

In an aspect, the ingredient list of the cosmetic product is entered into the computing device by way of scanning device. FIG. 6 illustrates aspects of system 100 including scanning device 600. In an aspect, scanning device 600 is operably coupled to computing device 120 and includes circuitry 610 configured to scan and digitize an ingredient label of the cosmetic product, the ingredient label including the ingredient list of the cosmetic product. In an aspect, scanning device 600 includes an optical scanning device, e.g., an optical character recognition scanning device for scanning text. In an aspect, scanning device 600 includes a barcode reader. For example, the scanning device can include a barcode reader for reading a barcode, e.g., a linear or matrix barcode, associated with the cosmetic product, the barcode including the ingredient list of the cosmetic product. Non-limiting examples of barcode readers include pen-type readers, laser scanners, charged-coupled device (CCD) readers, camera-based readers, video camera readers, and omnidirectional barcode readers. In an aspect, scanning device 600 includes a radiofrequency identification (RFID) tag reader. In an aspect, scanning device 600 includes an active RFID tag reader. In an aspect, scanning device 600 includes a passive RFID tag reader. For example, the scanning device can include a passive RFID tag reader for reading a passive RFID tag associated with the cosmetic product, the passive RFID tag including the ingredient list of the cosmetic product.

FIG. 7 illustrates further aspects of system 100. System 100 includes circuitry 160 configured to compare the received information associated with the microbe profile of the individual and the receive information associated with the ingredient list of the cosmetic product to the ingredient-microbe interaction dataset. In an aspect, system 100 includes circuitry 700 configured to compare the one or more types of microbes in the microbe profile of the individual to the one or more types of reference microbes in the ingredient-microbe interaction dataset. For example, system 100 can include circuitry configured to compare an identified type of microbe, e.g., *Propionibacterium* or *Staphylococcus*, in the microbe profile of the individual to the one or more types of reference microbes to determine any interactions of the identified type of microbe with the one or more reference cosmetic ingredients and by extension, the one or more cosmetic ingredients in the ingredient list of the cosmetic product. In an aspect, system 100 includes circuitry 710 configured to compare the one or more cosmetic ingredients in the ingredient list of the cosmetic product to the one or more reference cosmetic ingredients in the ingredient-microbe interaction dataset. For example, system 100 can include circuitry configured to compare a cosmetic ingredient, e.g., stearic acid, in the ingredient list of the cosmetic product to the one or more reference cosmetic ingredients to determine any interactions of the cosmetic ingredient with the one or more types of reference microbes and by extension, the one or more types of microbe in the microbe profile of the individual.

System 100 includes circuitry 170 configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more ingredients in the cosmetic product. In an aspect, circuitry 170 includes circuitry 720 configured to identify the potential effect on the at least one of the one or more cosmetic ingredients in the ingredient list of the cosmetic product in response to at least one of the one or more types of microbes in the microbe profile of the individual. In an aspect, circuitry 720 includes circuitry 730 configured to identify a potential color effect on the at least one of the one or more cosmetic ingredients in the ingredient list of the cosmetic product in response to at least one of the one or more types of microbes in the microbe profile of the individual. For example, the system can include circuitry configured to identify an interaction of one or more chromogenic substrates in the cosmetic product that might interact with the one or more types of microbes in the microbe profile of the individual. For example, the system can include circuitry configured to identify an interaction of one or more pH sensitive pigments in the cosmetic product that might interact with pH changes caused by the one or more types of microbes in the microbe profile of the individual.

In an aspect, circuitry 720 include circuitry 740 configured to identify a potential texture effect on the at least one of the one or more cosmetic ingredients in the ingredient list of the cosmetic product in response to at least one of the one or more types of microbes in the microbe profile of the individual. For example, the system can include circuitry configured to identify one or more cosmetic ingredients (e.g., emulsifiers or emollients) in the cosmetic product that are metabolized or assimilated by the one or more types of microbes in the microbe profile that can result in a change in texture, e.g., "silkiness" or "smoothness" of the cosmetic product.

In an aspect, circuitry 720 includes circuitry 750 configured to identify a potential pH effect on the at least one of the one or more cosmetic ingredients in the ingredient list of the cosmetic product in response to at least one of the one or more types of microbes in the microbe profile of the individual. For example, the system can include circuitry configured to identify at least one potential pH effect induced by the presence of a particular type of bacteria, e.g., lactic acid producing species of *Lactobacilli*.

In an aspect, circuitry 720 includes circuitry 760 configured to identify a potential odor effect on the at least one of the one or more cosmetic ingredients in the ingredient list of the cosmetic product in response to at least one of the one or more types of microbes in the microbe profile of the individual. For example, the system can include circuitry configured to identify at least one odor effect caused by metabolism or degradation of one or more of the cosmetic ingredients in the presence of one or more types of microbes in the microbe profile of the individual.

System 100 includes circuitry 180 configured to recommend a modification to the ingredient list of the cosmetic in response to the identified interaction. FIG. 8 illustrates further aspects of system 100. In an aspect, circuitry 180 of system 100 includes circuitry 800 configured to recommend a modification to the ingredient list of the cosmetic product to alleviate the identified interaction. In an aspect, the system includes circuitry configured to recommend a modification to the ingredient list of the cosmetic product to lessen the identified interaction between the at least one of the one or more cosmetic ingredients in the ingredient list of the cosmetic product and the at least one of the one or more types of microbes in the microbe profile of the individual. In an aspect, the system includes circuitry configured to recommend a modification to the ingredient list of the cosmetic product to eliminate the identified interaction between the at least one of the one or more cosmetic ingredients in the ingredient list of the cosmetic product and the at least one of the one or more types of microbes in the microbe profile of the individual. In an aspect, the system includes circuitry configured to recommend a modification to the ingredient list of the cosmetic product to alleviate the potential effect on the at least one of the one or more cosmetic ingredients. In an aspect, the system includes circuitry configured to recommend a modification to the ingredient list of the cosmetic product to alleviate at least one of a potential color effect, a potential texture effect, a potential pH effect, or a potential odor effect on the at least one of the one or more cosmetic ingredients.

In an aspect, circuitry 180 of system 100 includes circuitry 810 configured to recommend a modification to the ingredient list of the cosmetic product to enhance the identified interaction. In an aspect, the system includes circuitry configured to recommend a modification to the ingredient list of the cosmetic product to enhance the identified interaction between the at least one or more the or more cosmetic ingredients in the ingredient list of the cosmetic product and the at least one of the one or more types of microbes in the microbe profile of the individual. In an aspect, the system includes circuitry configured to recommend a modification to the ingredient list of the cosmetic product to enhance a potential effect on the at least one of the one or more cosmetic ingredients. In an aspect, the system includes circuitry configured to recommend a modification to the ingredient list of the cosmetic product to enhance at least one of a potential color effect, a potential texture effect, a potential pH effect, or a potential odor effect on the at least one of the one or more cosmetic ingredients. For example, based on an individual's preference, the system may include circuitry configured to identify potential color effects that are intensified in the presence of specific skin-associated microbes. For example, the system can include circuitry configured to add or subtract at least one of the one or more cosmetic ingredients from the cosmetic product to enhance an interaction, e.g., to enhance a color effect.

In an aspect, circuitry 180 of system 100 includes circuitry 820 configured to recommend an addition of at least one cosmetic ingredient to the ingredient list of the cosmetic product. In an aspect, the system includes circuitry configured to recommend an addition of at least one cosmetic ingredient to the ingredient list of the cosmetic product to alleviate or enhance a potential effect on the at least one of the one or more cosmetic ingredients in the ingredient list of the cosmetic product. In an aspect, the system includes circuitry configured to recommend an addition of at least one cosmetic ingredient to the ingredient list of the cosmetic product to alleviate or enhance at least one of a potential color effect, a potential texture effect, a potential pH effect, or a potential odor effect on the at least one of the one or more cosmetic ingredients in the ingredient list of the cosmetic product. For example, the system can include circuitry configured to recommend addition of a buffering agent to alleviate or enhance a potential pH effect. For example, the system can include circuitry configured to recommend addition of a chromogenic substrate to alleviate or enhance a potential color effect. For example, the system can include circuitry configured to recommend addition of one or more antimicrobial agents to kill or inhibit growth of one or more types of microbes in the microbe profile of the individual that might contribute to degradation of one or more cosmetic ingredients in the ingredient list of the cosmetic product, leading to a potential texture effect and/or an potential odor effect.

In an aspect, circuitry 180 of system 100 includes circuitry 830 configured to recommend a subtraction of at least one cosmetic ingredient from the ingredient list of the cosmetic product. In an aspect, the system includes circuitry configured to recommend a subtraction of at least one cosmetic ingredient from the ingredient list of the cosmetic product to alleviate or enhance a potential effect on the at least one of the one or more cosmetic ingredients in the ingredient list of the cosmetic product. In an aspect, the system includes circuitry configured to recommend a subtraction of at least one cosmetic ingredient from the ingredient list of the cosmetic product to alleviate or enhance at least one of a potential color effect, a potential texture effect, a potential pH effect, or a potential odor effect on the at least one of the one or more cosmetic ingredients in the ingredient list of the cosmetic product. For example, the system can include circuitry configured to subtract a cosmetic ingredient from the cosmetic product that is susceptible to degradation and/or metabolism by one or more types of microbes in the microbe profile of the individual. For example, the system can include circuitry configured to subtract a potential reactive cosmetic ingredient from the ingredient list and to add a relatively inert cosmetic ingredient, e.g., a cosmetic ingredient not known to be a metabolic or enzymatic substrate for any of the one or more types of microbes in the microbe profile of the individual.

In an aspect, circuitry 180 of system 100 includes circuitry 840 configured to recommend a relative change in concentration of at least one cosmetic ingredient in the ingredient list of the cosmetic product. In an aspect, the system includes circuitry configured to recommend a relative change in concentration of at least one cosmetic ingredient in the ingredient list of the cosmetic product to alleviate or enhance a potential effect on the at least one of the one or more cosmetic ingredients in the ingredient list of the cosmetic product. In an aspect, the system includes circuitry configured to recommend a relative change in concentration of at least one cosmetic ingredient in the ingredient list of the cosmetic product to alleviate or enhance at least one of a potential color effect, a potential texture effect, a potential pH effect, or a potential odor effect on the at least one of the one or more cosmetic ingredients in the ingredient list of the cosmetic product.

FIG. 9 illustrates further aspects of system 100. In an aspect, system 100 includes user interface 900. User interface 900 can include any of a number of input or output components configured to allow a user, e.g., the individual, to enter data, e.g., user information, and to receive data, e.g., the recommended modifications to the ingredient list of the cosmetic product. Non-limiting examples of user interfaces include a graphical user interface, a display, a keyboard, a keypad, a trackball, a joystick, a touch-screen, a mouse, a switch, a dial, a button, a microphone, a speaker, a printer, and or any other component that allows for input/output interactions between a user and a computing device.

In an aspect, system 100 further includes circuitry 910 configured to receive user information from the individual. In an aspect, system 100 includes circuitry configured to receive the user information from the individual through user interface 900, e.g., a touchscreen display, a keyboard, or a microphone. In an aspect, system 100 includes circuitry configured to receive the user information from a remote source, e.g., a personal computing device, an Internet site, or a computing component associated with a microbe profiling device, microbe profiling system, microbe profiling kit, or microbe profiling kiosk. In an aspect, system 100 includes circuitry 920 configured to receive at least one of age, gender, ethnicity, geographical location, skin characteristics, medical history, co-morbidities, or user preferences.

In an aspect, system 100 includes circuitry 930 configured to recommend the modification to the ingredient list of the cosmetic product based at least in part on user information. In an aspect, system 100 includes circuitry 940 configured to recommend the modification to the ingredient list of the cosmetic product based at least in part on at least one of age, gender, ethnicity, geographical location, skin characteristics, medical history, co-morbidities, or user preferences. For example, the age of a user, e.g., young versus old, may dictate the types of microbes present on a given body surface. See, e.g., Yatsunenko et al. (2012) *Nature* 486:222-227 and Oh et al. (2012) *Genome Medicine* 4:77, which are incorporated herein by reference. For example, the ethnicity and/or geographical location of the user may dictate the types of microbes present on a given body surface. See, e.g., Mason et al. (2013) *PLoSONE* 8(10):e77287 and Shetty et al. (2013) *Microbiome* 1:24, which are incorporated herein by reference. For example, a skin characteristic such as whether the skin surface is sebaceous, moist, or dry may dictate the types of microbes present on said skin surface. See, e.g., Grice et al. (2009) *Science* 324:1190-1192. In an aspect, the skin characteristics may dictate which vehicle (cream, gel, lotion, or solution) is appropriate for a skin type. For example, creams may be appropriate for users with sensitive or dry skin, but too "oily" for users with oily skin; user's with oily skin may be more comfortable with gels which have drying effects, but may prevent cosmetics from adhering; lotions may be used for all skin types, but may also have burning or drying effects; and solutions, e.g., solutions of antimicrobials, are often dissolved in alcohol, which may dry the skin.

In an aspect, circuitry 940 includes circuitry configured to recommend a modification to the ingredient list of the cosmetic product based at least in part on a user preference. For example, the user preference can include a preferred color, texture, pH, or odor. For example, the user preference can include adding or subtracting a cosmetic ingredient from the ingredient list of the cosmetic product to cause a certain interaction with the individual's microbes. For example, the individual may prefer a red hue caused by the interaction of a specific cosmetic ingredient in the cosmetic product with a specific type of microbe on the skin surface of the individual. For example, the individual may prefer an odor caused by the interaction of a specific cosmetic ingredient in the cosmetic product with a specific type of microbe on the skin surface of the individual.

System 100 further includes circuitry 190 configured to report to a user the recommended modification to the ingredient list of the cosmetic product. In an aspect, the user includes the individual for whom the microbe profile was generated. In an aspect, the user includes a second individual, e.g., a medical practitioner, a healthcare worker, a pharmacist, a cosmetologist, a technician, merchant, a supplier, or a manufacturer. In an aspect, the user includes a computing device associated with a medical or commercial entity, e.g., a supplier or manufacturer of cosmetic goods. In an aspect, the user includes at least one of a website, a social media site, or a personal computing instrument, e.g., a smart phone. In an aspect, the user includes a computing device associated with a formulation or filling device, the formulation or filling device configured to modify the cosmetic product by adding and/or subtracting one or more ingredients from a cosmetic product based on the recommended modification to the ingredient list.

In an aspect, system 100 includes circuitry 950 configured to report to the user the recommended modification to the ingredient list of the cosmetic product on a display associated with a computing device, e.g., computing device 120. For example, the individual may be interacting with a computing device associated with a kiosk in a commercial center, the kiosk including a display for outputting information including the recommended modification to the ingredient list of the cosmetic product. In an aspect, system 100 includes circuitry 960 configured to report to the user the recommended modification to the ingredient list of the cosmetic product through a printout. For example, the individual or other user may receive a printout including the recommended modification to the ingredient list of the cosmetic product from a printer operably coupled to a computing device, e.g., computing device 120. In an aspect, system 100 includes circuitry 970 configured to report to the user the recommended modification to the ingredient list of the cosmetic product through at least one of a telephone call, a text message, or an e-mail. For example, an individual may receive an automated phone, text, or e-mail message in which the recommended modification to the ingredient list is provided to the individual. In an aspect, system 100 includes circuitry 980 configured to report the recommended modification to the ingredient list of the cosmetic product to a remote computing device. In an aspect, the remote computing device can include an individual's personal computing device, e.g., a smart phone or tablet. In an aspect, the remote computing device can include a computing device associated with a supplier and/or a manufacturer of cosmetic products. For example, the system can include circuitry configured to report the recommended modification to the ingredient list of the cosmetic product to a remote computing device operably coupled to a formulating and/or filling apparatus. For example, the system can include circuitry configured to generate the recommended modification to the ingredient list of the cosmetic product based on an individual's microbe profile using a computing device at a medical practice or cosmetic counter and circuitry configured to report the recommended modification to the ingredient list of the cosmetic product to a second computing device associated with a cosmetic supplier and/or manufacturer.

In an aspect, system 100 further includes circuitry 985 configured to provide to the individual at least one discount coupon for purchase of a modified cosmetic product including the recommended modification to the ingredient list. In an aspect, circuitry 985 is configured to provide a printed discount coupon to the individual. In an aspect, circuitry 985 is configured to provide the discount coupon electronically to the individual's smart phone or to a computing device. In an aspect, circuitry 985 is configured to provide the discount coupon as a discount code for use in making a purchase through the Internet or other web-based system.

In an aspect, system 100 further includes circuitry 990 configured to arrange for delivery of a modified cosmetic product including the recommended modification to the ingredient list. For example, the circuitry can be configured to arrange for delivery of the modified cosmetic by way of the Postal Service, a shipping service, e.g., FedEx or UPS, or a courier. In an aspect, system includes circuitry configured to automatically arrange for delivery of the modified cosmetic product. For example, the circuitry can be configured to automatically arrange for delivery of the modified cosmetic product by transmitting a request to a cosmetic supplier and/or manufacturer to reformulate the cosmetic product, label the modified cosmetic product for shipment, and load the modified cosmetic product for delivery. In an aspect, the system includes circuitry configured to arrange for the delivery of the modified cosmetic product to a street address, e.g., a street address of at least one of the individual's residence or workplace or a street address of at least one of a medical practice, pharmacy, or retail store for pick up by the individual. In an aspect, the system includes circuitry configured to arrange for delivery of the modified cosmetic product to a postal address, e.g., a post office box. In an aspect, the system includes circuitry configured to arrange for delivery of the modified cosmetic product to a residence, a post office, a delivery service office, a store, a pharmacy, a medical office, or a cosmetic counter.

In an aspect, system 100 further includes circuitry configured to notify the individual that delivery of the modified cosmetic product has been arranged. In an aspect, the system includes circuitry configured to notify the individual by at least one of an electronic communication, a telephonic communication, or a written communication. For example, the circuitry can be configured to notify the individual by way of an e-mail communication or a text message. For example, the circuitry can be configured to notify the individual by way of an automated telephone call. For example, the circuitry can be configured to notify the individual by way of a postcard or letter sent through the mail.

Method

With reference to FIG. 10, shown is a flowchart of a method of modifying a cosmetic product. The method includes receiving information associated with a microbe profile of an individual, the microbe profile including a distribution of one or more types of microbes on a skin surface of the individual, as shown in block 1000; receiving information associated with an ingredient list of the cosmetic product, the ingredient list of the cosmetic product including one or more cosmetic ingredients, as shown in block 1010; comparing the received information associated with the microbe profile of the individual and the received information associated with the ingredient list of the cosmetic product to an ingredient-microbe interaction dataset, the ingredient-microbe interaction dataset including information associated with interactions between one or more reference cosmetic ingredients and one or more types of reference microbes, as shown in block 1020; identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients, as shown in block 1030; recommending a modification to the ingredient list of the cosmetic in response to the identified interaction, as shown in block 1040; and reporting to the user the recommended modification to the ingredient list of the cosmetic product, as shown in block 1050.

In an aspect, a method of modifying a cosmetic product, such as described in FIG. 10, is implemented on a computing device. In an aspect, the method is implemented on a home computing device. In an aspect, the method is implemented on a computing device associated with a medical practice or a commercial site, e.g., a cosmetic counter. In an aspect, the method is implemented on a computing device associated with a cosmetic supplier, a cosmetic distributer, and/or a cosmetic manufacturer. In an aspect, the method is implemented on a computing device associated with a microbe profiling device. In an aspect, the method is implemented on a computing device associated with a microbe profiling system. In an aspect, the method is implemented on a computing device associated with a kiosk, e.g., a cosmetic dispensing kiosk associated with a medical practice or a commercial site.

The method of FIG. 10 includes receiving information associated with a microbe profile of an individual, the microbe profile including a distribution of one or more types of microbes on a skin surface of the individual. In an aspect, the microbe profile of the individual includes a spatial distribution of one or more types of microbes on a skin surface of the individual. For example, the method can include receiving information associated with a microbe profile of the individual that includes a spatial distribution of one or more types of microbes on a skin surface associated with the face, neck, head, scalp, torso, buttocks, upper extremities, lower extremities, or genital regions of the individual. For example, the method can include receiving information associated with a microbe profile of the individual that includes a spatial distribution of a first type of microbe, e.g., a first type of bacteria, relative to a spatial distribution of a second type of microbe, e.g., a second type of bacteria. In an aspect, the method includes receiving information associated with a microbe profile of an individual including the identity of one or more types of microbes on the skin surface of the individual. In an aspect, the method includes receiving information associated with a microbe profile of an individual including a spatial distribution of one or more types of bacteria, fungus, virus, parasite, archaea, or small arthropod (e.g., mites) on the skin surface of the individual. In an aspect, the method includes receiving information associated with a microbe profile of an individual including at least one type of mutualistic microbe, commensal microbe, or pathogenic microbe. In an aspect, the method includes receiving information associated with a microbe profile of an individual including at least one type of introduced microbe, e.g., a probiotic or genetically engineered microbe. In an aspect, the method includes receiving information associated with a microbe profile of an individual including at least one type of resident microbe, e.g., at least one type of skin-resident microbe.

FIG. 11 illustrates further aspects of a method such as shown in FIG. 10. In an aspect, the method includes receiving the information associated with the microbe profile of the individual from a microbe profiling device, as shown in block 1100. For example, the method can include receiving the information associated with the microbe profile of the individual from a hand-held microbe profiling device through a wireless communication. In an aspect, the method includes receiving the information associated with the microbe profile of the individual from a microbe profiling system, as shown in block 1110. For example, the method can include receiving the information associated with the microbe profile of the individual from a microbe profiling kiosk located in a shopping mall or a cosmetic store. Non-limiting aspects of microbe profiling devices and systems have been described above herein.

In an aspect, the method includes receiving the information associated with the microbe profile of the individual from a computing component associated with at least one of a microbe profiling device or a microbe profiling system, as shown in block 1120. In an aspect, the method includes receiving the information associated with the microbe profile of the individual from a computing component associated with at least one of a microbe profiling device or a microbe profiling system through a wireless communication. For example, the method can include receiving the information associated with the microbe profile of an individual via a cellular network communication. In an aspect, the method includes receiving the information associated with the microbe profile of the individual from a computing component associated with a computing component associated with at least one of a microbe profiling device or a microbe profiling system through a wired communication, e.g., a fiber-optic network. In an aspect, the method includes receiving the information associated with the microbe profile from a computing component associated with a hand-held microbe profiling device or an analyzer of a microbe profiling kit. For example, the method can include receiving the information associated with the microbe profile of the individual from a hand-held microbe profiling device or a microbe profiling kit used in a home environment and capable of communicating through a cellular network to a computing device associated with a cosmetic supplier and/or manufacturer. For example, the method can include receiving the information associated with the microbe profile of the individual from a kiosk or microbe profiling system associated with a medical or commercial space and capable of communicating through a telephone or cable connection with a computing device associated with a cosmetic supplier and/or manufacturer.

In an aspect, the method includes receiving the information associated with the microbe profile of the individual from a portable data storage device, as shown in block 1130. For example, the microbe profile of the individual can be generated using a microbe profiling device or system, downloaded to a portable data storage device, and uploaded to a computing device, e.g., a computing device for performing the method. Non-limiting examples of portable data storage devices have been describe above herein.

In an aspect, the method includes receiving the information associated with the microbe profile of the individual from at least one of a remote computing device, a remote server, or the Internet, as shown in block 1140. In an aspect, the microbe profile of the individual is downloaded from a microbe profiling device, microbe profiling system, and/or portable data storage device to the Internet, e.g., a specific client website, and then uploaded from the Internet onto a computing device for performing the method. For example, the method can include receiving the microbe profile of an individual from an Internet site to which the individual downloaded his/her microbe profile. For example, the microbe profile may be downloaded to an Internet site as part of a user interaction at a medical or commercial kiosk, or through an analyzer as part of an at-home profiling kit.

In an aspect, the method includes receiving the information associated with the microbe profile of the individual with a computing device. In an aspect, the method includes receiving the information associated with the ingredient list of the cosmetic product with a computing device. In an aspect, the computing device includes a computing device associated with a business, e.g., retail, wholesale, and/or manufacturing business. In an aspect, the computing device includes a computing component of a microbe profiling device or the microbe profiling system. For example, the method can include receiving the microbe profile and the ingredient list of the cosmetic product with the computing component of a hand-held microbe profiling device, the computing component of the hand-held microbe profiling device further configured to compare the microbe profile and the ingredient list with at least one ingredient-microbe interaction dataset, identify interactions between at least one ingredient of a cosmetic product and at least one of the one or more types of microbes in the microbe profile, recommend a modification to the ingredient list of the cosmetic product, and report the recommended modification to the individual.

FIG. 12 shows further aspects of the method. The method includes receiving information associated with an ingredient list of the cosmetic product. In an aspect, the method includes receiving information associated with the one or more cosmetic ingredients in the ingredient list of the cosmetic product, as shown in block 1200. In an aspect, the method includes receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax in the ingredient list of the cosmetic product, as shown in block 1210. In an aspect, the method includes receiving information associated with at least one of one or more probiotic agents, one or more prebiotics agents, or one or more therapeutic agents in the ingredient list of the cosmetic product, as shown in block 1220. In an aspect, the method includes receiving the information associated with the ingredient list of the cosmetic product from a remote source, as shown in block 1230. In an aspect, the method includes receiving the information associated with the ingredient list of the cosmetic product from a cosmetic distributer, a cosmetic manufacturer, or a cosmetic formulary, as shown in block 1240. In an aspect, the method includes receiving the information associated with the ingredient list of the cosmetic product from a portable data storage device, as shown in block 1250. In an aspect, the method includes receiving the information associated with the ingredient list of the cosmetic product from a scanning device, as shown in block 1260.

The method of FIG. 10 includes comparing the received information associated with the microbe profile of the individual and the received information associated with the ingredient list of the cosmetic product to the ingredient-microbe interaction dataset, the ingredient-microbe interaction dataset including information associated with interactions between one or more reference cosmetic ingredients and one or more types of reference microbes, as shown in block 1020. In an aspect, the ingredient-microbe interaction dataset is stored in a memory component of a computing device used for performing the method. In an aspect, the ingredient-microbe interaction dataset is accessed from a remote computing device or remote server through a web or Internet connection. In an aspect, the ingredient-microbe interaction dataset is stored on a portable data storage device, e.g., a CD ROM or a memory card or stick.

FIG. 13 illustrates further aspects of a method such as shown in FIG. 10. In an aspect, the method includes comparing the one or more types of microbes in the microbe profile of the individual to the one or more types of reference microbes in the ingredient-microbe interaction dataset, as shown in block 1300. For example, the method can include comparing an identified type of microbe, e.g., *Staphylococcus epidermidis*, to the reference microbes to identify any interactions of the identified type of microbe with the one or more reference cosmetic ingredients. In an aspect, the method includes comparing the one or more cosmetic ingredients in the ingredient list of the cosmetic product with the one or more reference cosmetic ingredients in the ingredient-microbe interaction dataset, as shown in block 1310. For example, the method can include comparing a cosmetic ingredient, e.g., stearic acid, in the ingredient list of the cosmetic product to the one or more reference cosmetic ingredients to identify any interactions of the cosmetic ingredient with one more types of reference microbes.

The method further includes identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients. For example, the method can include identifying an interaction between a cosmetic ingredient in a cosmetic product with a type of microbe in the microbe profile of the individual from the comparison of the microbe profile and the ingredient list of the cosmetic product to the ingredient-microbe interaction dataset, the interaction having a potential effect on one or more properties of the cosmetic ingredient. In an aspect, the method includes identifying the potential effect on the at least one of the one or more cosmetic ingredients in the ingredient list of the cosmetic product in response to at least one of the one or more types of microbes in the microbe profile of the individual, as shown in block 1320. In an aspect, the method includes identifying a potential color effect on the at least one of the one or more cosmetic ingredients in the ingredient list of the cosmetic product, as shown in block 1330. For example, the method can include identifying a potential color effect caused by the interaction of a chromogenic substrate in the cosmetic product and a type of microbe in the microbe profile of the individual. For example, the method can include identifying a potential color effect caused by the interaction of a pH sensitive pigment or dye in the cosmetic product a type of microbe in the microbe profile of the individual.

In an aspect, the method includes identifying a potential texture effect on the at least one of the one or more cosmetic ingredients in the ingredient list of the cosmetic product, as shown in block 1340. For example, the method can include identifying one or more cosmetic ingredients, e.g., emulsifiers or emollients, in the cosmetic product that are metabolized or assimilated by the one or more types of microbes in the microbe profile that can result in a change in texture, e.g., "silkiness" or "smoothness" of the cosmetic product.

In an aspect, the method includes identifying a potential pH effect on the at least one of the one or more cosmetic ingredients in the ingredient list of the cosmetic product, as shown in block 1350. For example, the method can include identifying a potential pH effect induced by the presence of a particular type of bacteria, e.g., lactic acid producing species of *Lactobacilli*.

In an aspect, the method includes identifying a potential odor effect on the at least one of the one or more cosmetic ingredients in the ingredient list of the cosmetic product, as shown in block 1360. For example, the method can include identifying a potential odor effect caused by metabolism or degradation of one or more of the cosmetic ingredients in the presence of one or more types of microbes in the microbe profile of the individual.

FIG. 14 illustrates further aspects of a method such as shown in FIG. 10. The method includes recommending a modification to an ingredient list of the cosmetic product in response to the identified interaction, as shown in block 1030. In an aspect, the method includes recommending a modification to the ingredient list of the cosmetic product to alleviate the identified interaction, as shown in block 1400. In an aspect, the method includes recommending a modification to the ingredient list of the cosmetic product to lessen the identified interaction. In an aspect, the method includes recommending a modification to the ingredient list of the cosmetic product to eliminate the identified interaction. In an aspect, the method includes recommending a modification to the ingredient list of the cosmetic product to alleviate the potential effect on the at least one of the one or more cosmetic ingredients in response to the at least one of the one or more types of microbes in the microbe profile of the individual. In an aspect, the method includes recommending a modification to the ingredient list of the cosmetic product to alleviate at least one of a potential color effect, a potential texture effect, a potential pH effect, or a potential odor effect on the at least one of the one or more cosmetic ingredients in response to the at least one of the one or more types of microbes in the microbe profile of the individual.

In an aspect, the method includes recommending a modification to the ingredient list of the cosmetic product to enhance the identified interaction, as shown in block 1410. In an aspect, the method includes recommending a modification to the ingredient list of the cosmetic product to enhance the potential effect on the at least one of the one or more cosmetic ingredients in response to the at least one of the one or more types of microbes in the microbe profile of the individual. In an aspect, the method includes recommending a modification to the ingredient list of the cosmetic product to enhance at least one of a potential color effect, a potential texture effect, a potential pH effect, or a potential odor effect on the at least one of the one or more cosmetic ingredients in response to the at least one of the one or more types of microbes in the microbe profile of the individual. For example, the method can include recommending a modification to the ingredient list of the cosmetic product to make a potential color effect more dramatic. For example, the method can include identifying color interactions that are intensified in the presence of specific skin-associated microbes. For example, the method can include adding or subtracting at least one of the one or more cosmetic ingredients from the cosmetic product to enhance a potential effect, e.g., to enhance a potential color effect, as indicated by the individual's user preferences.

In an aspect, the method includes recommending an addition of at least one cosmetic ingredient to the ingredient list of the cosmetic product in response to the identified interaction, as shown in block 1420. In an aspect, the method includes recommending an addition of at least one cosmetic ingredient to the ingredient list of the cosmetic product to alleviate or enhance the potential effect on the at least one of the one or more cosmetic ingredients in response to the at least one of the one or more types of microbes in the microbe profile of the individual. In an aspect, the method includes recommending an addition of at least one cosmetic ingredient to the ingredient list of the cosmetic product to alleviate or enhance at least one of a potential color effect, a potential texture effect, a potential pH effect, or a potential odor effect on the at least one of the one or more cosmetic ingredients in response to the at least one of the one or more types of microbes in the microbe profile of the individual. For example, the method can include recommending addition of a chromogenic substrate, e.g., indoxyl α-D-glucoside or phenolphthalein phosphate, to induce a potential color effect in response to a specific type of microbe, e.g., *Staphylococcus aureus*. For example, the method can include recommending addition of one or more antimicrobial agents to kill or inhibit growth of one or more types of microbes in the microbe profile of the individual that might contribute to degradation of one or more cosmetic ingredients in the ingredient list of the cosmetic product leading to a potential texture and/or odor effect.

In an aspect, the method includes recommending a subtraction of at least one cosmetic ingredient from the ingredient list of the cosmetic product, as shown in block 1430. In an aspect, the method includes recommending a subtraction of at least one cosmetic ingredient from the ingredient list of the cosmetic product to alleviate or enhance the potential effect on the at least one of the one or more cosmetic ingredients in response to the at least one of the one or more types of microbes in the microbe profile of the individual. In an aspect, the method includes recommending a subtraction of at least one cosmetic ingredient from the ingredient list of the cosmetic product to alleviate or enhance at least one of a potential color effect, a potential texture effect, a potential pH effect, or a potential odor effect on the at least one of the one or more cosmetic ingredients in response to the at least one of the one or more types of microbes in the microbe profile of the individual. For example, the method can include recommending subtraction of oleic acid and/or stearic acid to alleviate over growth of *Candida* or *Pseudomonas*. See, e.g., Yanagi & Onishi (1971) *J. Soc. Cosmet. Chem.* 22:851-865, which is incorporated herein by reference. For example, the method can include recommending subtraction of a potentially reactive cosmetic ingredient with a relatively inert cosmetic ingredient, e.g., a cosmetic ingredient not known to be a metabolic or enzymatic substrate for the one or more types of microbes in the microbe profile of the individual.

In an aspect, the method includes recommending a relative change in concentration of at least one cosmetic ingredient in the ingredient list of the cosmetic product, as shown in block 1440. In an aspect, the method includes recommending a relative change in concentration of at least one cosmetic ingredient in the ingredient list of the cosmetic product to alleviate or enhance the potential effect on the at least one of the one or more cosmetic ingredients in response to the at least one of the one or more types of microbes in the microbe profile of the individual. In an aspect, the method includes recommending a relative change in concentration of at least one cosmetic ingredient to the ingredient list of the cosmetic product to alleviate or enhance at least one of a potential color effect, a potential texture effect, a potential pH effect, or a potential odor effect on the at least one of the one or more cosmetic ingredients in response to the at least one of the one or more types of microbes in the microbe profile of the individual. For example, the method can include recommending increasing a first ingredient and decreasing or eliminating a second ingredient. For example, the method can include recommending addition of a cosmetic ingredient, e.g., an antimicrobial, to inhibit growth of a particular type of microbe and recommending subtraction of a nutrient, e.g., a hydrocarbon source, to further inhibit growth of the particular type of microbe.

Figure 15:
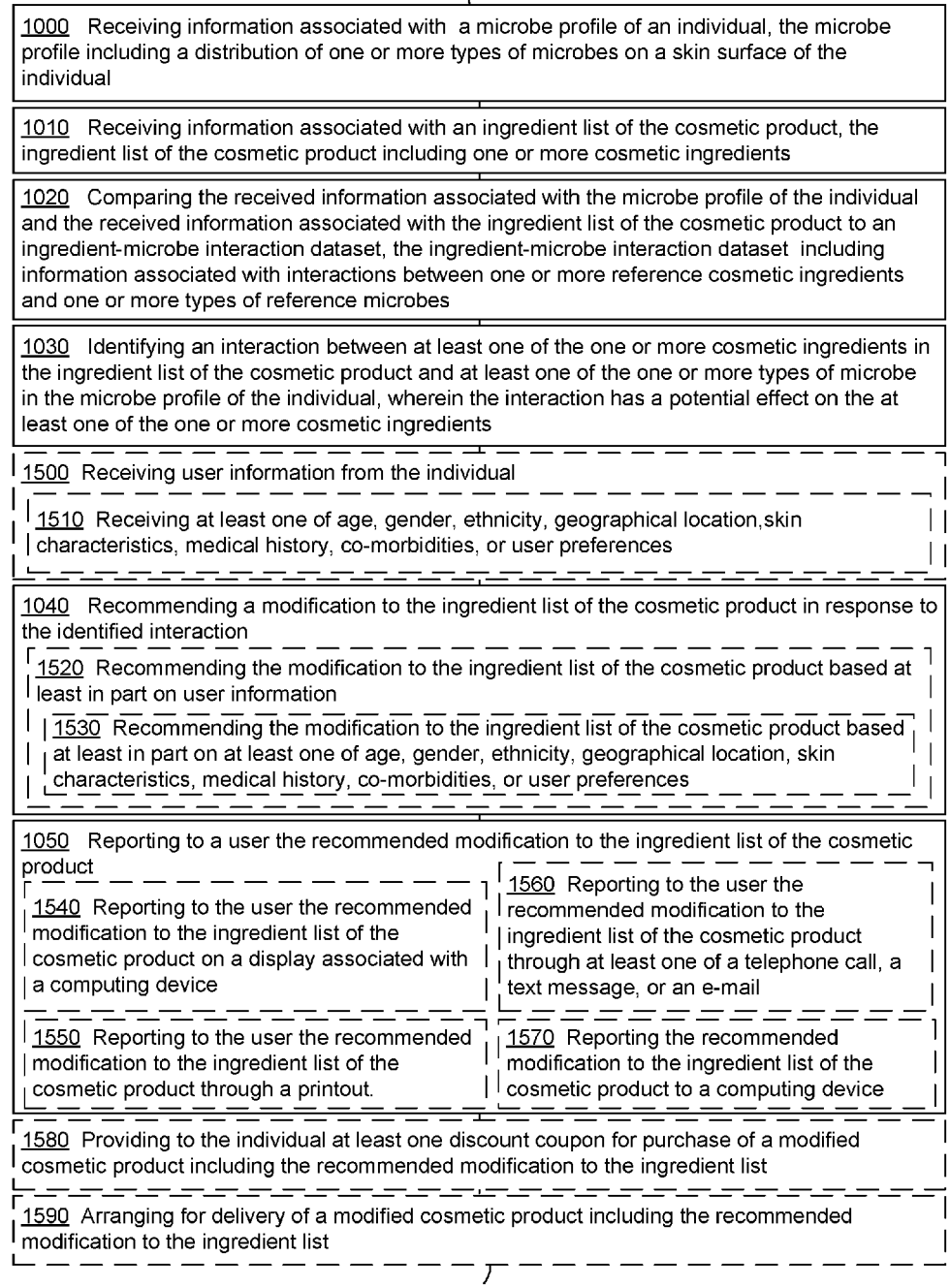
FIG. 15 depicts further aspects of a method such as shown in FIG. 10.

FIG. 15 illustrates further aspects of a method such as shown in FIG. 10. In an aspect, the method of FIG. 10 further includes receiving user information from the individual, as shown in block 1500. In an aspect, the method includes receiving the user information from the individual through a user interface, e.g., a touchscreen display, a keyboard, or a microphone. In an aspect, the method includes receiving the user information from a remote source, e.g., a personal computing device, an Internet site, or a computing component associated with a microbe profiling device, microbe profiling system, microbe profiling kit, or microbe profiling kiosk. In an aspect, the method includes receiving at least one of age, gender, ethnicity, geographical location, skin characteristics, medical history, co-morbidities, or user preferences, as shown in block 1510.

In an aspect, the method further includes recommending the modification to the ingredient list of the cosmetic product based at least in part on user information, as shown in block 1520. In an aspect, the method includes recommending the modification to the ingredient list of the cosmetic product based at least in part on at least one of age, gender, ethnicity, geographical location, skin characteristics, medical history, co-morbidities, or user preferences, as shown in block 1530. For example, the method can include recommending a modification to the ingredient list of the cosmetic product based at least in part on the age of the individual in addition to the identified interaction between a cosmetic ingredient in the ingredient list of a cosmetic product and a type of microbe in the microbe profile of the individual. For example, the method can include recommending a modification to the ingredient list of the cosmetic product based at least in part on reported skin allergies or sensitivities to specific ingredients in addition to the identified interaction.

The method of FIG. 10 further includes reporting to a user the recommended modification to the ingredient list of the cosmetic product. In an aspect, the user includes the individual for whom the microbe profile was generated. In an aspect, the user includes a second individual, e.g., a medical practitioner, a cosmetologist, or a technician. In an aspect, the user includes a computing device associated with a medical or commercial entity, e.g., a supplier or manufacturer of cosmetic goods. In an aspect, the user includes a computing device associated with a formulation device, the formulation device configured to modify the cosmetic product based on the recommended modification to the ingredient list.

In an aspect, the method includes reporting to the user the recommended modification to the ingredient list of the cosmetic product on a display associated with a computing device, as shown in block 1540. For example, the method can include reporting to the user the recommended modification to the ingredient list of the cosmetic on a display associated with a computing device on which the recommended modification is generated. In an aspect, the method includes reporting to the user the recommended modification to the ingredient list of the cosmetic product through a printout, as shown in block 1550. In an aspect, the method includes reporting to the user the recommended modification to the ingredient list of the cosmetic product through at least one of a telephone call, a text message, or an e-mail, as shown in block 1560. In an aspect, the method includes reporting the recommended modification to the ingredient list of the cosmetic product to a computing device, as shown in block 1570. For example, the method can include reporting the recommended modification to the ingredient list of the cosmetic product to a computing device operably coupled to a filling apparatus. For example, the method can include generating the recommended modification to the ingredient list of the cosmetic product based on an individual's microbe profile using a computing device at a medical practice or cosmetic counter and then reporting the recommended modification to the ingredient list of the cosmetic product to a computing device associated with a cosmetic supplier and/or manufacturer.

In an aspect, the method further includes providing to the individual at least one discount coupon for purchase of the modified cosmetic product including the recommended modification to the ingredient list, as shown in block 1580. In an aspect, the method includes providing to the individual at least one printed discount coupon. In an aspect, the method includes providing at least one discount coupon electronically to the individual's smart phone or to a computing device. In an aspect, the method includes providing the discount coupon as a discount code for use in making a purchase through the Internet or other web-based system.

In an aspect, the method further includes arranging for delivery of a modified cosmetic product including the recommended modification to the ingredient list, as shown in block 1590. For example, the method can include arranging for delivery of a modified cosmetic product by way of the Postal Service, a shipping service, e.g., FedEx or UPS, or a courier. In an aspect, the method includes automatically arranging for delivery of the modified cosmetic product. For example, a computing device executing the method described herein can automatically arrange for delivery of the modified cosmetic product. In an aspect, the method includes arranging for the delivery of the modified cosmetic product to a street address. For example, the method can include arranging for delivery of the modified cosmetic product to a street address of at least one of the individual's residence or workplace. For example, the method can include arranging for delivery of the modified cosmetic product to a street address of at least one of a medical office, beauty salon, or retail store for pick up by the individual. In an aspect, the method includes arranging for the delivery of the modified cosmetic product to a postal address, e.g., a post office box. In an aspect, the method includes arranging for delivery of the modified cosmetic product to a residence, a post office, a delivery service office, a store, a pharmacy, a medical office, or a cosmetic counter.

In an aspect, the method further includes notifying the individual that delivery of the modified cosmetic product has been arranged. In an aspect, the method includes notifying the individual by at least one of an electronic communication, a telephonic communication, or a written communication. For example, the method can include notifying the individual by way of an e-mail communication or a text message. For example, the method can include notifying the individual by way of an automated telephone call. For example, the method can include notifying the individual by way of a postcard or letter sent through the mail.

FIG. 16 illustrates aspects of a system for modifying a cosmetic product. System 1600 includes circuitry 1610. Circuitry 1610 of system 1600 includes circuitry 1620 for receiving information associated with a microbe profile of an individual, the microbe profile including a distribution of one or more types of microbes on a skin surface of the individual. Circuitry 1610 of system 1600 includes circuitry 1630 for receiving information associated with an ingredient list of the cosmetic product, the ingredient list including one or more cosmetic ingredients. Circuitry 1610 of system 1600 includes circuitry 1640 for comparing the received information associated with the microbe profile of the individual and the received information associated with the ingredient list of the cosmetic product to an ingredient-microbe interaction dataset, the one ingredient-microbe interaction dataset including information associated with interactions between one or more reference cosmetic ingredients and one or more types of reference microbes. Circuitry 1610 of system 1600 includes circuitry 1650 for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients. Circuitry 1610 of system 1600 includes circuitry 1660 for recommending a modification to the ingredient list of the cosmetic product in response to the identified interaction. Circuitry 1610 of system 1600 includes circuitry 1670 for sending a signal to report to a user the recommended modification to the ingredient list of the cosmetic product.

FIG. 17 illustrates further aspects of a system such as shown in FIG. 16. In an aspect, system 1600 includes computing device 1700. Computing device 1700 can take various forms or be part of an object, such as a personal computer, a limited resource computing device, a wireless communication device, a mobile wireless communication device, a handheld electronic writing device, a tablet, a cell phone, a PDA, or an electronic tablet device. In an aspect, computing device 1700 is associated with a manufacturing device, e.g., a device or apparatus for formulating a cosmetic product and/or filling a container with a cosmetic product. Other non-limiting aspects of a computing device have been described above herein.

Computing device 1700 includes a processor and circuitry 1610. Circuitry 1610 includes circuitry 1620 for receiving information associated with a microbe profile of an individual, the microbe profile including a distribution of one or more types of microbes on a skin surface of the individual; circuitry 1630 for receiving information associated with an ingredient list of the cosmetic product, the ingredient list including one or more cosmetic ingredients; circuitry 1640 for comparing the received information associated with the microbe profile of the individual and the received information associated with the ingredient list to an ingredient-microbe interaction dataset, the ingredient-microbe interaction dataset including information associated with interactions between one or more reference cosmetic ingredients and one or more types of reference microbes; circuitry 1650 for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; circuitry 1660 for recommending a modification to the ingredient list of the cosmetic product in response to the identified interaction; and circuitry 1670 for sending a signal to report to a user the recommended modification to the ingredient list of the cosmetic product.

In an aspect, computing device 1700 includes circuitry for executing one or more instructions for modifying a cosmetic product. In an aspect, the one or more instructions for modifying the cosmetic product include one or more instructions for receiving information associated with a microbe profile of an individual, the microbe profile including a distribution of one or more types of microbes on a skin surface of the individual; one or more instructions for receiving an ingredient list of the cosmetic product, the ingredient list including one or more cosmetic ingredients; one or more instructions for comparing the received information associated with the microbe profile of the individual and the received information associated with the ingredient list to an ingredient-microbe interaction dataset, the ingredient-microbe interaction dataset including information associated with interactions between one or more reference cosmetic ingredients and one or more types of reference microbes; one or more instructions for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; one or more instructions for recommending a modification to the ingredient list of the cosmetic product in response to the identified interaction; and one or more instructions for sending a signal to report to a user the recommended modification to the ingredient list of the cosmetic product.

System 1600 includes circuitry 1620 for receiving information associated with a microbe profile of an individual, the microbe profile including a distribution of one or more types of microbes on a skin surface of the individual. In an aspect, system 1600 includes circuitry for receiving the information associated with the microbe profile of the individual through a wireless communication, e.g., through a cellular network communication. In an aspect, system 1600 includes circuitry for receiving the information associated with the microbe profile of the individual through a wired communication, e.g., a cable, phone, or Internet connection, provided by a telephone, cable, or fiber-optic network.

FIG. 18 illustrates further aspects of a system such as shown in FIG. 16. In an aspect, system 1600 includes circuitry 1800 for receiving the information associated with the microbe profile of the individual from a microbe profiling device, e.g., a hand-held microbe profiling device with a transmission unit for wireless communication. In an aspect, system 1600 includes circuitry 1810 for receiving the information associated with the microbe profile of the individual from a microbe profiling system, e.g., a kiosk microbe profiling system with a cable connection to the Internet. In an aspect, system 1600 includes circuitry 1820 for receiving the information associated with the microbe profile of the individual from a computing component associated with at least one of a microbe profiling device or a microbe profiling system. In an aspect, system 1600 includes circuitry 1830 for receiving the information associated with the microbe profile of the individual from a portable data storage device, e.g., a compact disk or a memory card or stick. In an aspect, system 1600 includes circuitry 1840 for receiving the information associated with the microbe profile of the individual from at least one of a remote computing device, a remote server, or the Internet.

System 1600 includes circuitry 1630 for receiving information associated with an ingredient list of the cosmetic product. In an aspect, system 1600 includes circuitry for receiving the information associated with the ingredient list of the cosmetic product through a wireless communication, e.g., through a cellular network communication. In an aspect, system 1600 includes circuitry for receiving the information associated with the ingredient list of the cosmetic product through a wired communication, e.g., a cable, phone, or Internet connection, provided by a telephone, cable, or fiber-optic network.

FIG. 19 illustrates further aspects of the system of FIG. 16. In an aspect, system 1600 includes circuitry 1900 for receiving information associated with the one or more cosmetic ingredients in the ingredient list of the cosmetic product. In an aspect, system 1600 includes circuitry 1910 for receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emollient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax in the ingredient list of the cosmetic product. In an aspect, system 1600 includes circuitry 1920 for receiving information associated with at least one of one or more probiotic agents, one or more prebiotics agents, or one or more therapeutic agents in the ingredient list of the cosmetic product. In an aspect, system 1600 includes circuitry 1930 for receiving the information associated with the ingredient list of the cosmetic product from a remote source. In an aspect, system 1600 includes circuitry 1940 for receiving the information associated with the ingredient list of the cosmetic product from a cosmetic distributer, a cosmetic manufacturer, or a cosmetic formulary. In an aspect, system 1600 includes circuitry 1950 for receiving the information associated with the ingredient list of the cosmetic product from a portable data storage device. In an aspect, system 1600 includes circuitry 1960 for receiving the information associated with the ingredient list of the cosmetic product from a scanning device.

System 1600 includes circuitry 1640 for comparing the received information associated with the microbe profile of the individual and the received information associated with the ingredient list of the cosmetic product to the ingredient-microbe interaction dataset, the ingredient-microbe interaction dataset including information associated with interactions between one or more reference cosmetic ingredients and one or more types of reference microbes. In an aspect, the ingredient-microbe interaction dataset is stored in a memory component of a computing device of the system. In an aspect, the ingredient-microbe interaction dataset is accessed from a remote computing device or remote server through a web or Internet connection. In an aspect, the ingredient-microbe interaction dataset is stored on a portable data storage device, e.g., a CD ROM or a memory card or stick.

FIG. 20 illustrates further aspects of system 1600. In an aspect, system 1600 includes circuitry 2000 for comparing the one or more types of microbes in the microbe profile of the individual to the one or more types of reference microbes in the ingredient-microbe interaction dataset. For example, the system includes circuitry for comparing an identified type of microbe, e.g., *Staphylococcus epidermidis*, to the one or more types of reference microbes to determine any interactions of the identified type of microbe with the one or more reference cosmetic ingredients. In an aspect, system 1600 includes circuitry 2010 for comparing the one or more cosmetic ingredients in the ingredient list of the cosmetic product to the one or more reference cosmetic ingredients in the ingredient-microbe interaction dataset. For example, the system includes circuitry for comparing a cosmetic ingredient, e.g., stearic acid, in the ingredient list of the cosmetic product to the one or more reference cosmetic ingredients to determine any interactions of the cosmetic ingredient with the one or more types of reference microbes.

System 1600 further includes circuitry 1650 for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients. For example, the system can include circuitry for identifying an interaction between a cosmetic ingredient in a cosmetic product and a type of microbe in the microbe profile of the individual from the comparison of the microbe profile and the ingredient list of the cosmetic product to the ingredient-microbe interaction dataset, the interaction having a potential effect on one or more properties of the cosmetic ingredient. In an aspect, system 1600 includes circuitry 2020 for identifying the potential effect on the at least one of the one or more cosmetic ingredients in the ingredient list of the cosmetic product in response to at least one of the one or more types of microbes in the microbe profile of the individual. In an aspect, system 1600 includes circuitry 2030 for identifying a potential color effect on the at least one of the one or more cosmetic ingredients in the ingredient list of the cosmetic product. For example, the system can include circuitry for identifying a potential color effect caused by the interaction between a chromogenic substrate in the cosmetic product and a type of microbe in the microbe profile of the individual. For example, the system can include circuitry for identifying a potential color effect caused by the interaction between a pH sensitive pigment or dye in the cosmetic product and a type of microbe in the microbe profile of the individual.

In an aspect, system 1600 includes circuitry 2040 for identifying a potential texture effect on the at least one of the one or more cosmetic ingredients in the ingredient list of the cosmetic product. For example, the system can include circuitry for identifying one or more cosmetic ingredients, e.g., emulsifiers or emollients, in the cosmetic product that are metabolized or assimilated by the one or more types of microbes in the microbe profile and result in a change in texture, e.g., "silkiness" or "smoothness" of the cosmetic product.

In an aspect, system 1600 includes circuitry 2050 for identifying a potential pH effect on the at least one of the one or more cosmetic ingredients in the ingredient list of the cosmetic product. For example, the system can include circuitry for identifying a potential pH effect between a cosmetic ingredient and a particular type of bacteria, e.g., lactic acid producing species of *Lactobacilli*, in the microbe profile of the individual.

In an aspect, system 1600 includes circuitry 2050 for identifying a potential odor effect on the at least one of the one or more cosmetic ingredients in the ingredient list of the cosmetic product. For example, the system can include circuitry for identifying a potential odor effect caused by metabolism or degradation of one or more of the cosmetic ingredients in the presence of one or more types of microbes in the microbe profile of the individual.

FIG. 21 illustrates further aspects of system 1600. System 1600 includes circuitry 1660 for recommending a modification to the ingredient list of the cosmetic product in response to the identified interaction. In an aspect, system 1600 includes circuitry 2100 for recommending a modification to the ingredient list of the cosmetic product to alleviate the identified interaction. In an aspect, the system includes circuitry for recommending a modification to the ingredient list of the cosmetic product to lessen the identified interaction. In an aspect, the system includes circuitry for recommending a modification to the ingredient list of the cosmetic product to eliminate the identified interaction. In an aspect, the system includes circuitry for recommending a modification to the ingredient list of the cosmetic product to alleviate the potential effect on the at least one of the one or more cosmetic ingredients in response to the at least one of the one or more types of microbes in the microbe profile of the individual. In an aspect, the system includes circuitry for recommending a modification to the ingredient list of the cosmetic product to alleviate at least one of a potential color effect, a potential texture effect, a potential pH effect, or a potential odor effect on the at least one of the one or more cosmetic ingredients in response to the at least one of the one or more types of microbes in the microbe profile of the individual.

In an aspect, system 1600 includes circuitry 2110 for recommending a modification to the ingredient list of the cosmetic product to enhance the identified interaction. In an aspect, the system includes circuitry for recommending a modification to the ingredient list of the cosmetic product to enhance the potential effect on the at least one of the one or more cosmetic ingredients in response to the at least one of the one or more types of microbes in the microbe profile of the individual. In an aspect, the system includes circuitry for recommending a modification to the ingredient list of the cosmetic product to enhance at least one of a potential color effect, a potential texture effect, a potential pH effect, or a potential odor effect on the at least one of the one or more cosmetic ingredients in response to the at least one of the one or more types of microbes in the microbe profile of the individual.

In an aspect, system 1600 includes circuitry 2120 for recommending an addition of at least one cosmetic ingredient to the ingredient list of the cosmetic product in response to the identified interaction. In an aspect, the system includes circuitry for recommending an addition of at least one cosmetic ingredient to the ingredient list of the cosmetic product to alleviate or enhance the potential effect on the at least one of the one or more cosmetic ingredients in response to the at least one of the one or more types of microbes in the microbe profile of the individual. In an aspect, the system includes circuitry for recommending an addition of at least one cosmetic ingredient to the ingredient list of the cosmetic product to alleviate or enhance at least one of a potential color effect, a potential texture effect, a potential pH effect, or a potential odor effect on the at least one of the one or more cosmetic ingredients in response to the at least one of the one or more types of microbes in the microbe profile of the individual.

In an aspect, system 1600 includes circuitry 2130 for recommending a subtraction of at least one cosmetic ingredient from the ingredient list of the cosmetic product. In an aspect, the system includes circuitry for recommending a subtraction of at least one cosmetic ingredient from the ingredient list of the cosmetic product to alleviate or enhance the potential effect on the at least one of the one or more cosmetic ingredients in response to the at least one of the one or more types of microbes in the microbe profile of the individual. In an aspect, the system includes circuitry for recommending a subtraction of at least one cosmetic ingredient from the ingredient list of the cosmetic product to alleviate or enhance at least one of a potential color effect, a potential texture effect, a potential pH effect, or a potential odor effect on the at least one of the one or more cosmetic ingredients in response to the at least one of the one or more types of microbes in the microbe profile of the individual.

In an aspect, system 1600 includes circuitry 2140 for recommending a relative change in concentration of at least one cosmetic ingredient in the ingredient list of the cosmetic product. In an aspect, the system includes circuitry for recommending a relative change in concentration of at least one cosmetic ingredient to the ingredient list of the cosmetic product to alleviate or enhance the potential effect on the at least one of the one or more cosmetic ingredients in response to the at least one of the one or more types of microbes in the microbe profile of the individual. In an aspect, the system includes circuitry for recommending a relative change in concentration of at least one cosmetic ingredient to the ingredient list of the cosmetic product to alleviate or enhance at least one of a potential color effect, a potential texture effect, a potential pH effect, or a potential odor effect on the at least one of the one or more cosmetic ingredients in response to the at least one of the one or more types of microbes in the microbe profile of the individual.

FIG. 22 illustrates further aspects of system 1600. In an aspect, system 1600 includes circuitry 2200 for receiving user information from the individual. In an aspect, the system includes circuitry for receiving the user information from the individual through a user interface, e.g., a touchscreen display, a keyboard, or a microphone. In an aspect, the system includes circuitry for receiving the user information from a remote source, e.g., a personal computing device, an Internet site, or a computing component associated with a microbe profiling device, microbe profiling system, microbe profiling kit, or microbe profiling kiosk. In an aspect, system 1600 includes circuitry 2210 for receiving at least one of age, gender, ethnicity, geographical location, skin characteristics, medical history, co-morbidities, or user preferences.

In an aspect, system 1600 includes circuitry 2220 for recommending the modification to the ingredient list of the cosmetic product based at least in part on user information. In an aspect, system 1600 includes circuitry 2230 for recommending the modification to the ingredient list of the cosmetic product based at least in part on at least one of age, gender, ethnicity, geographical location, skin characteristics, medical history, co-morbidities, or user preferences.

System 1600 includes circuitry 1670 for sending a signal to report to a user the recommended modification to the ingredient list of the cosmetic product. In an aspect, system 1600 includes circuitry 2240 for sending a signal to report to the user the recommended modification to the ingredient list of the cosmetic product on a display associated with a computing device. In an aspect, system 1600 includes circuitry 2250 for sending a signal to report to the user the recommended modification to the ingredient list of the cosmetic product through a printout. In an aspect, system 1600 includes circuitry 2260 for sending a signal to report to the user the recommended modification to the ingredient list of the cosmetic product through at least one of a telephone call, a text message, or an e-mail. In an aspect, system 1600 includes circuitry 2270 for sending a signal to report the recommended modification to the ingredient list of the cosmetic product to a computing device.

In an aspect, system 1600 further includes circuitry 2280 for providing to the individual at least one discount coupon for purchase of the modified cosmetic product including the recommended modification to the ingredient list. In an aspect, the system includes circuitry for providing to the individual at least one printed discount coupon. In an aspect, the system includes circuitry for providing at least one discount coupon electronically to the individual's smart phone or to a computing device. In an aspect, the system includes circuitry for providing the discount coupon as a discount code for use in making a purchase through the Internet or other web-based system.

In an aspect, system 1600 further includes circuitry 2290 for arranging for delivery of a modified cosmetic product including the recommended modification to the ingredient list. For example, the system can include circuitry for arranging for delivery of a modified cosmetic product by way of the Postal Service, a shipping service, e.g., FedEx or UPS, or a courier. In an aspect, the system includes circuitry for automatically arranging for delivery of the modified cosmetic product. In an aspect, the system includes circuitry for arranging for the delivery of the modified cosmetic product to a street address, e.g., a street address of the individual's residence or workplace, or of a medical office, beauty salon, or retail store for pick up by the individual. In an aspect, the system includes circuitry for arranging for the delivery of the modified cosmetic product to a postal address, e.g., a post office box. In an aspect, the system includes circuitry for arranging for the delivery of the modified cosmetic product to a residence, a post office, a delivery service office, a store, a pharmacy, a medical office, or a cosmetic counter.

In an aspect, the system includes circuitry for notifying the individual by at least one of an electronic communication, a telephonic communication, or a written communication that delivery of the modified cosmetic product has been arranged.

Figure 23:
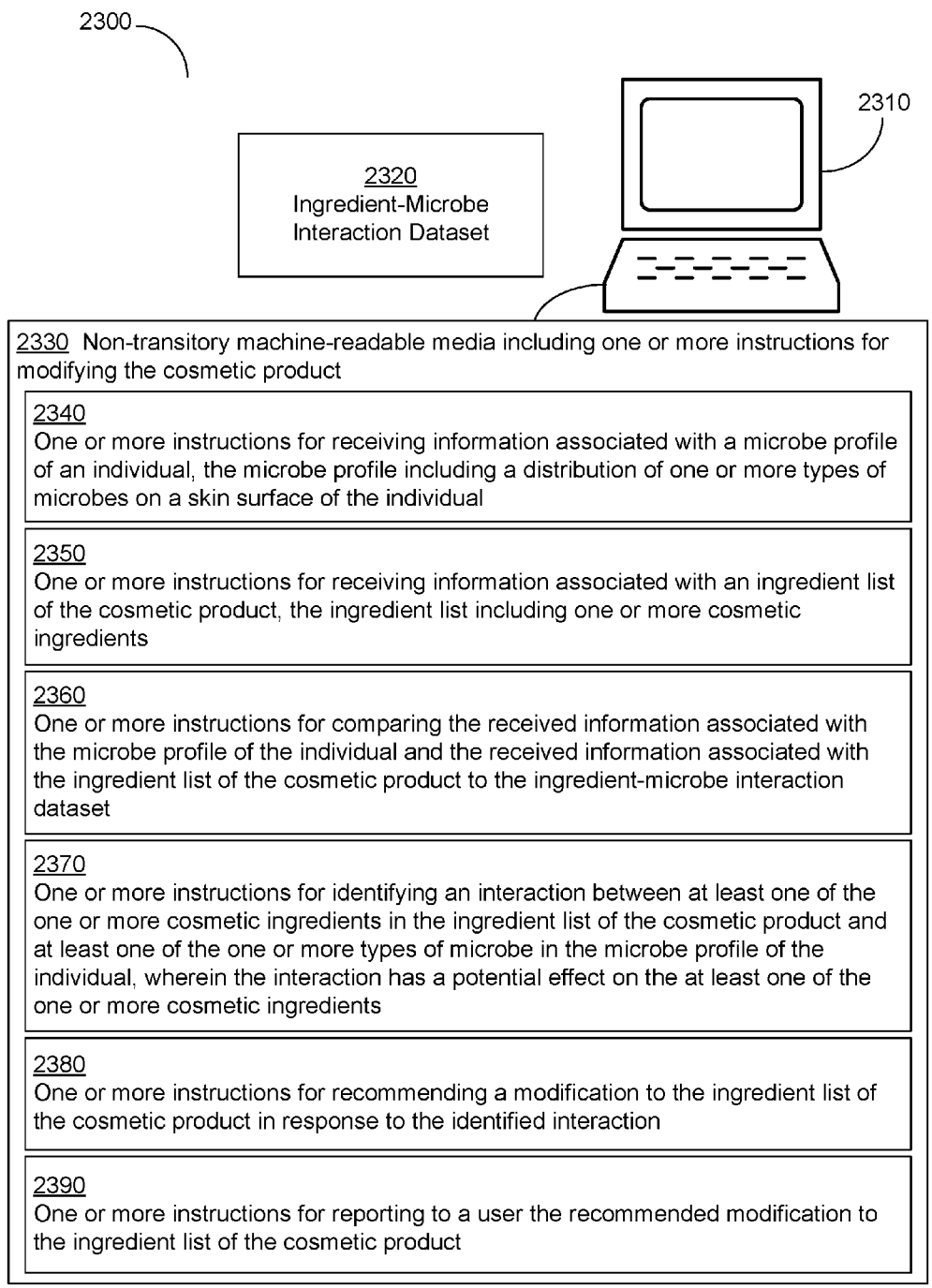
FIG. 23 illustrates a system for modifying a cosmetic product based on a microbe profile.

FIG. 23 illustrates aspects of a system for modifying a cosmetic product based on a microbe profile. System 2300 includes computing device 2310; ingredient-microbe interaction dataset 2320 including information associated with interactions between one or more reference cosmetic ingredients and one or more types of reference microbes; and non-transitory machine-readable media 2330 including one or more instructions for modifying a cosmetic product. Non-transitory machine readable media 2330 includes one or more instructions 2340 for receiving information associated with a microbe profile of an individual, the microbe profile including a distribution of one or more types of microbes on a skin surface of the individual; one or more instruction 2350 for receiving information associated with an ingredient list of the cosmetic product, the ingredient list including one or more cosmetic ingredients; one or more instructions 2360 for comparing the received information associated with the microbe profile of the individual and the received information associated with the ingredient list of the cosmetic product to the ingredient-microbe interaction dataset 2320; one or more instructions 2370 for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients; one or more instruction 2380 for recommending a modification to the ingredient list of the cosmetic product in response to the identified interaction; and one or more instructions 2390 for reporting to a user the recommended modification to the ingredient list of the cosmetic product.

System 2300 includes computing device 2310. Computing device includes a processor and is capable of executing one or more instructions. Computing device 2310 can take various forms or be part of an object, such as a personal computer, a limited resource computing device, a wireless communication device, a mobile wireless communication device, a handheld electronic writing device, a tablet, a cell phone, a PDA, or an electronic tablet device. In an aspect, computing device 2310 is associated with a microbe profiling device or a microbe profiling system. In an aspect, computing device 2310 is a computing component associated with a microbe profiling device or a microbe profiling system. In an aspect, computing device 2310 is associated with a manufacturing device, e.g., a device or apparatus for formulating a cosmetic product and/or filling a container with a cosmetic product. Other non-limiting aspects of a computing device have been described herein.

System 2300 includes ingredient-microbe interaction dataset 2320. Ingredient-microbe interaction dataset 2320 includes information associated with interactions between one or more reference cosmetic ingredients and one or more types of reference microbes. In an aspect, ingredient-microbe interaction dataset 2320 includes one or more reference cosmetic ingredients, non-limiting examples of which have been described above herein. In an aspect, ingredient-microbe interaction dataset 2320 includes one or more types of reference microbes, non-limiting examples of which have been described above herein. In an aspect, ingredient-microbe interaction dataset 2320 includes information associated with interactions between the one or more reference cosmetic ingredients and the one or more types of reference microbes. In an aspect, ingredient-microbe interaction dataset 2320 includes information associated with a potential effect on the one or more reference cosmetic ingredients in response to the one or more types of reference microbes. In an aspect, ingredient-microbe interaction dataset 2320 includes information associated with at least one of a potential color effect, a potential texture effect, a potential pH effect, or a potential odor effect on the one or more reference cosmetic ingredients in response to the one or more types of reference microbes.

In an aspect, ingredient-microbe interaction dataset 2320 is incorporated into a memory component of computing device 2310. In an aspect, ingredient-microbe interaction dataset 2320 is stored on a portable data storage device. In an aspect, ingredient-microbe interaction dataset 2320 is stored on a remote computing device. In an aspect, the remote computing device is associated with a cosmetic supplier, a cosmetic manufacturer, or a cosmetic formulary. In an aspect, ingredient-microbe interaction dataset 2320 is updatable. Additional non-limiting aspects of an ingredient-microbe interaction dataset have been described above herein.

System 2300 further includes non-transitory machine-readable media 2330 including one or more instructions for modifying the cosmetic product. The non-transitory machine-readable media 2330 includes one or more instructions 2340 for receiving information associated with a microbe profile of an individual. In an aspect, the one or more instructions include one of more instructions for receiving the information associated with the microbe profile of the individual through a wired and/or wireless communication link. In an aspect, the one or more instructions include one or more instructions for receiving the information associated with the microbe profile of the individual from a microbe profiling device or a microbe profiling system. In an aspect, the one or more instructions include one or more instructions for receiving the information associated with the microbe profile of the individual from a computing component associated with a microbe profiling device or a microbe profiling system. In an aspect, the one or more instructions include one or more instructions for receiving the information associated with the microbe profile of the individual from a portable data storage device. In an aspect, the one or more instructions include one or more instructions for receiving the information associated with the microbe profile of the individual from the Internet.

The non-transitory machine-readable media 2330 of system 2300 includes one or more instructions 2350 for receiving information associated with an ingredient list of the cosmetic product. In an aspect, the one or more instructions include one or more instructions for receiving information associated with one or more cosmetic ingredients in the ingredient list of the cosmetic product. In an aspect, the one or more instructions include one or more instructions for receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emollient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax in the ingredient list of the cosmetic product. In an aspect, the one or more instructions include one or more instructions for receiving information associated with at least one of one or more probiotic agents, one or more prebiotic agents, or one or more therapeutic agents. In an aspect, the one or more instructions include one or more instructions for receiving the information associated with the ingredient list of the cosmetic product from at least one of a portable data storage device, the Internet, or a remote source.

In an aspect, system 2300 further includes a scanning device operably coupled to the computing device. Non-limiting examples of scanning devices configured to scan the ingredient label of the cosmetic product have been described above herein. System 2300 further includes one or more instructions for scanning and digitizing the ingredient label of the cosmetic product, the ingredient label including the ingredient list of the cosmetic product.

Non-transitory machine-readable media 2330 of system 2300 includes one or more instructions 2360 for comparing the received information associated with the microbe profile of the individual and the received information associated with the ingredient list of the cosmetic product to the ingredient-microbe interaction dataset. In an aspect, the one or more instructions include one or more instructions for comparing the one or more types of microbes in the microbe profile of the individual with the one or more types of reference microbes in the ingredient-microbe interaction dataset. In an aspect, the one or more instructions include one or more instructions for comparing the one or more cosmetic ingredients in the ingredient list of the cosmetic product with the one or more reference cosmetic ingredients in the ingredient-microbe interaction dataset.

Non-transitory machine-readable media 2330 of system 2300 includes one or more instructions 2370 for identifying an interaction between at least one of the one or more cosmetic ingredients in the ingredient list of the cosmetic product and at least one of the one or more types of microbes in the microbe profile of the individual. In an aspect, the one or more instructions include one or more instructions for identifying the potential effect on the at least one of the one or more cosmetic ingredients in the ingredient list of the cosmetic product in response to at least one of the one or more types of microbes in the microbe profile of the individual. In an aspect, the one or more instructions include one or more instructions for identifying at least one of a potential color effect, a potential texture effect, a potential pH effect, or a potential odor effect on the at least one of the one or more cosmetic ingredients in the ingredient list of the cosmetic product in response to at least one of the one or more types of microbes in the microbe profile of the individual.

Non-transitory machine-readable media 2330 of system 2300 includes one or more instructions 2380 for recommending a modification to the ingredient list of the cosmetic product in response to the identified interaction. In an aspect, the one or more instructions include one or more instructions for recommending a modification to the ingredient list of the cosmetic product to alleviate the identified interaction. In an aspect, the one or more instructions include one or more instructions for recommending a modification to the ingredient list of the cosmetic product to enhance the identified interaction. In an aspect, the one or more instructions include one or more instructions for recommending an addition of at least one cosmetic ingredient to the ingredient list of the cosmetic product. In an aspect, the one or more instructions include one or more instructions for recommending a subtraction of at least one cosmetic ingredient from the ingredient list of the cosmetic product. In an aspect, the one or more instructions include one or more instructions for recommending a relative change in concentration of at least one cosmetic ingredient in the ingredient list of the cosmetic product.

In an aspect, system 2300 further includes a user interface operably coupled to computing device 2310. For example, system 2300 can include a monitor and keyboard operably coupled to computing device 2310. Other non-limiting examples of user interfaces have been describe above herein.

In an aspect, non-transitory machine readable media 2330 of system 2300 includes one or more instructions for receiving user information from the individual. In an aspect, the one or more instructions include one or more instructions for receiving the user information from the individual through a user interface operably coupled to computing device 2310. In an aspect, the one or more instructions for receiving user information from the individual include one or more instructions for receiving at least one of age, gender, ethnicity, geographical location, skin characteristics, medical history, co-morbidities, or user preferences from the individual. In an aspect, the one or more instructions include one or more instructions for recommending the modification to the ingredient list of the cosmetic product based at least in part on user information. In an aspect, the one or more instructions include one or more instructions for recommending the modification to the ingredient list of the cosmetic product based at least in part on at least one of age, gender, ethnicity, geographical location, skin characteristics, medical history, co-morbidities, or user preference.

Non-transitory machine-readable media 2330 of system 2300 includes one or more instructions 2390 for reporting to a user the recommended modification to the ingredient list of the cosmetic product. In an aspect, the one or more instructions include one or more instructions for reporting to the user the recommended modification to the ingredient list of the cosmetic product on a display associated with computing device 2310. In an aspect, the one or more instructions include one or more instructions for reporting to the user the recommended modification to the ingredient list of the cosmetic product through a printout. In an aspect, the one or more instructions include one or more instructions for reporting to the user the recommended modification to the ingredient list of the cosmetic product through at least one of a telephone call, a text message, or an e-mail. In an aspect, the one or more instructions include one or more instructions for reporting the recommended modification to the ingredient list of the cosmetic product to a remote computing device.

Non-transitory machine-readable media 2030 of system 2300 includes one or more instructions for providing to the individual at least one discount coupon for purchase of a modified cosmetic product including the recommended modification to the ingredient list. Non-transitory machine-readable media 2330 of system 2300 includes one or more instructions for arranging for delivery of a modified cosmetic product including the recommended modification to the ingredient list. Non-transitory machine-readable media 2330 of system 2300 includes one or more instructions for notifying the individual of the arranged delivery of the modified cosmetic ingredient.

Figure 24:
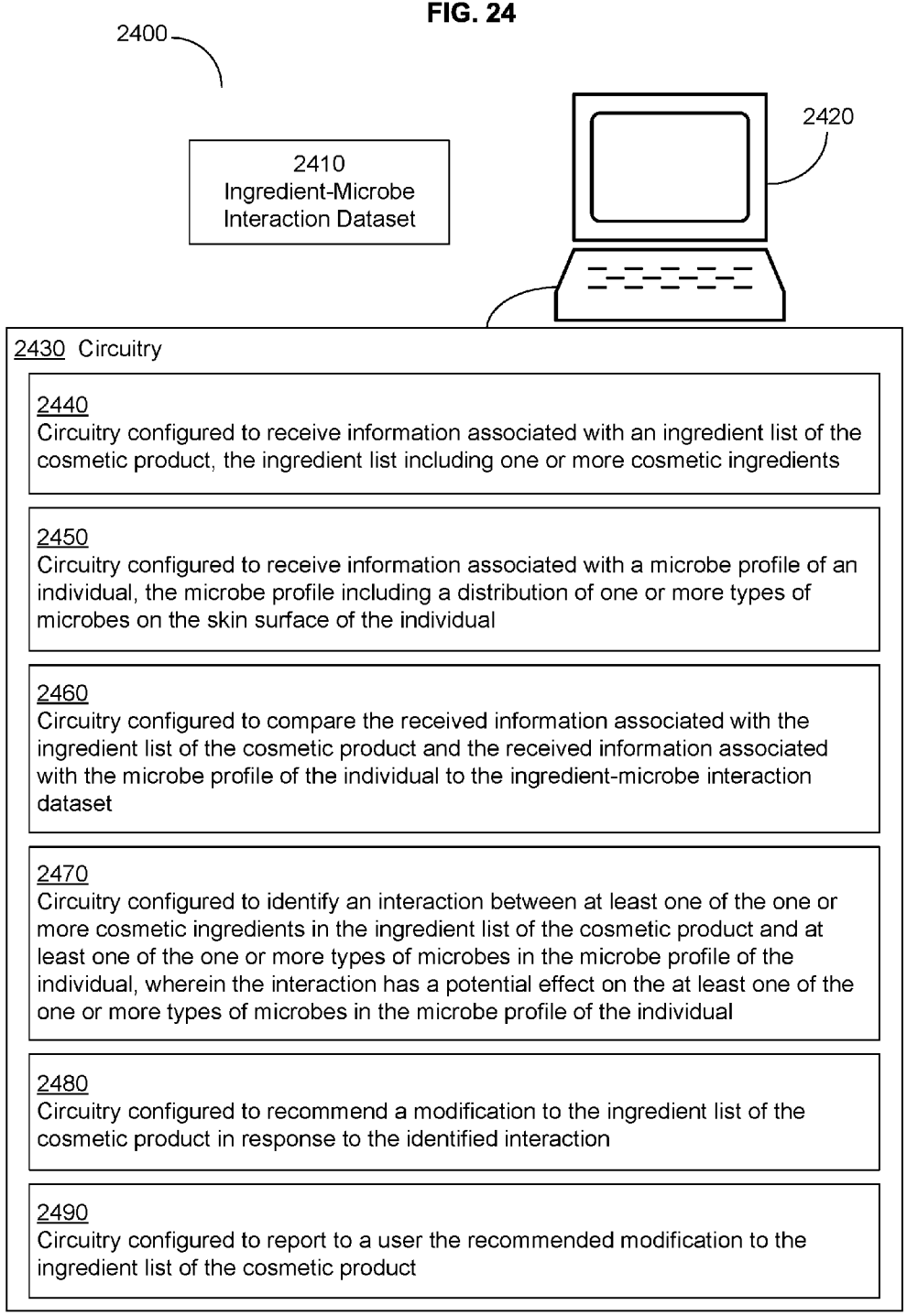
FIG. 24 illustrates a system for modifying a cosmetic product based on a microbe profile.

With reference to FIG. 24, shown is a system for modifying a cosmetic product. System 2400 includes an ingredient-microbe interaction dataset 2410 including information associated with interactions between one or more reference cosmetic ingredients and one or more types of reference microbes; and a computing device 2420. Computing device 2420 includes a processor and circuitry 2430. Circuitry 2430 includes circuitry 2440 configured to receive information associated with an ingredient list of the cosmetic product, the ingredient list including one or more cosmetic ingredients; circuitry 2450 configured to receive information associated with a microbe profile of an individual, the microbe profile including a distribution of one or more types of microbes on a skin surface of the individual; circuitry 2460 configured to compare the received information associated with the ingredient list of the cosmetic product and the received information associated with the microbe profile of the individual to the ingredient-microbe interaction dataset; circuitry 2470 configured to identify an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual; circuitry 2480 configured to recommend a modification to the ingredient list of the cosmetic product in response to the identified interaction; and circuitry 2490 configured to report to a user the recommended modification to the ingredient list of the cosmetic product.

FIG. 25 illustrates further aspects of system 2400. System 2400 includes ingredient-microbe interaction dataset 2410. Ingredient-microbe interaction dataset 2410 includes one or more reference cosmetic ingredients 2500. In an aspect, the one or more reference cosmetic ingredients 2500 include one or more of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax, as shown in block 2505. In an aspect, the one or more reference cosmetic ingredients 2500 include at least one of one or more probiotic agents, one or more prebiotic agents, or one or more therapeutic agents, as shown in block 2510. In an aspect, the one or more reference cosmetic ingredients includes one or more agents with properties to directly modulate a microbe profile by interacting with one or more types of microbes in the microbe profile to modulate proliferation and/or growth. In an aspect, the one or more reference cosmetic ingredients include one or more agents with properties to indirectly modulate a microbe profile by modifying the microbial environment.

Ingredient-microbe interaction dataset 2410 further includes one or more types of reference microbes 2515. In an aspect, the one or more types of reference microbes 2515 include one or more types of skin-associated microbes 2520. Non-limiting examples of skin-associated, skin-resident, non-pathogenic, and/or pathogenic microbes have been described above herein.

Ingredient-microbe interaction dataset 2410 includes information 2525 associated with the interactions between the one or more reference cosmetic ingredients and the one or more types of reference microbes. In an aspect, ingredient-microbe interaction dataset 2410 includes information 2530 associated with a potential effect on the one or more types of reference microbes in response to the one or more reference cosmetic ingredients. In an aspect, ingredient-microbe interaction dataset 2410 includes information 2535 associated with a potential growth promoting effect on the one or more types of reference microbes in response to the one or more reference cosmetic ingredients. For example, the ingredient-microbe interaction dataset can include information associated with cosmetic ingredients that promote the growth of one or more types of microbes. For example, cosmetic ingredients that raise the pH of a cosmetic product may promote the growth of undesirable microbes and loss of normal microbes. See, e.g., Grise et al. (2011) Nat Rev Microbiol 9:244-253, which is incorporated herein by reference.

In an aspect, ingredient-microbe interaction dataset 2410 includes information 2540 associated with a potential growth inhibiting effect on the one or more types of reference microbes in response to the one or more reference cosmetic ingredients. For example, the ingredient-microbe interaction dataset may include information associated with cosmetic ingredients that inhibit the growth of one or more types of microbes. For example, cosmetic ingredients that raise the pH of a cosmetic product may inhibit the growth of commensal microbes. For example, certain preservatives commonly used in cosmetic products, e.g., triclosan and parabens, may inhibit the growth of commensal microbes on the skin surface and contribute to allergic responses. See, e.g., Savage et al. (2012) J. Allergy Clin. Immunol. 130:453-460, which is incorporated herein by reference. In an aspect, the ingredient-microbe interaction dataset includes information associated with a potential stasis effect on the one or more types of reference microbes in response to the one or more reference cosmetic ingredients. For example, the ingredient-microbe interaction dataset can include one or more cosmetic ingredients that promote stasis or maintenance of one or more types of microbes. In an aspect, ingredient-microbe interaction dataset includes information associated with a potential cytotoxic effect on the one or more types of reference microbes in response to the one or more reference cosmetic ingredients. For example, the ingredient-microbe interaction dataset can include information associated with cosmetic ingredients that kill one or more types of microbes.

In an aspect, ingredient-microbe interaction dataset 2410 includes information 2545 associated with a potential biofilm formation effect on the one or more types of reference microbes in response to the one or more reference cosmetic ingredients. For example, the ingredient-microbe interaction dataset can include information associated with cosmetic ingredients that promote biofilm formation of one or more types of microbes. For example, certain metals, e.g., iron, have been shown to promote bacterial biofilm formation, e.g., biofilm formation of *Pseudomonas aeruginosa*. See, e.g., Banin et al. (2005) Proc. Natl. Acad. Sci., USA 102: 11076-11081, which is incorporated herein by reference.

In an aspect, ingredient-microbe interaction dataset 2410 is incorporated into a memory component of computing device 2420, as shown in block 2550. In an aspect, ingredient-microbe interaction dataset 2410 is stored on a portable data storage device, as shown in block 2555. In an aspect, ingredient-microbe interaction dataset 2410 is stored one a remote computing device, as shown in block 2560. In an aspect, ingredient-microbe interaction dataset 2410 is updatable, as shown in block 2565.

Figure 26:
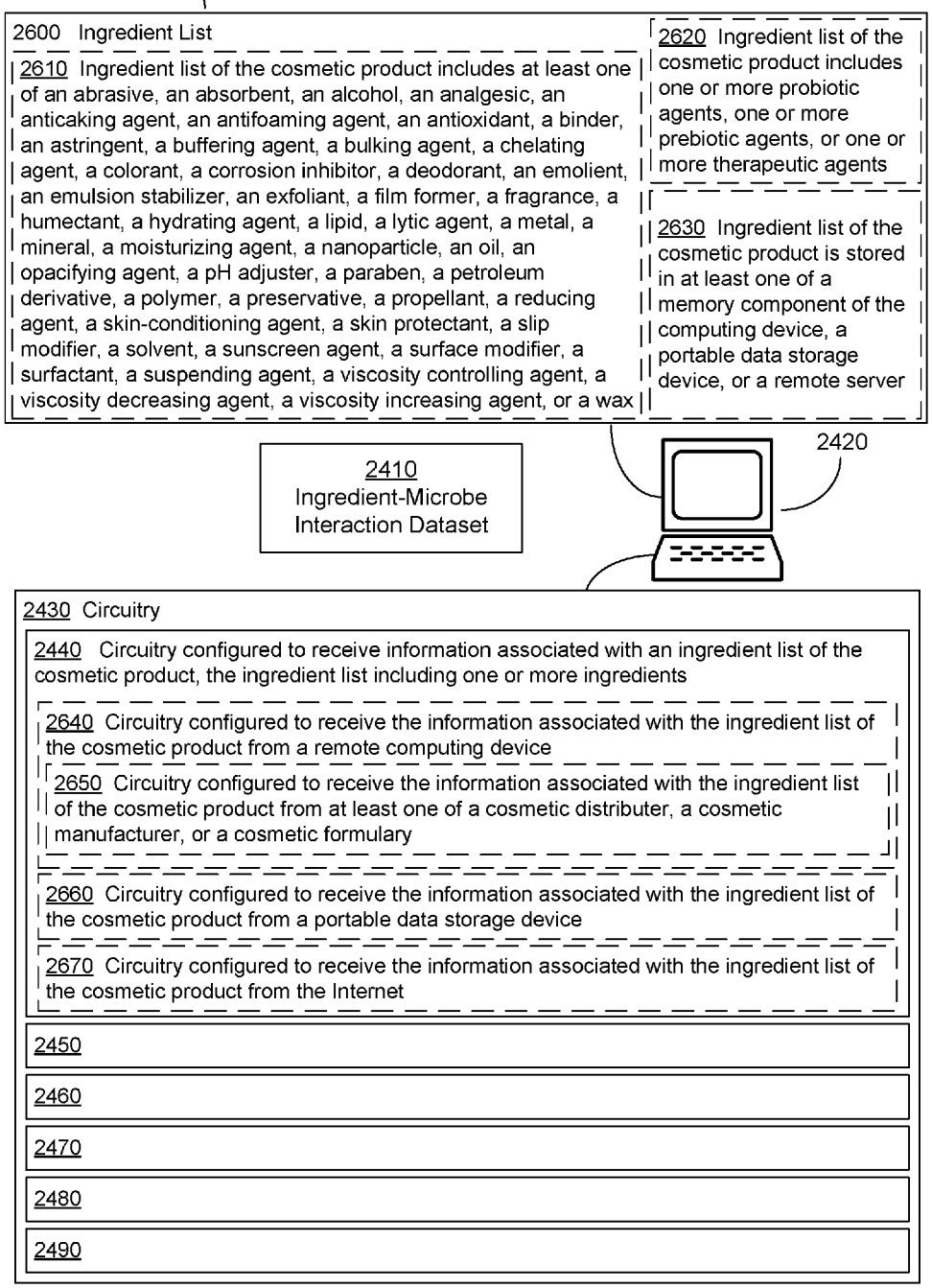
FIG. 26 shows further aspects of a system such as depicted in FIG. 24.

FIG. 26 shows further aspects of system 2400. System 2400 includes circuitry 2440 configured to receive information associated with an ingredient list 2600 of the cosmetic product, the ingredient list including one or more cosmetic ingredients. For example, the ingredient list can include the list of cosmetic ingredients printed on the label of a cosmetic product. For example, the ingredient list can include a dataset of cosmetic ingredients commonly used in cosmetic products. For example, the ingredient list can include a dataset that includes any of a number of GRAS (Generally Regarded As Safe) ingredients as outlined under sections 201(s) and 409 of the Federal Food, Drug, and Cosmetic Act.

In an aspect, the one or more cosmetic ingredients in the ingredient list of the cosmetic product include at least one of the one or more reference cosmetic ingredients in the ingredient-microbe interaction dataset. In an aspect, the ingredient list 2600 of the cosmetic product includes at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emollient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax, as shown in block 2610. In an aspect, the one or more cosmetic ingredients in the ingredient list of the cosmetic product include at least one of one or more probiotic agents, one or more prebiotic agents, or one or more therapeutic agents, as shown in block 2620. Non-limiting examples of cosmetic ingredients have been described above herein.

In an aspect, the ingredient list of the cosmetic product is stored in at least one of a memory component of computing device 2420, a portable data storage device, or a remoter server, as shown in block 2630. In an aspect, circuitry 2440 includes circuitry 2640 configured to receive the information associated with the ingredient list of the cosmetic product from a remote computing device. For example, the system can include circuitry configured to receive the information associated with the ingredient list of the cosmetic product from a personal computing device, e.g., the individual's smart phone. In an aspect, circuitry 2440 includes circuitry 2650 configured to receive the information associated with the ingredient list of the cosmetic product from at least one of a cosmetic distributer, a cosmetic manufacturer, or a cosmetic formulary. For example, the system can include circuitry configured to receive the information associated with the ingredient list of the cosmetic product from a cosmetic manufacturer manufacturing the cosmetic product at issue. In an aspect, the remote computing device includes a remote server accessible to computing device 2420. For example, the ingredient list may be stored on a remote computing device associated with a cosmetic supplier and accessible to computing device 2420 through a web-based, e.g., Internet, connection. In an aspect, the ingredient list is stored on a cloud-based server. In an aspect, the remote computing device includes a personal computing device, e.g., a home computer, a tablet, or smart phone. In an aspect, the ingredient list of the cosmetic product is stored on a portable data storage device. In an aspect, circuitry 2440 includes circuitry 2660 configured to receive the information associated with the ingredient list of the cosmetic product from a portable data storage device. In an aspect, circuitry 2440 includes circuitry 2670 configured to receive the information associated with the ingredient list of the cosmetic product from the Internet.

In an aspect, the computing device of the system includes circuitry configured to receive the information associated with the ingredient list of the cosmetic product through a user interface. For example, the individual or other user may manually enter the one or more cosmetic ingredients in the ingredient list of the cosmetic product into the computing device using a user interface, e.g., a keyboard, touch pad, microphone, or the like.

In an aspect, the ingredient list of the cosmetic product is entered into the computing device by way of scanning the ingredient label of the cosmetic product. FIG. 27 illustrates aspects of system 2400 including a scanning device. In an aspect, system 2400 includes scanning device 2700. Scanning device 2700 is operably coupled to computing device 2420 and includes circuitry 2710 configured to scan and digitize an ingredient label of the cosmetic product, the ingredient label including the ingredient list of the cosmetic product. Non-limiting aspects of scanning devices for use in scanning an ingredient label have been described above herein.

FIG. 28 illustrates further aspects of a system such as shown in FIG. 24. In an aspect, system 2400 includes circuitry 2450 configured to receive information associated with a microbe profile of an individual. In an aspect, circuitry 2450 includes circuitry 2800 configured to receive the information associated with the microbe profile of the individual from a microbe profiling device. In an aspect, system 2400 includes circuitry configured to receive the information associated with a microbe profiling device that directly detects one or more types of microbes on the skin surface of an individual. For example, the microbe profiling device can include an optical microbe profiling device that scans the skin surface with an optical energy source, e.g., light emitted from a fiber optic, laser, or light emitting diode, and detects signals emitted or reflected in situ from the microbes on the skin surface in response to the optical energy source. See, e.g., U.S. Pat. No. 8,280,471, to Rainone et al., and titled "Fiber optic based detection of fluorescent bacterial pathogens," which is incorporated herein by reference.

In an aspect, system 2400 includes circuitry configured to receive the information associated with a microbe profiling device that indirectly detects one or more types of microbes on the skin surface of an individual. For example, the microbe profiling device can include a microbe sampling component for sampling one or more types of microbes from a skin surface and a detecting component for detecting the one or more types of microbes captured with the microbe sampling component. In an aspect, the microbe profiling device includes a microbe sampling unit including a microbe-capture region (e.g., one or more materials configured to selectively or non-selectively capture one or more types of microbes from a skin surface), at least one sensor component (e.g., an optical or fluorescence sensor), a user interface (e.g., a touchscreen display), and a computing component including a microprocessor and circuitry configured to generate a microbe profile. In an aspect, system 2400 includes circuitry configured to receive the information associated with the microbe profile of the individual from a hand-held microbe profiling device including a device head for dislodging microbes from a skin surface, such as described in U.S. patent application Ser. Nos. 14/091,762, 14/091,793, and 14/091,805, each of which is incorporated herein by reference. In an aspect, system 2400 includes circuitry configured to receive the information associated with the microbe profile of the individual from a microbe profiling device that includes a rotatable microbe sampling unit including a microbe-capture region, such as described in U.S. patent application Ser. Nos. 14/091,832, and 14/091,856, each of which is incorporated herein by reference. Non-limiting aspects of microbe profiling devices have been described above herein.

In an aspect, the circuitry 2450 of system 2400 includes circuitry 2810 configured to receive the information associated with the microbe profile of the individual from a microbe profiling system. In an aspect, system 2400 includes circuitry configured to receive the information associated with the microbe profile of the individual from a microbe profiling system that includes at least one of a microbe sampling unit including a microbe-capture region, a microbe sampling device, an analyzer including at least one sensor component to detect one or more signals emitted or reflected from the microbe sampling unit, and a computing component including a processor and circuitry configured to generate a microbe profile based on sensor output from the at least one sensor component. In an aspect, system 2400 includes circuitry configured to receive the information associated with the microbe profile of the individual sampled using at least one of a mask, a mouthpiece, a strip, a swab, a brush, a sponge, or a razor. For example, system 2400 can include circuitry configured to receive the information associated with the microbe profile of the individual from a microbe profiling system that includes a mask, e.g., a pre-formed or peelable mask, which substantially conforms to the topography of the skin surface of the individual and captures and/or interacts with microbes on the skin surface upon contact. For example, system 2400 can include circuitry configured to receive the information associated with the microbe profile of the individual from a microbe profiling system that includes a mouthpiece formed from a settable material using a dental or impression tray. Other non-limiting aspects of microbe profiling systems for generating a microbe profile using a mask or a mouthpiece are described in U.S. patent application Ser. Nos. 13/975,055, 13/975,067, and 13/975,079, each of which is incorporated herein by reference.

In an aspect, system 2400 includes circuitry configured to receive the information associated with the microbe profile of the individual from a microbe profiling system that includes a kiosk. In an aspect, system 2400 includes circuitry configured to receive the information associated with the microbe profile of the individual from a microbe profiling system that includes a kit. Non-limiting aspects of a kiosk or kit for sampling a skin surface and generating a microbe profile are described in U.S. patent application Ser. No. 14/255,653, which is incorporated herein by reference.

In an aspect, circuitry of 2450 of system 2400 includes circuitry 2820 configured to receive the information associated with the microbe profile of the individual from a computing component associated with at least one of a microbe profiling device or a microbe profiling system. In an aspect, system 2400 includes circuitry configured to receive the information associated with the microbe profile of the individual from a computing component associated with at least one of a microbe profiling device or a microbe profiling system through a wireless communication. The wireless communication means can include any of a number of wireless implementations, devices, and standards, non-limiting examples of which include cellular networks, e.g., 3G, short-range point-to-point communication, e.g., wireless USB, wireless sensor networks, e.g., Bluetooth, or wireless LAN, e.g., Wi-Fi. For example, system 2400 can include circuitry configured to receive the information associated with the microbe profile of an individual via a cellular network communication. In an aspect, system 2400 includes circuitry configured to receive the information associated with the microbe profile of the individual from a computing component associated with at least one of a microbe profiling device or a microbe profiling system through a wired communication, e.g., a cable, phone, or Internet connection, provided by a telephone, cable, or fiber-optic network. In an aspect, system 2400 includes circuitry configured to receive the information associated with the microbe profile from a computing component associated with a hand-held microbe profiling device or an analyzer of a microbe profiling kit. For example, system 2400 can include circuitry configured to receive the information associated with the microbe profile of the individual from a hand-held microbe profiling device or a microbe profiling kit used in a home environment and capable of communicating through a cellular network to a computing device associated with a cosmetic supplier and/or manufacturer. For example, system 2400 can include circuitry configured to receive the information associated with the microbe profile of the individual from a kiosk or microbe profiling system associated with a medical or commercial space and capable of communicating through a telephone or cable connection with a computing device associated with a cosmetic supplier and/or manufacturer.

In an aspect, circuitry 2450 of system 2400 includes circuitry 2830 configured to receive the information associated with the microbe profile of the individual from a portable data storage device. For example, the microbe profile of the individual can be generated using a microbe profiling device or system and the microbe profile downloaded to a portable data storage device and uploaded to computing device 2420. Non-limiting examples of portable data storage devices have been described above herein.

In an aspect, circuitry 2450 of system 2400 includes circuitry 2840 configured to receive the information associated with the microbe profile of the individual from the Internet. In an aspect, the microbe profile of the individual is downloaded from a microbe profiling device, microbe profiling system, and/or portable data storage device to the Internet, e.g., a specific client website, and then uploaded from the Internet onto computing device 2420. For example, the system can include circuitry configured to receive the microbe profile of an individual from an Internet site to which the individual has downloaded his/her microbe profile. For example, the microbe profile may be downloaded to an Internet site as part of a user interaction at a medical or commercial kiosk.

Figure 29:
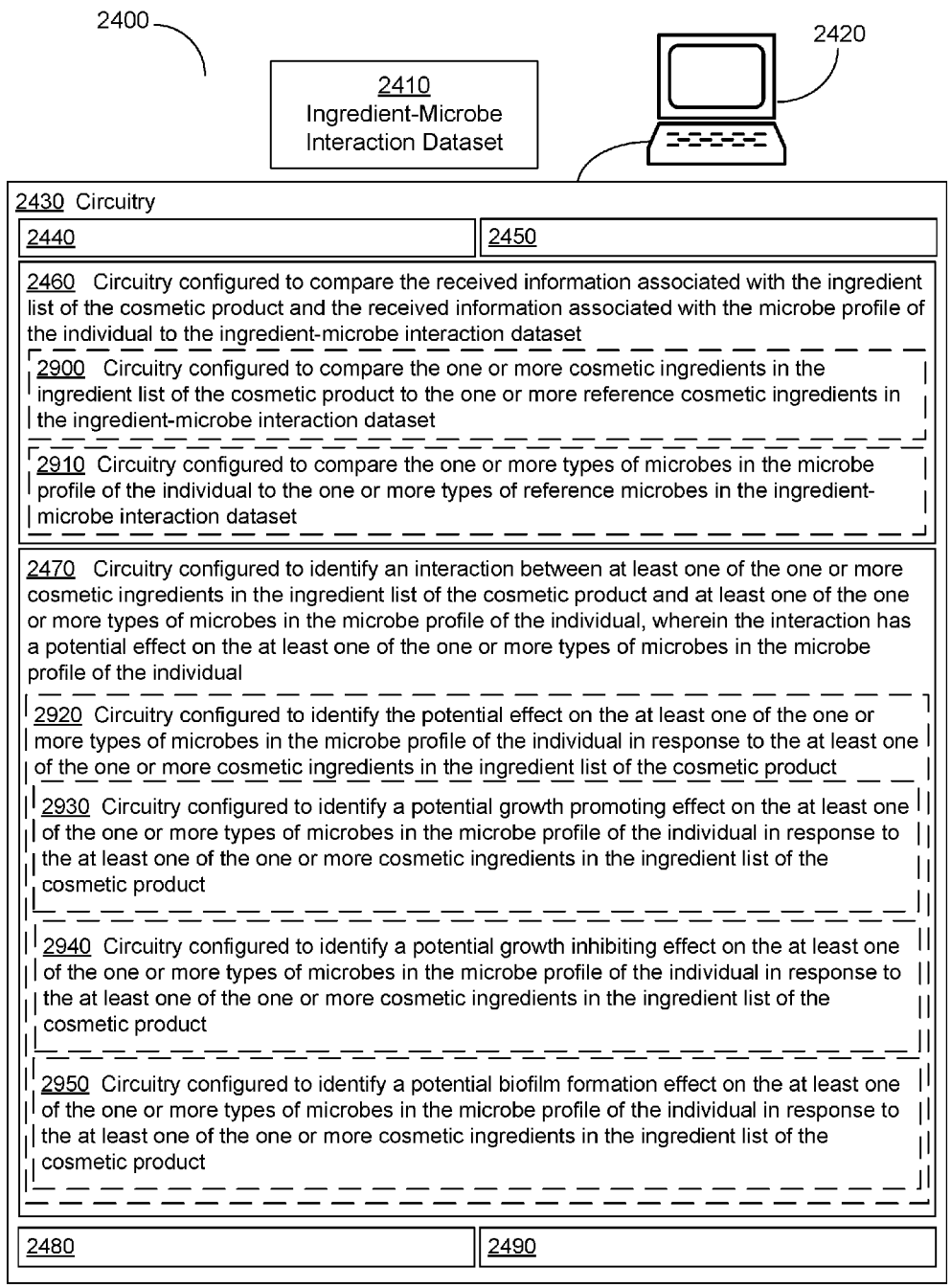
FIG. 29 shows further aspects of a system such as depicted in FIG. 24.

FIG. 29 illustrates further aspects of system 2400. System 2400 includes circuitry 2460 configured to compare the received information associated with the ingredient list of the cosmetic product and the received information associated with the microbe profile of the individual to the ingredient-microbe interaction dataset. In an aspect, system 2400 includes circuitry 2900 configured to compare the one or more cosmetic ingredients in the ingredient list of the cosmetic product to the one or more reference cosmetic ingredients in the ingredient-microbe interaction dataset. For example, the system can include circuitry configured to compare a cosmetic ingredient, e.g., stearic acid, in the ingredient list of the cosmetic product to the one or more reference cosmetic ingredients to determine any interactions of the cosmetic ingredient with the one or more types of reference microbes and by extension, the one or more types of microbe in the microbe profile of the individual. In an aspect, system 2400 includes circuitry 2910 configured to compare the one or more types of microbes in the microbe profile of the individual to the one or more types of reference microbes in the ingredient-microbe interaction dataset. For example, the system can include circuitry configured to compare an identified type of microbe, e.g., *Propionibacterium* or *Staphylococcus*, in the microbe profile of the individual to the one or more types of reference microbes to determine any interactions of the identified type of microbe with the one or more reference cosmetic ingredients and by extension, the one or more cosmetic ingredients in the ingredient list of the cosmetic product.

System 2400 includes circuitry 2470 configured to identify an interaction between at least one of the one or more cosmetic ingredients in the ingredient list of the cosmetic product and at least one of the one or more types of microbes in the microbe profile of the individual. In an aspect, system 2400 includes circuitry 2920 configured to identify the potential effect on the at least one of the one or more types of microbes in the microbe profile of the individual in response to the at least one of the one or more cosmetic ingredients in the ingredient list of the cosmetic product. In an aspect, system 2400 includes circuitry 2930 configured to identify a potential growth promoting effect on the at least one of the one or more types of microbes in the microbe profile of the individual in response to the at least one of the one or more cosmetic ingredients in the ingredient list of the cosmetic product. In an aspect, system 2400 includes circuitry 2940 configured to identify a potential growth inhibiting effect on the at least one of the one or more types of microbes in the microbe profile of the individual in response to the at least one of the one or more cosmetic ingredients in the ingredient list of the cosmetic product. In an aspect, the system includes circuitry configured to identify a potential stasis effect, e.g., neither inhibiting or promoting growth, on the at least one of the one or more types of microbes in the microbe profile of the individual in response to the at least one of the one or more cosmetic ingredients in the ingredient list of the cosmetic product. In an aspect, the system includes circuitry configured to identify a potential cytotoxic effect, e.g., killing effect, on the at least one of the one or more types of microbes in the microbe profile of the individual in response to the at least one of the one or more cosmetic ingredients in the ingredient list of the cosmetic product. In an aspect, system 2400 includes circuitry 2950 configured to identify a potential biofilm formation effect on the at least one of the one or more types of microbes in the microbe profile of the individual in response to the at least one of the one or more cosmetic ingredients in the ingredient list of the cosmetic product.

FIG. 30 illustrates further aspects of system 2400. System 2400 includes circuitry 2480 configured to recommend a modification to the ingredient list of the cosmetic product in response to the identified interaction. In an aspect, system 2400 includes circuitry 3000 configured to recommend a modification to the ingredient list of the cosmetic product to alleviate the identified interaction. For example, the system can include circuitry configured to recommend addition or subtraction of a cosmetic ingredient, e.g., a buffering agent, to alleviate an identified interaction between a cosmetic ingredient, e.g., a pH elevating agent, and a type of microbe. In an aspect, system 2400 includes circuitry 3010 configured to recommend a modification to the ingredient list of the cosmetic product to enhance the identified interaction. For example, the system can include circuitry configured to recommend addition or subtraction of a cosmetic ingredient to enhance an identified interaction between a cosmetic ingredient and a type of microbe. In an aspect, system 2400 includes circuitry 3020 configured to recommend an addition of at least one cosmetic ingredient to the ingredient list of the cosmetic product. For example, the system can include circuitry configured to recommend addition of a cosmetic ingredient to the cosmetic product to alter, e.g., alleviate or enhance, a potential growth promoting effect, a potential growth inhibiting effect, and/or a potential biofilm formation effect on a type of microbe on the skin surface of the individual in response to one or more cosmetic ingredients in the cosmetic product. In an aspect, system 2400 includes circuitry 3030 configured to recommend a subtraction of at least one cosmetic ingredient from the ingredient list of the cosmetic product. For example, the system can include circuitry configured to recommend subtraction of a cosmetic ingredient from the cosmetic product to alter, e.g., alleviate or enhance, a potential growth promoting effect, a potential growth inhibiting effect, and/or a potential biofilm formation effect on a type of microbe on the skin surface of the individual in response to one or more cosmetic ingredients in the cosmetic product. In an aspect, system 2400 includes circuitry 3040 configured to recommend a relative change in the concentration of at least one cosmetic ingredient in the ingredient list of the cosmetic product. For example, the system can include circuitry configured to recommend a relative change in concentration of a cosmetic ingredient to the cosmetic product to alter, e.g., alleviate or enhance, a potential growth promoting effect, a potential growth inhibiting effect, and/or a potential biofilm formation effect on a type of microbe on the skin surface of the individual in response to one or more cosmetic ingredients in the cosmetic product.

FIG. 31 illustrates further aspects of system 2400. In an aspect, system 2400 includes user interface 3100. User interface 3100 can include any of a number of input or output components configured to allow a user, e.g., the individual, to enter data, e.g., user information, and to receive data, e.g., the recommended modifications to the ingredient list of the cosmetic product. Non-limiting examples of user interfaces have been described above herein.

In an aspect, system 2400 further includes circuitry 3110 configured to receive user information from the individual. In an aspect, system 2400 includes circuitry configured to receive the user information from the individual through user interface 3100, e.g., a touchscreen display, a keyboard, or a microphone. In an aspect, system 2400 includes circuitry configured to receive the user information from a remote source, e.g., a personal computing device, an Internet site, or a computing component associated with a microbe profiling device, microbe profiling system, microbe profiling kit, or microbe profiling kiosk. In an aspect, system 2400 includes circuitry 3120 configured to receive at least one of age, gender, ethnicity, geographical location, skin characteristics, medical history, co-morbidities, or user preferences.

In an aspect, system 2400 includes circuitry 3130 configured to recommend a modification to the ingredient list of the cosmetic product based at least in part on user information. In an aspect, system 2400 includes circuitry 3140 configured to recommend a modification to the ingredient list of the cosmetic product based at least in part on at least one of age, gender, ethnicity, geographical location, skin characteristics, medical history, co-morbidities, or user preferences. For example, the age of a user, e.g., young versus old, may dictate the types of microbes present on a given body surface. For example, the ethnicity and/or geographical location of the user may dictate the types of microbes present on a given body surface. For example, a skin characteristic such as whether the skin surface is sebaceous, moist, or dry may dictate the types of microbes present on said skin surface. In an aspect, the skin characteristics may dictate which vehicle (cream, gel, lotion, or solution) is appropriate for a skin type.

System 2400 further includes circuitry 2490 configured to report to a user the recommended modification to the ingredient list of the cosmetic product. In an aspect, the user includes the individual for whom the microbe profile was generated. In an aspect, the user includes a second individual, e.g., a medical practitioner, a healthcare worker, a pharmacist, a cosmetologist, a technician, merchant, a supplier, or a manufacturer. In an aspect, the user includes a computing device associated with a medical or commercial entity, e.g., a supplier or manufacturer of cosmetic goods. In an aspect, the user includes at least one of a website, a social media site, or a personal computing instrument, e.g., a smart phone. In an aspect, the user includes a computing device associated with a formulation or filling device, the formulation or filling device configured to modify the cosmetic product by adding and/or subtracting one or more ingredients from a cosmetic product based on the recommended modification to the ingredient list.

In an aspect, system 2400 includes circuitry 3150 configured to report to the user the recommended modification to the ingredient list of the cosmetic product on a display associated with a computing device, e.g., computing device 2420. For example, the individual may interact with a computing device associated with a kiosk in a commercial center, the kiosk including a display for outputting information including the recommended modification to the ingredient list of the cosmetic product. In an aspect, system 2400 includes circuitry 3160 configured to report to the user the recommended modification to the ingredient list of the one cosmetic product through a printout. For example, the individual or other user may receive a printout including the recommended modification to the ingredient list of the cosmetic product from a printer operably coupled to a computing device, e.g., computing device 2420. In an aspect, system 2400 includes circuitry 3170 configured to report to the user the recommended modification to the ingredient list of the cosmetic product through at least one of a telephone call, a text message, or an e-mail. For example, an individual may receive an automated phone, text, or e-mail message in which the recommended modification to the ingredient list is provided to the individual. In an aspect, system 2400 includes circuitry 3180 configured to report the recommended modification to the ingredient list of the cosmetic product to a remote computing device. In an aspect, the remote computing device can include an individual's personal computing device, e.g., a smart phone or tablet. In an aspect, the remote computing device can include a computing device associated with a supplier and/or manufacturer of cosmetics products. For example, the system can include circuitry configured to report the recommended modification to the ingredient list of the cosmetic product to a remote computing device operably coupled to a formulating and/or filling apparatus. For example, the system can include circuitry configured to generate the recommended modification to the ingredient list of the cosmetic product based on an individual's microbe profile using a computing device at a medical practice or cosmetic counter and circuitry configured to report the recommended modification to the ingredient list of the cosmetic product to a second computing device associated with a cosmetic supplier and/or manufacturer.

In an aspect, system 2400 further includes circuitry 3185 configured to provide to an individual at least one discount coupon for purchase of a modified cosmetic product including the recommended modification to the ingredient list. In an aspect, circuitry 3185 is configured to provide a printed discount coupon to the individual. In an aspect, circuitry 3185 is configured to provide the discount coupon electronically to the individual's smart phone or to a computing device. In an aspect, circuitry 3185 is configured to provide the discount coupon as a discount code for use in making a purchase through the Internet or other web-based system.

In an aspect, system 2400 further includes circuitry 3190 configured to arrange for delivery of a modified cosmetic product including the recommended modification to the ingredient list. For example, the circuitry can be configured to arrange for delivery of a modified cosmetic product including the recommended modification to the ingredient list by way of the Postal Service, a shipping service, e.g., FedEx or UPS, or a courier. In an aspect, the system includes circuitry configured to automatically arrange for delivery of the modified cosmetic product. For example, the circuitry can be configured to automatically arrange for delivery of the modified cosmetic product by transmitting a request to a cosmetic supplier and/or manufacturer to reformulate the cosmetic product, label the modified cosmetic product for shipment, and load the modified cosmetic product for delivery. In an aspect, the system includes circuitry configured to arrange for the delivery of the modified cosmetic product to a street address, e.g., a street address of at least one of the individual's residence or workplace or a street address of at least one of a medical practice, pharmacy, or retail store for pick up by the individual. In an aspect, the system includes circuitry configured to arrange for delivery of the modified cosmetic product to a postal address, e.g., a post office box. In an aspect, the system includes circuitry configured to arrange for delivery of the modified cosmetic product to a residence, a post office, a delivery service office, a store, a pharmacy, a medical office, or a cosmetic counter. In an aspect, the system further includes circuitry configured to notify the individual by at least one of an electronic communication, a telephonic communication, or a written communication that delivery of the modified cosmetic product has been arranged.

Figure 32:
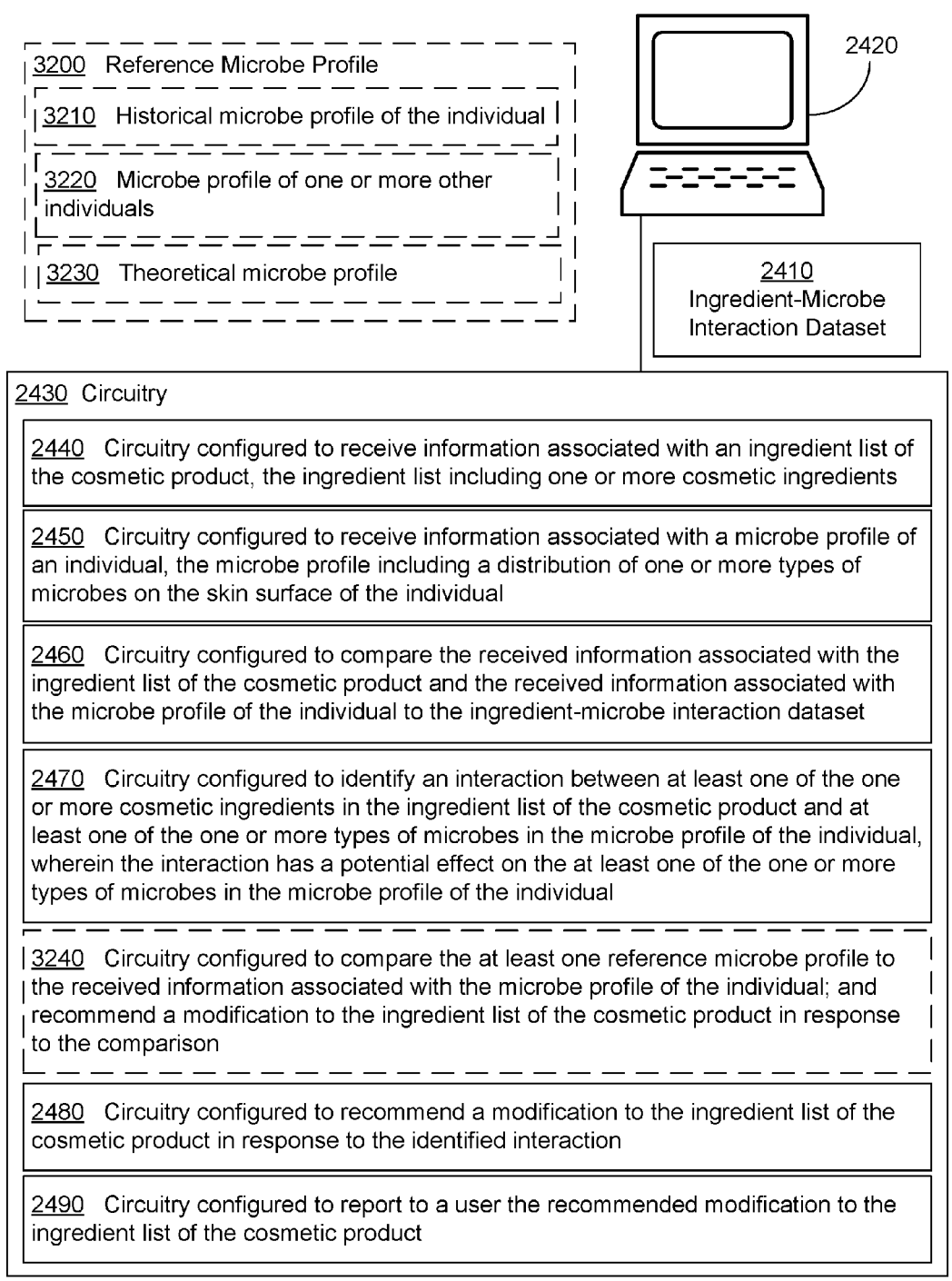
FIG. 32 shows further aspects of a system such as depicted in FIG. 24.

FIG. 32 illustrates further aspects of system 2400. In an aspect, system 2400 includes ingredient-microbe interaction dataset 2410, computing device 2420, circuitry 2430, and at least one reference microbe profile 3200. In an aspect, circuitry 2430 further includes circuitry 3240 configured to compare the at least one reference microbe profile to the received information associated with the microbe profile of the individual; and recommend a modification to the ingredient list of the cosmetic product in response to the comparison.

In an aspect, at least one reference microbe profile 3200 includes at least one historical microbe profile of the individual 3210. In an aspect, the at least one historical microbe profile of the individual includes at least one microbe profile generated at a previous point in time, e.g., at a younger age. In an aspect, the at least one historical microbe profile of the individual can include at least one microbe profile generated one or more days, one or more weeks, and/or one or more years previous to a current point in time. In an aspect, the at least one historical microbe profile of the individual can include at least one microbe profile generated at a point in time before onset of a condition and/or before onset of a treatment.

In an aspect, at least one reference microbe profile 3200 includes at least one microbe profile from one or more other individuals 3220. For example, the at least one microbe profile from one or more other individuals can include a microbe profile averaged or normalized from a number of individuals matched to the individual, e.g., matched in age, gender, ethnicity, geographical location, medical condition, or co-morbidities. In an aspect, the at least one microbe profile from one or more other individuals can include a microbe profile averaged or normalized from one or more idealized individuals based on the user's preferences of the individual. For example, the at least one reference microbe profile can include a microbe profile of one or more individuals of an age, gender, ethnicity, geographical location, skin characteristics, medical history, or co-morbidities that the individual wishes to emulate. For example, the at least one microbe profile from one or more other individuals can include a microbe profile of an admired individual, e.g., a celebrity.

In an aspect, at least one reference microbe profile 3200 includes at least one theoretical microbe profile 3230. In an aspect, the at least one theoretical microbe profile includes a microbe profile compiled from a number of microbe profiles to form a standardized microbe profile. In an aspect, the at least one theoretical microbe profile includes an optimized or ideal microbe profile, e.g., a microbe profile including a generally recognized balance of beneficial commensal microbes. In an aspect, the at least one theoretical microbe profile includes a marginal or bad microbe profile. For example, the theoretical microbe profile might include a disease- or condition-associated microbe profile, e.g., acne, psoriasis, Crohn's disease, diabetes, or other disease or condition.

In an aspect, at least one reference microbe profile 3200 is incorporated into a memory component of computing device 2420. In an aspect, at least one reference microbe profile 3200 is accessible to computing device 2420 from a portable data storage device. For example, the at least one reference microbe profile can be stored on a portable data storage device, e.g., a CD-ROM or a memory stick or card, and accessed by the computing device of the system to compare with the microbe profile of the individual. In an aspect, at least one reference microbe profile is accessible to computing device 2420 from a remote computing device. For example, the at least one reference microbe profile can be stored on a cloud-based server and accessible through a web-connection, e.g., the Internet, by the computing device of the system.

In an aspect, at least one reference microbe profile 3200 is updatable. In an aspect, the at least one reference microbe profile is updated every time a new microbe profile is generated for the individual. For example, each newly generated microbe profile of the individual can become part of a collective historical microbe profile of the individual. In an aspect, the at least one reference microbe profile is updated in response to changes in standards or norms. In an aspect, the at least one reference microbe profile is updated in response to changes in user information. For example, the at least one reference microbe profile used for comparison with the microbe profile of the individual can be matched to changes in the individual's user information, e.g., changes in age, geographical location, skin characteristics, medical history, co-morbidities, or user preferences.

In an aspect, system 2400 includes circuitry configured to compare the at least one reference microbe profile to the received information associated with the microbe profile of the individual. In an aspect, the system includes an algorithm or alignment software for noting similarities and differences between the microbe profile of the individual and the at least one reference microbe profile. In an aspect, the system includes circuitry configured to compare the microbe profile of the individual with at least one historical microbe profile of the individual. For example, the system can include circuitry configured to compare the microbe profile of the individual with at least one microbe profile of the individual generated at an earlier point in time, e.g., before the use of the cosmetic product. In an aspect, the system includes configured to compare the microbe profile of the individual with at least one microbe profile of one or more other individuals. For example, the system can include circuitry configured to compare the microbe profile of the individual with at least one microbe profile of one or more other individuals who have used the cosmetic product. For example, the system can include circuitry configured to compare the microbe profile of the individual with at least one microbe profile of one or more other matched individuals, e.g., matched based on age, gender, ethnicity, geographical location, skin characteristics, medical history, or co-morbidities. For example, the system can include circuitry configured to compare the microbe profile of the individual with a microbe profile of a celebrity or other individual admired by the individual. In an aspect, the system includes circuitry configured to compare the microbe profile of the individual with at least one theoretical microbe profile. For example, the system can include circuitry configured to compare the microbe profile of the individual with at least one theoretical microbe profile created for the cosmetic product.

With reference to FIG. 33, shown is a flowchart of a method for modifying a cosmetic product. The method includes receiving information associated with an ingredient list of the cosmetic product, the ingredient list of the cosmetic product including one or more cosmetic ingredients, as shown in block 3300; receiving information associated with a microbe profile of an individual, the microbe profile including a distribution of one or more types of microbes on a skin surface of an individual, as shown in block 3310; comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes, as shown in block 3320; identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual, as shown in block 3330; recommending a modification to the ingredient list of the cosmetic in response to the identified interaction, as shown in block 3340; and reporting to the user the recommended modification to the ingredient list of the cosmetic product, as shown in block 3350.

In an aspect, a method of modifying a cosmetic product, such as described in FIG. 33, is implemented on a computing device. In an aspect, the method is implemented on a home computing device. In an aspect, the method is implemented on a computing device associated with a medical practice or a commercial site, e.g., a cosmetic counter. In an aspect, the method is implemented on a computing device associated with a cosmetic supplier, a cosmetic distributer, and/or a cosmetic manufacturer. In an aspect, the method is implemented on computing device associated with a microbe profiling device. In an aspect, the method is implemented on a computing device associated with a microbe profiling system. In an aspect, the method is implemented on a computing device associated with a kiosk, e.g., a cosmetic dispensing kiosk associated with a medical practice or a commercial site.

FIG. 34 shows further aspects of a method such as shown in FIG. 33. The method includes receiving information associated with an ingredient list of the cosmetic product. In an aspect, the method includes receiving information associated with the one or more cosmetic ingredients in the ingredient list of the cosmetic product in block 3400. In an aspect, the method includes receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax in the ingredient list of the cosmetic product, as shown in block 3410. In an aspect, the method includes receiving information associated with at least one of one or more probiotic agents, one or more prebiotics agents, or one or more therapeutic agents in the ingredient list of the cosmetic product, as shown in block 3420. In an aspect, the method includes receiving the information associated with the ingredient list of the cosmetic product from a remote source, as shown in block 3430. In an aspect, the method includes receiving the information associated with the ingredient list of the cosmetic product from a cosmetic distributer, a cosmetic manufacturer, or a cosmetic formulary, as shown in block 3440. In an aspect, the method includes receiving the information associated with the ingredient list of the cosmetic product from a portable data storage device, as shown in block 3450. In an aspect, the method includes receiving the information associated with the ingredient list of the cosmetic product from a scanning device, as shown in block 3460.

FIG. 35 illustrates further aspects of a method such as shown in FIG. 33. The method includes receiving information associated with a microbe profile of an individual, the microbe profile including a distribution of one or more types of microbes on a skin surface of the individual, as shown in block 3310. Non-limiting aspects of microbe profiles have been described above herein. In an aspect, the method includes receiving the information associated with the microbe profile of the individual from a microbe profiling device, as shown in block 3500. For example, the method can include receiving the information associated with the microbe profile of the individual from a hand-held microbe profiling device through a wireless communication. In an aspect, the method includes receiving the information associated with the microbe profile of the individual from a microbe profiling system, as shown in block 3510. For example, the method can include receiving the information associated with the microbe profile of the individual from a microbe profiling kiosk located in a shopping mall or a cosmetic store. Non-limiting aspects of microbe profiling devices and systems have been described above herein.

In an aspect, the method includes receiving the information associated with the microbe profile of the individual from a computing component associated with at least one of a microbe profiling device or a microbe profiling system, as shown in block 3520. In an aspect, the method includes receiving the information associated with the microbe profile of the individual from a computing component associated with at least one of a microbe profiling device or a microbe profiling system through a wireless communication, e.g., a cellular network communication. In an aspect, the method includes receiving the information associated with the microbe profile of the individual from a computing component associated with at least one of a microbe profiling device or a microbe profiling system through a wired communication, e.g., fiber-optic network. In an aspect, the method includes receiving the information associated with the microbe profile from a computing component associated with a hand-held microbe profiling device or an analyzer of a microbe profiling kit. For example, the method can include receiving the information associated with the microbe profile of the individual from a hand-held microbe profiling device or a microbe profiling kit used in a home environment and capable of communicating through a cellular network to a computing device associated with a cosmetic supplier and/or manufacturer. For example, the method can include receiving the information associated with the microbe profile of the individual from a kiosk or microbe profiling system associated with a medical or commercial space and capable of communicating through a telephone or cable connection with a computing device associated with a cosmetic supplier and/or manufacturer.

In an aspect, the method includes receiving the information associated with a microbe profile of the individual from a portable data storage device, as shown in block 3530. For example, the microbe profile of the individual can be generated using a microbe profiling device or system, downloaded to a portable data storage device, and uploaded to a computing device, e.g., a computing device for performing the method. Non-limiting examples of portable data storage devices have been describe above herein.

In an aspect, the method includes receiving the information associated with the microbe profile of the individual from the Internet, as shown in block 3540. In an aspect, the microbe profile of the individual is downloaded from a microbe profiling device, microbe profiling system, and/or portable data storage device to the Internet, e.g., a specific client website, and then uploaded from the Internet onto a computing device for performing the method. For example, the method can include receiving the microbe profile of an individual from an Internet site to which the individual downloaded his/her microbe profile. For example, the microbe profile may be downloaded to an Internet site as part of a user interaction at a medical or commercial kiosk, or through an analyzer as part of an at-home profiling kit.

The method of FIG. 33 includes comparing the received information associated with the ingredient list of the cosmetic product and the received information associated with the microbe profile of the individual to the ingredient-microbe interaction dataset, the ingredient-microbe interaction dataset including information associated with interactions between one or more reference cosmetic ingredients and one or more types of reference microbes, as shown in block 3320. In an aspect, the ingredient-microbe interaction dataset is stored in a memory component of a computing device used for performing the method. In an aspect, the ingredient-microbe interaction dataset is accessed from a remote computing device or remote server through a web or Internet connection. In an aspect, the ingredient-microbe interaction dataset is stored on a portable data storage device, e.g., a CD ROM or a memory card or stick.

Figure 36:
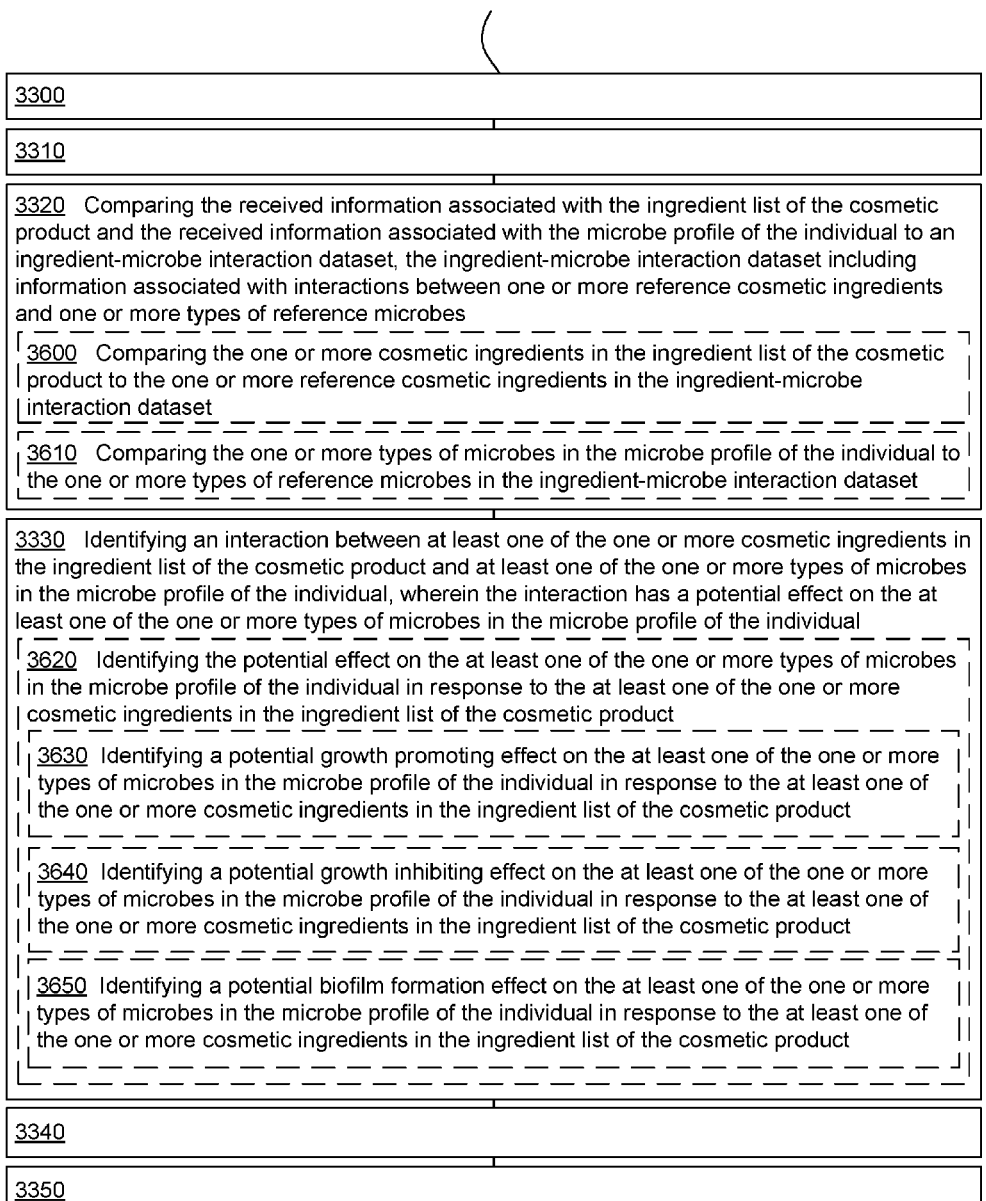
FIG. 36 depicts further aspects of a method such as illustrated in FIG. 33.

FIG. 36 illustrates further aspects of a method such as shown in FIG. 33. In an aspect, the method includes comparing the one or more cosmetic ingredients in the ingredient list of the cosmetic product with the one or more reference cosmetic ingredients in the ingredient-microbe interaction dataset, as shown in block 3600. For example, the method includes comparing a cosmetic ingredient, e.g., stearic acid, in the ingredient list of the cosmetic product to the one or more reference cosmetic ingredients to determine any interactions of the cosmetic ingredient with one more types of reference microbes. In an aspect, the method includes comparing the one or more types of microbes in the microbe profile of the individual to the one or more types of reference microbes in the ingredient-microbe interaction dataset, as shown in block 3610. For example, the method includes comparing an identified type of microbe, e.g., *Staphylococcus epidermidis*, and comparing it with the reference microbes to determine any interactions of the identified type of microbe with the one or more reference cosmetic ingredients.

The method further includes identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual. For example, the method can include identifying an interaction between a cosmetic ingredient in a cosmetic product with a type of microbe in the microbe profile of the individual from the comparison of the microbe profile and the ingredient list of the cosmetic product to the ingredient-microbe interaction dataset, the interaction having a potential effect on the at least one of the one or more types of microbes in the microbe profile of the individual. In an aspect, the method includes identifying the potential effect on the at least one of the one or more types of microbes in the microbe profile of the individual in response to at least one of the one or more cosmetic ingredients in the ingredient list of the cosmetic product, as shown in block 3620. In an aspect, the method includes identifying a potential growth promoting effect on the at least one of the one or more types of microbes in the microbe profile of the individual in response to at least one of the one or more cosmetic ingredients in the ingredient list of the cosmetic product, as shown in block 3630. In an aspect, the method includes identifying a potential growth inhibiting effect on the at least one of the one or more types of microbes in the microbe profile of the individual in response to at least one of the one or more cosmetic ingredients in the ingredient list of the cosmetic product, as shown in block 3640. In an aspect, the method includes identifying a potential stasis effect on the at least one of the one or more types of microbes in the microbe profile of the individual in response to at least one of the one or more cosmetic ingredients in the ingredient list of the cosmetic product. In an aspect, the method includes identifying a potential cytotoxic effect on the at least one of the one or more types of microbes in the microbe profile of the individual in response to at least one of the one or more cosmetic ingredients in the ingredient list of the cosmetic product. In an aspect, the method includes identifying a potential biofilm formation effect on the at least one of the one or more types of microbes in the microbe profile of the individual in response to at least one of the one or more cosmetic ingredients in the ingredient list of the cosmetic product, as shown in block 3650.

The method further includes recommending a modification to an ingredient list of the cosmetic product in response to the identified interaction. FIG. 37 illustrates further aspects of a method such as shown in FIG. 33. In an aspect, the method includes recommending a modification to the ingredient list of the cosmetic product to alleviate the identified interaction, as shown in block 3700. In an aspect, the method includes recommending a modification to the ingredient list of the cosmetic product to lessen the identified interaction. In an aspect, the method includes recommending a modification to the ingredient list of the cosmetic product to eliminate the identified interaction. In an aspect, the method includes recommending a modification to the ingredient list of the cosmetic product to alleviate the potential effect on the at least one of the one or more types of microbes in the microbe profile of the individual in response to the at least one of the one or more cosmetic ingredients in the ingredient list of the cosmetic product. In an aspect, the method includes recommending a modification to the ingredient list of the cosmetic product to alleviate at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients in the ingredient list of the cosmetic product.

In an aspect, the method includes recommending a modification to the ingredient list of the cosmetic product to enhance the identified interaction, as shown in block 3710. In an aspect, the method includes recommending a modification to the ingredient list of the cosmetic product to enhance the potential effect on the at least one of the one or more types of microbes in the microbe profile of the individual in response to the at least one of the one or more cosmetic ingredients in the ingredient list of the cosmetic product. In an aspect, the method includes recommending a modification to the ingredient list of the cosmetic product to enhance at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients in the ingredient list of the cosmetic product.

In an aspect, the method includes recommending an addition of at least one cosmetic ingredient to the ingredient list of the cosmetic product, as shown in block 3720. In an aspect, the method includes recommending an addition of at least one cosmetic ingredient to the ingredient list of the cosmetic product to alleviate or enhance the potential effect on the at least one of the one or more types of microbes in the microbe profile of the individual in response to at least one of the one or more cosmetic ingredients in the ingredient list of the cosmetic product. In an aspect, the method includes recommending an addition of at least one cosmetic ingredient to the ingredient list of the cosmetic product to alleviate or enhance at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients in the ingredient list of the cosmetic product.

In an aspect, the method includes recommending a subtraction of at least one cosmetic ingredient from the ingredient list of the cosmetic product, as shown in block 3730. In an aspect, the method includes recommending a subtraction of at least one cosmetic ingredient from the ingredient list of the cosmetic product to alleviate or enhance the potential effect on the at least one of the one or more types of microbes in the microbe profile of the individual in response to at least one of the one or more cosmetic ingredients in the ingredient list of the cosmetic product. In an aspect, the method includes recommending a subtraction of at least one cosmetic ingredient from the ingredient list of the cosmetic product to alleviate or enhance at least one a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients in the ingredient list of the cosmetic product.

In an aspect, the method includes recommending a relative change in concentration of at least one cosmetic ingredient in the ingredient list of the cosmetic product, as shown in block 3740. In an aspect, the method includes recommending a relative change in concentration of at least one cosmetic ingredient in the ingredient list of the cosmetic product to alleviate or enhance the potential effect on the at least one of the one or more types of microbes in the microbe profile of the individual in response to at least one of the one or more cosmetic ingredients in the ingredient list of the cosmetic product. In an aspect, the method includes recommending a relative change in concentration of at least one cosmetic ingredient in the ingredient list of the cosmetic product to alleviate or enhance at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients in the ingredient list of the cosmetic product.

FIG. 38 illustrates further aspects of a method such as shown in FIG. 33. In an aspect, the method of FIG. 33 further includes receiving user information from the individual, as shown in block 3800. In an aspect, the method includes receiving the user information from the individual through a user interface, e.g., a touchscreen display, a keyboard, or a microphone. In an aspect, the method includes receiving the user information from a remote source, e.g., a personal computing device, an Internet site, or a computing component associated with a microbe profiling device, microbe profiling system, microbe profiling kit, or microbe profiling kiosk. In an aspect, the method includes receiving at least one of age, gender, ethnicity, geographical location, skin characteristics, medical history, co-morbidities, or user preferences, as shown in block 3810.

In an aspect, the method further includes recommending a modification to the ingredient list of the cosmetic product based at least in part on user information, as shown in block 3820. In an aspect, the method includes recommending a modification to the ingredient list of the cosmetic product based at least in part on at least one of age, gender, ethnicity, geographical location, skin characteristics, medical history, co-morbidities, or user preferences, as shown in block 3830. For example, the method can include recommending a modification to the ingredient list of the cosmetic product based at least in part on the age of the individual in addition to the identified interaction between a cosmetic ingredient and a type of microbe in the microbe profile of the individual.

The method of FIG. 33 further includes reporting to a user the recommended modification to the ingredient list of the cosmetic product. In an aspect, the user can include the individual, another individual, or a computing device. In an aspect, the method includes reporting to the user the recommended modification to the ingredient list of the cosmetic product on a display associated with a computing device, as shown in block 3840. In an aspect, the method includes reporting to the user the recommended modification to the ingredient list of the cosmetic product through a printout, as shown in block 3850. In an aspect, the method includes reporting to the user the recommended modification to the ingredient list of the cosmetic product through at least one of a telephone call, a text message, or an e-mail, as shown in block 3860. In an aspect, the method includes reporting the recommended modification to the ingredient list of the cosmetic product to a computing device, as shown in block 3870.

In an aspect, the method of FIG. 33 further includes providing to the individual at least one discount coupon for purchase of the modified cosmetic product including the recommended modification to the ingredient list, as shown in block 3880. In an aspect, the method includes providing to the individual at least one printed discount coupon. In an aspect, the method includes providing at least one discount coupon electronically to the individual's smart phone or to a computing device. In an aspect, the method includes providing the discount coupon as a discount code for use in making a purchase through the Internet or other web-based system.

In an aspect, the method of FIG. 33 further includes arranging for delivery of a modified cosmetic product including the recommended modification to the ingredient list, as shown in block 3890. For example, the method includes arranging for delivery of a modified cosmetic product by way of the Postal Service, a shipping service, e.g., FedEx or UPS, or a courier. In an aspect, the method includes automatically arranging for delivery of the modified cosmetic product. In an aspect, the method includes arranging for the delivery of the modified cosmetic product to a street address. In an aspect, the method includes arranging for the delivery of the modified cosmetic product to a postal address, e.g., a post office box. In an aspect, the method includes arranging for the delivery of the modified cosmetic product to a residence, a post office, a delivery service office, a store, a pharmacy, a medical office, or a cosmetic counter. In an aspect, the method further includes notifying the individual through at least one of an electronic communication, a telephonic communication, or a written communication that delivery of the modified cosmetic product has been arranged.

FIG. 39 illustrates a system for modifying a cosmetic product. System 3900 includes circuitry 3910. Circuitry 3910 includes circuitry 3920 for receiving information associated with an ingredient list of the cosmetic product, the ingredient list of the cosmetic product including one or more cosmetic ingredients; circuitry 3930 for receiving information associated with a microbe profile of an individual, the microbe profile including a distribution of one or more types of microbes on a skin surface of the individual; circuitry 3940 for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes; circuitry 3950 for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual; circuitry 3960 for recommending a modification to the ingredient list of the cosmetic in response to the identified interaction; and circuitry 3970 for reporting to the user the recommended modification to the ingredient list of the cosmetic product.

FIG. 40 illustrates further aspects of system 3900. In an aspect, system 3900 includes computing device 4000. Non-limiting aspects of computing devices have been described above herein. In an aspect, computing device 4000 is a personal computing device. In an aspect, computing device 4000 is associated with a medical practice or a commercial site, e.g., a cosmetic counter. In an aspect, computing device 4000 is associated with a cosmetic supplier, a cosmetic distributer, and/or a cosmetic manufacturer. In an aspect, computing device 4000 is associated with a microbe profiling device. In an aspect, computing device 4000 is associated with a microbe profiling system. In an aspect, computing device 4000 is associated with a kiosk, e.g., a cosmetic dispensing kiosk associated with a medical practice or a commercial site. In an aspect, computing device 4000 includes circuitry 3910 including circuitry 3920 for receiving information associated with an ingredient list of the cosmetic product, the ingredient list of the cosmetic product including one or more cosmetic ingredients; circuitry 3930 for receiving information associated with a microbe profile of an individual, the microbe profile including a distribution of one or more types of microbes on a skin surface of an individual; circuitry 3940 for comparing the received information associated with the ingredient list of the cosmetic product and the received information associated with the microbe profile of the individual to an ingredient-microbe interaction dataset, the ingredient-microbe interaction dataset including information associated with interactions between one or more reference cosmetic ingredients and one or more types of reference microbes; circuitry 3950 for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more types of microbes in the microbe profile of the individual; circuitry 3960 for recommending a modification to the ingredient list of the cosmetic in response to the identified interaction; and circuitry 3970 for reporting to the user the recommended modification to the ingredient list of the cosmetic product.

FIG. 41 illustrates further aspects of system 3900. System 3900 includes circuitry 3920 for receiving information associated with an ingredient list of the cosmetic product. In an aspect, system 3900 includes circuitry 4100 for receiving information associated with the one or more cosmetic ingredients in the ingredient list of the cosmetic product. In an aspect, system 3900 includes circuitry 4110 for receiving information associated with at least one of an abrasive, an absorbent, an alcohol, an analgesic, an anticaking agent, an antifoaming agent, an antioxidant, a binder, an astringent, a buffering agent, a bulking agent, a chelating agent, a colorant, a corrosion inhibitor, a deodorant, an emolient, an emulsion stabilizer, an exfoliant, a film former, a fragrance, a humectant, a hydrating agent, a lipid, a lytic agent, a metal, a mineral, a moisturizing agent, a nanoparticle, an oil, an opacifying agent, a pH adjuster, a paraben, a petroleum derivative, a polymer, a preservative, a propellant, a reducing agent, a skin-conditioning agent, a skin protectant, a slip modifier, a solvent, a sunscreen agent, a surface modifier, a surfactant, a suspending agent, a viscosity controlling agent, a viscosity decreasing agent, a viscosity increasing agent, or a wax in the ingredient list of the cosmetic product. In an aspect, system 3900 includes circuitry 4120 for receiving information associated with at least one of one or more probiotic agents, one or more prebiotics agents, or one or more therapeutic agents in the ingredient list of the cosmetic product. In an aspect, system 3900 includes circuitry 4130 for receiving the information associated with the ingredient list of the cosmetic product from a remote source. In an aspect, system 3900 includes circuitry 4140 for receiving the information associated with the ingredient list of the cosmetic product from a cosmetic distributer, a cosmetic manufacturer, or a cosmetic formulary. In an aspect, system 3900 includes circuitry 4150 for receiving the information associated with the ingredient list of the cosmetic product from a portable data storage device. In an aspect, system 3900 includes circuitry 4160 for receiving the information associated with the ingredient list of the cosmetic product from a scanning device.

FIG. 42 illustrates further aspects system 3900. In an aspect, system 3900 includes circuitry 4200 for receiving the information associated with the microbe profile of the individual from a microbe profiling device. In an aspect, system 3900 includes circuitry 4210 for receiving the information associated with the microbe profile of the individual from a microbe profiling system. In an aspect, system 3900 includes circuitry 4220 for receiving the information associated with the microbe profile of the individual from a computing component associated with at least one of a microbe profiling device or a microbe profiling system. Non-limiting aspects of microbe profiling devices and systems have been described above herein. In an aspect, system 3900 includes circuitry 4230 for receiving the information associated with a microbe profile of the individual from a portable data storage device. Non-limiting examples of portable data storage devices have been describe above herein. In an aspect, system 3900 includes circuitry 4240 for receiving the information associated with the microbe profile of the individual from at least one of a remote computing device, a remote server, or the Internet.

FIG. 43 illustrates further aspects system 3900. System 3900 includes circuitry 3940 for comparing the received information associated with the ingredient list of the cosmetic product and the received information associated with the microbe profile of the individual to the ingredient-microbe interaction dataset, the ingredient-microbe interaction dataset including information associated with interactions between one or more reference cosmetic ingredients and one or more types of reference microbes. In an aspect, system 3900 includes circuitry 4300 for comparing the one or more cosmetic ingredients in the ingredient list of the cosmetic product with the one or more reference cosmetic ingredients in the ingredient-microbe interaction dataset. In an aspect, system 3900 includes circuitry 4310 for comparing the one or more types of microbes in the microbe profile of the individual to the one or more types of reference microbes in the ingredient-microbe interaction dataset.

System 3900 further includes circuitry 3950 for identifying an interaction between at least one of the one or more cosmetic ingredients in the ingredient list of the cosmetic product and at least one of the one or more types of microbes in the microbe profile of the individual, wherein the interaction has a potential effect on the at least one of the one or more cosmetic ingredients. In an aspect, system 3900 includes circuitry 4320 for identifying the potential effect on the at least one of the one or more types of microbes in the microbe profile of the individual in response to at least one of the one or more cosmetic ingredients in the ingredient list of the cosmetic product. In an aspect, system 3900 includes circuitry 4330 for identifying a potential growth promoting effect on the at least one of the one or more types of microbes in the microbe profile of the individual in response to at least one of the one or more cosmetic ingredients in the ingredient list of the cosmetic product. In an aspect, system 3900 includes circuitry 4340 for identifying a potential growth inhibiting effect on the at least one of the one or more types of microbes in the microbe profile of the individual in response to at least one of the one or more cosmetic ingredients in the ingredient list of the cosmetic product. In an aspect, system 3900 includes circuitry 4350 for identifying a potential biofilm formation effect on the at least one of the one or more types of microbes in the microbe profile of the individual in response to at least one of the one or more cosmetic ingredients in the ingredient list of the cosmetic product.

System 3900 includes circuitry 3960 for recommending a modification to an ingredient list of the cosmetic product in response to the identified interaction. FIG. 44 illustrates further aspects system 3900. In an aspect, system 3900 includes circuitry 4400 for recommending a modification to the ingredient list of the cosmetic product to alleviate the identified interaction. In an aspect, the system includes circuitry for recommending a modification to the ingredient list of the cosmetic product to lessen the identified interaction. In an aspect, the system includes circuitry for recommending a modification to the ingredient list of the cosmetic product to eliminate the identified interaction. In an aspect, the system includes circuitry for recommending a modification to the ingredient list of the cosmetic product to alleviate the potential effect on the at least one of the one or more types of microbes in the microbe profile of the individual in response to the at least one of the one or more cosmetic ingredients. In an aspect, the system includes circuitry for recommending a modification to the ingredient list of the cosmetic product to alleviate at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients.

In an aspect, system 3900 includes circuitry 4410 for recommending a modification to the ingredient list of the cosmetic product to enhance the identified interaction. In an aspect, the system includes circuitry for recommending a modification to the ingredient list of the cosmetic product to enhance the potential effect on the at least one of the one or more types of microbes in the microbe profile of the individual in response to the at least one of the one or more cosmetic ingredients. In an aspect, the system includes circuitry for recommending a modification to the ingredient list of the cosmetic product to enhance at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients.

In an aspect, system 3900 includes circuitry 4420 for recommending an addition of at least one cosmetic ingredient to the ingredient list of the cosmetic product. In an aspect, the system includes circuitry for recommending an addition of at least one cosmetic ingredient to the ingredient list of the cosmetic product to alleviate or enhance the potential effect on the at least one of the one or more types of microbes in the microbe profile of the individual in response to at least one of the one or more cosmetic ingredients. In an aspect, the system includes circuitry for recommending an addition of at least one cosmetic ingredient to the ingredient list of the cosmetic product to alleviate or enhance at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients.

In an aspect, system 3900 includes circuitry 4430 for recommending a subtraction of at least one cosmetic ingredient from the ingredient list of the cosmetic product. In an aspect, the system includes circuitry for recommending a subtraction of at least one cosmetic ingredient from the ingredient list of the cosmetic product to alleviate or enhance the potential effect on the at least one of the one or more types of microbes in the microbe profile of the individual in response to at least one of the one or more cosmetic ingredients. In an aspect, the system includes circuitry for recommending a subtraction of at least one cosmetic ingredient from the ingredient list of the cosmetic product to alleviate or enhance at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients.

In an aspect, system 3900 includes circuitry 4440 for recommending a relative change in concentration of at least one cosmetic ingredient in the ingredient list of the cosmetic product. In an aspect, the system includes circuitry for recommending a relative change in concentration of at least one cosmetic ingredient in the ingredient list of the cosmetic product to alleviate or enhance the potential effect on the at least one of the one or more types of microbes in the microbe profile of the individual in response to at least one of the one or more cosmetic ingredients. In an aspect, the system includes circuitry for recommending a relative change in concentration of at least one cosmetic ingredient in the ingredient list of the cosmetic product to alleviate or enhance at least one of a potential growth promoting effect, a potential growth inhibiting effect, a potential stasis effect, a potential cytotoxic effect, or a potential biofilm formation effect on the at least one of the one or more types of microbes in the microbe profile of the individual in response to the at least one of the one or more cosmetic ingredients.

FIG. 45 illustrates further aspects of system 3900. In an aspect, system 3900 includes circuitry 4500 for receiving user information from the individual. In an aspect, system 3900 includes circuitry 4510 for receiving at least one of age, gender, ethnicity, geographical location, skin characteristics, medical history, co-morbidities, or user preferences. In an aspect, system 3900 includes circuitry 4520 for recommending a modification to the ingredient list of the cosmetic product based at least in part on user information. In an aspect, system 3900 includes circuitry 4530 for recommending a modification to the ingredient list of the cosmetic product based at least in part on at least one of age, gender, ethnicity, geographical location, skin characteristics, medical history, co-morbidities, or user preferences.

System 3900 includes circuitry 3970 for reporting to a user the recommended modification to the ingredient list of the cosmetic product. In an aspect, system 3900 includes circuitry 4540 for reporting to the user the recommended modification to the ingredient list of the cosmetic product on a display associated with a computing device. In an aspect, system 3900 includes circuitry 4550 for reporting to the user the recommended modification to the ingredient list of the cosmetic product through a printout. In an aspect, system 3900 includes circuitry 4560 for reporting to the user the recommended modification to the ingredient list of the cosmetic product through at least one of a telephone call, a text message, or an e-mail. In an aspect, system 3900 includes circuitry 4570 for reporting the recommended modification to the ingredient list of the cosmetic product to a computing device.

In an aspect, system 3900 further includes circuitry 4580 for providing to the individual at least one discount coupon for purchase of the modified cosmetic product including the recommended modification to the ingredient list. In an aspect, the system includes circuitry for providing to the individual at least one printed discount coupon. In an aspect, the system includes circuitry for providing at least one discount coupon electronically to the individual's smart phone or to a computing device. In an aspect, the system includes circuitry for providing the discount coupon as a discount code for use in making a purchase through the Internet or other web-based system.

In an aspect, system 3900 further includes circuitry 4590 for arranging for delivery of a modified cosmetic product including the recommended modification to the ingredient list. For example, the system can include circuitry for arranging for delivery of a modified cosmetic product by way of the Postal Service, shipping service, e.g., FedEx or UPS, or courier. In an aspect, the system includes circuitry for automatically arranging for delivery of the modified cosmetic product. In an aspect, the system includes circuitry for arranging for the delivery of the modified cosmetic product to a street address. In an aspect, the system includes circuitry for arranging for the delivery of the modified cosmetic product to a postal address, e.g., a post office box. In an aspect, the system includes circuitry for arranging for the delivery of the modified cosmetic product to a residence, a post office, a delivery service office, a store, a pharmacy, a medical office, or a cosmetic counter. In an aspect, the system includes circuitry for notifying the individual by at least one of an electronic communication, a telephonic communication, or a written communication that delivery of the modified cosmetic product has been arranged.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors. A data processing system can be implemented utilizing suitable commercially available components, such as those typically found in data computing/communication and/or network computing/communication systems.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

PROPHETIC EXAMPLE 1

A System for Modifying a Cosmetic Product

A system is described for modifying a cosmetic product. The system includes an ingredient-microbe interaction dataset and a computing device including a processor and circuitry. The system is associated with a cosmetic supplier that formulates personalized cosmetic products based on the microbe profile of a given individual.

The system includes an ingredient-microbe interaction dataset including information associated with interactions between one or more reference cosmetic ingredients and one or more types of reference microbes. The ingredient-microbe interaction dataset is stored in an accessible server managed by the cosmetic supplier, and is routinely updated as more interaction information becomes available. The reference microbes include one or more types of microbes within the genus of *Candida, Bacillus,* and *Pseudomonas*. The ingredient-microbe interaction dataset includes information associated with interactions of reference cosmetic ingredients, e.g., various hydrocarbon, silicone, alcohol, ester, and fatty acid components of cosmetic products, with the one or more types of reference microbes. The interactions include metabolism of the reference cosmetic ingredients leading to potential effects on the cosmetic product, e.g., potential effects on color, texture, pH, and/or odor of the cosmetic product.

The computing device of the system includes circuitry configured to receive information associated with a microbe profile of an individual. In this example, the microbe profile is received from a microbe profiling kiosk located in a shopping mall that includes an outlet for the cosmetic supplier. The individual samples a portion of his or her skin, e.g., a portion of the face, with a microbe sampling unit, e.g., a swab, which is inserted into the microbe profiling kiosk for analysis as described in U.S. patent application Ser. No. 14/255,653, which is incorporated herein by reference. The microbe profiling kiosk generates a microbe profile that is subsequently transmitted to the computing device of the system. The microbe profile of the individual indicates an above normal level of the genus *Pseudomonas* on the skin surface of the individual.

The computing device of the system includes circuitry configured to receive information associated with an ingredient list of a cosmetic product. The individual provides information to the computing device through a user interface, e.g., a keyboard and monitor. The information includes a list of cosmetic products that he or she is currently using. The computing device includes or has access to a database of cosmetic products and associated ingredient lists. Alternatively, the individual can enter the ingredient list into the computing device using the associated user interface. One of the cosmetic products used by the individual includes isopropyl myristate as a non-greasy emollient for softening the skin.

The computing device of the system includes circuitry configured to compare the received information associated with the microbe profile of the individual and the received information associated with the ingredient list of the cosmetic product to the ingredient-microbe interaction dataset. The comparison includes comparing the types of microbes in the microbe profile of the individual to the types of reference microbes in the ingredient-microbe interaction dataset and comparing the types of cosmetic ingredients in the cosmetic product to the reference cosmetic ingredients in the ingredient-microbe interaction dataset. The computing device of the system identifies an interaction of isopropyl myristate in one of the cosmetic products used by the individual and the above normal levels of the genus *Pseudomonas* in the microbe profile of the individual. Isopropyl myristate has been shown to be a substrate for growth of *Pseudomonas*. See, e.g., Yanagi & Onishi (1971) *J. Soc. Cosmet. Chem.* 22:851-865, which is incorporated herein by reference.

The computing device of the system includes circuitry configured to recommend a modification to the ingredient list of the cosmetic product to alter the identified interaction between isopropyl myristate in the cosmetic product and *Pseudomonas* in the microbe profile of the individual. In this example, the computing device of the system recommends subtraction of isopropyl myristate from the cosmetic product and addition of another emollient, e.g., diisopropyl adipate, the latter of which is not a substrate for *Pseudomonas*.

The computing device of the system includes circuitry configured to send a text message to the individual to indicate the results of the analysis and the recommended modification to the ingredient list of the cosmetic product. The computing device of the system further includes circuitry configured to arrange for delivery of the modified cosmetic product in which diisopropyl adipate has been substituted for isopropyl myristate. The computing system also includes circuitry configured to provide the individual an electronic discount coupon transmitted to the individual's smart phone for purchase of a modified cosmetic product at the cosmetic supplier outlet.

PROPHETIC EXAMPLE 2

A System for Modifying a Cosmetic Product

A system such as described in Prophetic Example 1 is used to modify a cosmetic product based on the microbe profile of an individual. The system includes an ingredient-microbe interaction dataset and a computing device including a processor and circuitry.

The ingredient-microbe interaction dataset includes information associated with interactions between one or more reference cosmetic ingredients and one or more types of reference microbes, e.g., one or more types of microbes within the genus of *Candida, Bacillus*, or *Pseudomonas*. The reference cosmetic ingredients include hydrocarbon, silicone, alcohol, ester, and fatty acid components of cosmetic products as well as mono-ester, di-ester, and tri-ester surfactant/emulsifiers, e.g., polysorbate-20, polysorbate-80, polyethylene glycol, hydrogenated castor oil. The interactions include metabolism of the reference cosmetic ingredients by one or more types of reference microbes, leading to potential effects on a cosmetic product, e.g., effects on color, texture, pH, and/or odor of the cosmetic product.

The computing device of the system includes circuitry configured to receive information associated with a microbe profile of an individual. In this example, the microbe profile is received through the Internet from an at-home microbe profiling kit. The individual samples a portion of his or her skin, e.g., a portion of the face, with a microbe sampling unit, e.g., a peelable facial mask, which is inserted into an analyzer of the at-home microbe profiling kit for analysis as described in U.S. patent application Ser. No. 14/255,653, which is incorporated herein by reference. The analyzer of the at-home microbe profiling kit generates a microbe profile that is subsequently transmitted via the Internet to the computing device of the system. The microbe profile of the individual indicates an above normal level of the genus *Pseudomonas* on the individual's face.

The computing device of the system includes circuitry to receive an ingredient list of a cosmetic product. The individual downloads his or her microbe profile to a website managed by the cosmetic supplier. The website queries the individual regarding currently used cosmetic products and requests a list of cosmetic ingredients. The website further queries the individual to enter additional user information, e.g., age, gender, and contact and payment information. The computing device of the system receives the information associated with the ingredient list of the cosmetic product. One of the cosmetic products used by the individual includes the surfactant/emulsifier polysorbate-20.

The computing device of the system includes circuitry configured to compare the received information associated with the microbe profile of the individual and the ingredient list of the cosmetic product to the ingredient-microbe interaction dataset. The computing device of the system includes circuitry configured to identify an interaction of polysorbate-20 in one of the cosmetic products used by the individual and the above normal levels of the genus *Pseudomonas* in the microbe profile of the individual. Polysorbate-20 has been shown to deteriorate in the presence of *Pseudomonas* due to a lipase associated with the microorganism, potentially causing a change in texture of the cosmetic product.

See, e.g., Wachi, et al (1980) *J. Soc. Cosmet. Chem.* 31:67-84, which is incorporated herein by reference.

The computing device of the system includes circuitry configured to recommend a modification to the ingredient list of the cosmetic product to alter the identified potential interaction of polysorbate-20 with *Pseudomonas* on the skin surface of the individual. In this example, the computing device of the system recommends subtraction of polysorbate-20 from the ingredient list of the cosmetic product and addition of a di-ester or tri-ester surfactant/emulsifier, the latter of which are not as readily decomposed by *Pseudomonas*. Alternatively, the computing device of the system recommends addition of a lipase inhibitor to attenuate the *Pseudomonas* lipase activity.

The computing device of the system includes circuitry configured to send an e-mail message to the individual to indicate the results of the analysis and the recommended modifications to the ingredient list of the cosmetic product. The computing device of the system can also include circuitry configured to arrange for delivery of a modified cosmetic product to an address provided by the individual. The modified cosmetic product includes a cosmetic product in which a di-ester and/or tri-ester surfactant/emulsifier has been substituted for polysorbate-20 and/or in which a lipase inhibitor has been added.

PROPHETIC EXAMPLE 3

A System for Modifying a Cosmetic Product Based on a Microbe Profile of an Individual and User Preference A system is described for modifying a cosmetic product based on the microbe profile of an individual and a user preference. In this example, the individual has a user preference that includes development of a color or color change over the time of wearing the cosmetic product. The system includes an ingredient-microbe interaction dataset and a computing device including a processor and circuitry. The system is associated with a kiosk of a cosmetic supplier that specializes in formulating personalized cosmetic products based on an individual's microbe profile and the user preferences of the individual. In this example, the preferences of the individual relate to a preferred color.

The ingredient-microbe interaction dataset includes information associated with the interactions between one or more reference cosmetic ingredients, e.g., pigments or chromogenic substrates, and one or more types of reference microbes. The reference cosmetic ingredients include one or more pigments or chromogenic substrates that respond to interaction with specific microbial enzymes by releasing a detectable color. The one or more types of reference microbes include one or more types of microbes resident on the skin surface, and particularly on the skin surface of the face, e.g., *Staphylococcus epidermidis* and *Propionibacterium acnes*. The one or more interactions include one or more potential color effects. See, e.g., Manafi et al (1991) *Microbiological Reviews* 55:335-348, which is incorporated herein by reference.

The computing device of the system includes circuitry configured to receive the information associated with the microbe profile of the individual accessible to the computing device through a portable data storage device, e.g., a flash drive. The portable data storage device includes a microbe profile of an individual generated using an at-home microbe profiling system. The individual downloads the microbe profile to the flash drive from the at-home microbe profiling system and transports the flash drive to the cosmetic supplier. The individual inserts the flash drive into a USB port associated with the kiosk. The individual interacts with the kiosk through a user interface, e.g., a touchscreen display. The individual is queried to enter user information as well as user preferences, e.g., color preferences. In this example, the individual uses a touchscreen display associated with the kiosk to enter his or her color preferences. In this example, the color preference is mauve or purple.

The computing device of the system includes circuitry configured to compare the information associated with the microbe profile of the individual with the reference microbe profiles and potential color effects. The microbe profile of the individual includes *Staphylococcus epidermidis*. The computing device identifies several chromogenic substrates that interact with *Staphylococcus epidermidis* to generate a mauve-like color. These include 5-bromo-5-chloro-3-indoxyl phosphate and 5-bromo-4-chloro-3-indoxyl glucoside. See, e.g., U.S. Pat. No. 6,548,268, which is incorporated herein by reference.

The computing device of the system includes circuitry configured to recommend a modification to a cosmetic product to alter the identified interaction between one or more cosmetic ingredients in a cosmetic product and one or more types of microbes in the microbe profile of the individual. In this example, the computing device recommends the addition of one or more cosmetic ingredients, e.g., one or more chromogenic substrate, based on the microbe profile, e.g., the presence of *Staphylococcus epidermidis*, and a desired color effect, e.g., mauve. The computing device includes circuitry configured to recommend a modification to the cosmetic product, e.g., a foundation, to include one or more chromogenic substrates, e.g., 5-bromo-5-chloro-3-indoxyl phosphate and 5-bromo-4-chloro-3-indoxyl glucoside. The computing device of the system further includes circuitry configured to arrange for delivery of the modified cosmetic product to the individual.

PROPHETIC EXAMPLE 4

A System for Modifying a Cosmetic Product Based on a Microbe Profile

A system is described for modifying a cosmetic product based on a microbe profile. The system includes an ingredient-microbe interaction dataset and a computing device including a processor and circuitry. The system is associated with a dermatology medical office.

The system includes an ingredient-microbe interaction dataset stored on the computing device of the system including information associated with interactions between one or more reference cosmetic ingredients, e.g., probiotic agents and prebiotic agents, and one or more types of reference microbes, e.g., one or more skin-resident microbes.

The computing device of the system is operably coupled to a microbe profiling system in the dermatology medical office. The computing device of the system includes circuitry configured to receive a microbe profile of the individual. The microbe profile is generated by a medical technician in the dermatology medical office using the microbe profiling system and downloaded onto the computing device for further analysis. The computing device of the system includes circuitry configured to receive an ingredient list of a cosmetic product. In this example, the cosmetic product, e.g., a moisturizing and anti-aging cream, is not currently used by the individual but is being recommended to the individual by his or her dermatologist. Prior to providing the cosmetic product to the individual, the dermatologist wants to ensure that it is appropriate based on the microbe profile of the individual. The microbe profile of the individual reveals a higher than average amount of several bacterial strains including strains of *Staphylococcus epidermidis, Staphylococcus aureus*, and *Propionibacterium acnes*.

The computing device of the system includes circuitry configured to compare the microbe profile of the individual and the ingredient list of the cosmetic product to the ingredient-microbe interaction dataset. The computing device identifies an interaction between one or more probiotic strains listed in the ingredient-microbe interaction dataset and the bacterial strains, e.g., *Staphylococcus epidermidis, Staphylococcus aureus*, and *Propionibacterium acnes* identified in the microbe profile of the individual. The computing device recommends a modification to the ingredient list of the cosmetic product to add a probiotic agent, e.g., a strain of *Lactococcus lacti*, to attenuate the growth of the identified bacterial strains in the microbe profile of the individual through competitive growth of the added probiotic. See, e.g., Kumari et al (2009) *Int. J. Probiotics Prebiotics* 4:205-210, which is incorporated herein by reference. The dermatology medical office includes a compounding formulary capable of adding the recommended probiotic agent to the cosmetic product prior to distribution to the individual.

The individual is advised to use the modified cosmetic product for 2 to 3 weeks and to repeat the microbe profile using an at-home microbe profiling device provided by the dermatologist to determine whether or not the modified cosmetic product has altered the individual's microbe profile, e.g., increased or decreased the growth of the bacterial strains of *Staphylococcus epidermidis, Staphylococcus aureus*, and *Propionibacterium acnes*.

PROPHETIC EXAMPLE 5

A System for Modifying a Buffering Capacity of a Cosmetic Product Based on a Microbe Profile A system is described for modifying a buffering capacity of a cosmetic product based on a microbe profile. The system includes an ingredient-microbe interaction dataset and a computing device including a processor and circuitry. The system is associated with a cosmetic formulary. The individual has been using a new cosmetic product for several weeks, but wants to confirm that the product is appropriate for his or her microbe profile based on the individual's age and gender.

The computing device of the system associated with the cosmetic formulary includes circuitry configured to receive the microbe profile of the individual from a flash drive provided by the individual. The microbe profile of the individual is generated using an at-home microbe profiling system and downloaded to the flash drive for portability. The computing device includes circuitry configured to compare the microbe profile received from the flash drive with at least one normalized reference microbe profile stored in the memory component of the computing device to determine how the microbe profile of the individual compares with the microbe profiles of age- and gender-matched individuals. The comparison indicates the presence of *Staphylococcus aureus* and *Streptococcus pyogenes* at levels above normal in the individual's microbe profile. The computing device includes circuitry configured to recommend a modification to the ingredient list of the cosmetic product to inhibit the growth of *Staphylococcus aureus* and *Streptococcus pyo-*

*genes. Staphylococcus aureus* and *Streptococcus pyogenes* are inhibited in the presence of low pH. See, e.g., Grise (2011) Nat. Rev. Microbiol. 9:244-253, which is incorporated herein by reference. The computing device includes circuitry configured to recommend adding a buffer, a weak acid buffering system, to the cosmetic product to maintain a lower pH on the skin surface of the individual to inhibit the growth of *Staphylococcus aureus* and *Streptococcus pyogenes*.

The computing device of the system includes circuitry configured to arrange for delivery of a modified cosmetic product, the modified cosmetic product including a weak acid buffering system. The individual is advised to use the modified cosmetic product for 7 to 10 days and to repeat the microbe profile using the at-home microbe profiling system to determine whether or not the modified cosmetic product has altered the individual's microbe profile, e.g., attenuated the presence of *Staphylococcus aureus* and *Streptococcus pyogenes*.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for modifying a cosmetic product, comprising:
    an ingredient-microbe interaction dataset including information associated with chemical interactions between one or more reference cosmetic ingredients and one or more types of reference microbes, wherein said chemical interactions alter at least one of a color, a texture, or an odor of the one or more reference cosmetic ingredients;
    and
    a computing device in communication with the filling apparatus, the computing device including a processor and circuitry, the circuitry including
        circuitry configured to receive information associated with a microbe profile of an individual, the microbe profile including a distribution and identity of one or more types of microbes on a skin surface of the individual;
        circuitry configured to receive information associated with an ingredient list of the cosmetic product, the ingredient list including one or more cosmetic ingredients;
        circuitry configured to compare the ingredient-microbe interaction dataset to the received information associated with the microbe profile of the individual and the received information associated with the ingredient list of the cosmetic product;
        circuitry configured to identify a chemical interaction between at least one of the one or more cosmetic ingredients in the ingredient list of the cosmetic product and at least one of the one or more types of microbes in the microbe profile of the individual, wherein the identified chemical interaction alters at least one of a color, a texture, or an odor of the at least one of the one or more cosmetic ingredients;
        circuitry configured to recommend a modification to the ingredient list of the cosmetic product in response to the identified chemical interaction between the at least one of the one or more cosmetic ingredients in the ingredient list of the cosmetic product and the at least one of the one or more types of microbes in the microbe profile of the individual; and
        circuitry configured to report the recommended modification to the ingredient list of the cosmetic product to a manufacturer to formulate a modified cosmetic product based on the recommended modification.

2. The system of claim 1 wherein the circuitry configured to report the recommended modification to the ingredient list of the cosmetic product to the manufacturer includes circuitry configured to report the recommended modification to a remote computing device associated with the manufacturer.

3. The system of claim 1, wherein the circuitry configured to receive the information associated with the microbe profile of the individual includes circuitry configured to receive the information associated with the microbe profile of the individual from a microbe profiling apparatus.

4. The system of claim 1, further comprising:
    a microbe profiling apparatus capable of communication with the computing device, the microbe profiling apparatus including a microbe sampling unit including a microbe-capture region configured to capture one or more types of microbes from the skin surface of the individual, at least one sensor component configured to sense the captured one or more types of microbes, and circuitry configured to generate the microbe profile of the individual based on the sensed captured one or more types of microbes, wherein the microbe profile includes the distribution and the identity of the one or more types of microbes on the skin surface of the individual.

5. The system of claim 1, wherein the circuitry configured to receive the information associated with the ingredient list of the cosmetic product includes circuitry configured to receive the information associated with the ingredient list of the cosmetic product from a remote computing device associated with at least one of a cosmetic distributer, a cosmetic manufacturer, or a cosmetic formulary.

6. The system of claim 1, wherein the circuitry configured to receive the information associated with the ingredient list of the cosmetic product includes circuitry configured to receive information associated with the ingredient list of the cosmetic product from a scanning device configured to scan and digitize an ingredient label of the cosmetic product.

7. The system of claim 1, further comprising:
    a scanning device operably coupled to the computing device and including circuitry configured to scan and digitize an ingredient label of the cosmetic product, the ingredient label including the ingredient list of the cosmetic product, wherein the computing device includes circuitry configured to receive the digitized ingredient label including the ingredient list of the cosmetic product from the scanning device.

8. The system of claim 1, wherein the circuitry configured to compare the ingredient-microbe interaction dataset to the received information associated with the microbe profile of the individual and the received information associated with the ingredient list of the cosmetic product includes circuitry configured to compare the one or more types of microbes in the microbe profile of the individual to the one or more types of reference microbes in the ingredient-microbe interaction dataset and circuitry configured to compare the one or more cosmetic ingredients in the ingredient list of the cosmetic product to the one or more reference cosmetic ingredients in the ingredient-microbe interaction dataset.

9. The system of claim 1, wherein the identified chemical interaction alters a pH of the one or more cosmetic ingredients.

10. The system of claim 1, wherein the circuitry configured to recommend a modification to the ingredient list of the cosmetic product in response to the identified chemical interaction includes circuitry configured to recommend a modification to the ingredient list of the cosmetic product to alleviate the identified chemical interaction or to enhance the identified chemical interaction.

11. The system of claim 1, wherein the circuitry configured to recommend a modification to the ingredient list of the cosmetic product in response to the identified chemical interaction includes circuitry configured to recommend an addition or a subtraction of at least a portion of at least one cosmetic ingredient to or from the ingredient list of the cosmetic product.

12. The system of claim 1, further comprising:
a user interface operably coupled to the computing device;
the computing device including
circuitry configured to receive user information from the individual through the user interface, wherein the user information includes at least one of age, gender, ethnicity, geographical location, skin characteristics, medical history, co-morbidities, or user preferences; and
circuitry configured to recommend the modification to the ingredient list of the cosmetic product based on the identified chemical interaction and the received user information.

13. The system of claim 1, further comprising:
circuitry configured to report the recommended modification to the ingredient list of the cosmetic product to the individual through at least one of a display, a printout, a telephone call, a text message, or an e-mail.

14. The system of claim 1, further comprising:
circuitry configured to provide to the individual at least one discount coupon for purchase of the modified cosmetic product.

15. The system of claim 1, further comprising:
circuitry configured to arrange for delivery of the modified cosmetic product.

16. A method, comprising:
receiving information associated with a microbe profile of an individual, the microbe profile including a distribution and identity of one or more types of microbes on a skin surface of the individual;
receiving information associated with an ingredient list of a cosmetic product, the ingredient list of the cosmetic product including one or more cosmetic ingredients;
accessing an ingredient-microbe interaction dataset, the ingredient-microbe interaction dataset including information associated with chemical interactions between one or more reference cosmetic ingredients and one or more types of reference microbes, wherein said chemical interactions alter at least one of a color, a texture, or an odor of the one or more reference cosmetic ingredients;
comparing the received information associated with the microbe profile of the individual and the received information associated with the ingredient list of the cosmetic product to the ingredient-microbe interaction dataset;
identifying a chemical interaction between at least one of the one or more cosmetic ingredients in the ingredient list of the cosmetic product and at least one of the one or more types of microbes in the microbe profile of the individual based on the comparison with the ingredient-microbe interaction dataset, wherein the chemical interaction alters at least one of a color, a texture, or an odor of the at least one of the one or more cosmetic ingredients;
recommending a modification to the ingredient list of the cosmetic product in response to the identified chemical interaction between the at least one of the one or more cosmetic ingredients in the ingredient list of the cosmetic product and the at least one of the one or more types of microbes in the microbe profile of the individual; and
reporting the recommended modification to the ingredient list of the cosmetic product to a computing device operably coupled to a filling apparatus; and
filling a cosmetic container with a modified cosmetic product using the filling apparatus based on the recommended modification to the ingredient list of the cosmetic product.

17. The method of claim 16, wherein receiving the information associated with the ingredient list of the cosmetic product comprises receiving the information associated with the ingredient list of the cosmetic product from a scanning device configured to scan and digitize an ingredient label of the cosmetic product, the ingredient label including the ingredient list of the cosmetic product.

18. The method of claim 16, further comprising:
receiving information about the individual including at least one of age, gender, ethnicity, geographical location, skin characteristics, medical history, co-morbidities, or user preferences of the individual; and
recommending the modification to the ingredient list of the cosmetic product based on the identified chemical interaction and the received information about the individual.

19. The method of claim 16, further comprising:
reporting the recommended modification to the ingredient list of the cosmetic product to a user interface.

20. The method of claim 16, further comprising:
providing to the individual at least one discount coupon for purchase of the modified cosmetic product including the recommended modification to the ingredient list.

21. The method of claim 16, further comprising:
arranging for delivery of the modified cosmetic product including the recommended modification to the ingredient list.

22. A system for modifying a cosmetic product, comprising:
a computing device including a processor; and
circuitry including
circuitry for receiving information associated with a microbe profile of an individual, the microbe profile including a distribution of one or more types of microbes on a skin surface of the individual;
circuitry for receiving information associated with an ingredient list of the cosmetic product, the ingredient list of the cosmetic product including one or more cosmetic ingredients;
circuitry for comparing the received information associated with the microbe profile of the individual and the received information associated with the ingredient list of the cosmetic product to an ingredient-microbe interaction dataset, the ingredient-microbe interaction dataset including information associated with chemical interactions between one or more reference cosmetic ingredients and one or more types of reference microbes, wherein said chemical interactions alter at least one of a color, a texture, or an odor of the one or more reference cosmetic ingredients;

circuitry for identifying a chemical interaction between at least one of the one or more cosmetic ingredients in the ingredient list of the cosmetic product and at least one of the one or more types of microbes in the microbe profile of the individual based on the comparison with the ingredient-microbe interaction dataset, wherein the chemical interactions alter at least one of a color, texture, or an odor of the one or more reference cosmetic ingredients;

circuitry for recommending a modification to the ingredient list of the cosmetic product in response to the identified chemical interaction between the at least one of the one or more cosmetic ingredients in the ingredient list of the cosmetic product and the at least one of the one or more types of microbes in the microbe profile of the individual;

circuitry for reporting the recommended modification to the ingredient list of the cosmetic product to a manufacturer to formulate a modified cosmetic product based on the recommended modification; and circuitry for reporting the recommended modification to the ingredient list of the cosmetic product to the individual.

23. The system of claim 22, further comprising:
a microbe profiling apparatus capable of communication with the computing device and including a microbe sampling unit including a microbe capture region configured to capture one or more types of microbes from a skin surface of an individual, at least one sensor component configured to sense the captured one or more types of microbes, and circuitry configured to generate the microbe profile based on the sensed captured one or more types of microbes.

24. The system of claim 22, further comprising:
a scanning device capable of communication with the computing device and including circuitry configured to scan and digitize an ingredient label of the cosmetic product, the ingredient label including the ingredient list of the cosmetic product, wherein the computing device includes circuitry configured to receive the digitized ingredient label including the ingredient list of the cosmetic product from the scanning device.

25. The system of claim 22, further comprising:
a user interface operably coupled to the computing device, wherein the computing device includes circuitry for receiving user information from the individual and circuitry for recommending the modification to the ingredient list of the cosmetic product based on the identified chemical interaction and the user information, wherein the user information includes at least one of age, gender, ethnicity, geographical location, skin characteristics, medical history, co-morbidities, or user preferences.

26. A system for modifying a cosmetic product, comprising:
an ingredient list of the cosmetic product, the ingredient list including one or more cosmetic ingredients;
an ingredient-microbe interaction dataset including information associated with chemical interactions between one or more reference cosmetic ingredients and one or more types of reference microbes, wherein said chemical interactions alter at least one of a color, a texture, or an odor of the one or more reference cosmetic ingredients, the ingredient-microbe interaction dataset accessible from a remote computing source;

non-transitory machine-readable media configured for use with a wireless mobile communication device, the non-transitory machine-readable media including one or more instructions for modifying the cosmetic product, the one or more instructions including
one or more instructions for receiving information associated with the ingredient list of the cosmetic product;
one or more instructions for accessing the ingredient-microbe interaction dataset from the remote computing source;
one or more instructions for receiving information associated with a microbe profile of an individual, the microbe profile including a distribution of one or more types of microbes on a skin surface of the individual;
one or more instructions for comparing the accessed ingredient-microbe interaction dataset to the received information associated with the ingredient list of the cosmetic product and the received information associated with the microbe profile of the individual;
one or more instructions for identifying a chemical interaction between at least one of the one or more cosmetic ingredients in the ingredient list of the cosmetic product and at least one of the one or more types of microbes in the microbe profile of the individual based on the comparison with the ingredient-microbe interaction dataset, wherein the identified chemical interaction alters at least one of a color, a texture, or an odor of the at least one of the one or more cosmetic ingredients;
one or more instructions for recommending a modification to the ingredient list of the cosmetic product in response to the identified chemical interaction between the at least one of the one or more cosmetic ingredients in the ingredient list of the cosmetic product and the at least one of the one or more types of microbes in the microbe profile of the individual;
one or more instructions for reporting the recommended modification to the ingredient list of the cosmetic product to a manufacturer to formulate a modified cosmetic product based on the recommended modification; and
one or more instructions for reporting the recommended modification to the ingredient list of the cosmetic product to the individual.

27. A system for modifying a cosmetic product, comprising:
an ingredient-microbe interaction dataset including information associated with interactions between one or more reference cosmetic ingredients and one or more types of reference microbes;
a scanning device including circuitry configured to scan and digitize an ingredient label of the cosmetic product, the ingredient label including an ingredient list of the cosmetic product, the ingredient list including one or more cosmetic ingredients; and
a mobile communication device capable of communication with the scanning device, the mobile communication device including a user interface, a processor and circuitry, the circuitry including circuitry configured to receive information associated with a microbe profile of an individual, the microbe profile including a distribution and identity of one or more types of microbes on a skin surface of the individual;

circuitry configured to receive information associated with the ingredient list of the cosmetic product from the scanning device;

circuitry configured to compare the ingredient-microbe interaction dataset to the received information associated with the microbe profile of the individual and the received information associated with the ingredient list of the cosmetic product;

circuitry configured to identify an interaction between at least one of the one or more cosmetic ingredients in the ingredient list of the cosmetic product and at least one of the one or more types of microbes in the microbe profile of the individual;

circuitry configured to recommend a modification to the ingredient list of the cosmetic product in response to the identified interaction between the at least one of the one or more cosmetic ingredients in the ingredient list of the cosmetic product and the at least one of the one or more types of microbes in the microbe profile of the individual;

circuitry configured to report the recommended modification to the ingredient list of the cosmetic product to a manufacturer to formulate a modified cosmetic product based on the recommended modification; and circuitry configured to report the recommended modification to the ingredient list of the cosmetic product to the user interface of the mobile communication device.

\* \* \* \* \*